(12) United States Patent
Newell et al.

(10) Patent No.: US 11,266,456 B2
(45) Date of Patent: Mar. 8, 2022

(54) CRYOGENIC ABLATION SYSTEM WITH ROTATABLE AND TRANSLATABLE CATHETER

(71) Applicant: PENTAX OF AMERICA, INC., Montvale, NJ (US)

(72) Inventors: Gabriel F. W. Newell, San Francisco, CA (US); Patrick P. Wu, San Carlos, CA (US); Timothy Douglas Holland, Los Gatos, CA (US); Cesar A. Ico, San Francisco, CA (US); Dennis Franklin Burke, Manteca, CA (US)

(73) Assignee: PENTAX OF AMERICA, INC., Montvale, NJ (US)

( * ) Notice: Subject to any disclaimer, the term of this patent is extended or adjusted under 35 U.S.C. 154(b) by 459 days.

(21) Appl. No.: 16/171,233

(22) Filed: Oct. 25, 2018

(65) Prior Publication Data

US 2019/0059970 A1 Feb. 28, 2019

Related U.S. Application Data

(63) Continuation of application No. 15/593,790, filed on May 12, 2017, now Pat. No. 10,251,693.
(Continued)

(51) Int. Cl.
*A61B 18/02* (2006.01)
*A61B 90/98* (2016.01)
(Continued)

(52) U.S. Cl.
CPC .............. *A61B 18/02* (2013.01); *A61B 90/98* (2016.02); *A61B 2017/00017* (2013.01);
(Continued)

(58) Field of Classification Search
CPC .............. A61B 18/02; A61B 2090/064; A61B 2090/0809; A61B 2090/0811;
(Continued)

(56) References Cited

U.S. PATENT DOCUMENTS

| 4,333,452 A | 6/1982 | Au |
| 4,924,862 A | 5/1990 | Levinson |

(Continued)

FOREIGN PATENT DOCUMENTS

| CN | 101584602 A | 11/2009 |
| CN | 101972513 A | 2/2011 |

(Continued)

OTHER PUBLICATIONS

U.S. Appl. No. 13/766,567—Restriction Requirement dated Nov. 19, 2013, 11 pages.
(Continued)

*Primary Examiner* — Michael F Peffley
*Assistant Examiner* — Bo Ouyang
(74) *Attorney, Agent, or Firm* — Haynes Beffel & Wolfeld LLP; Andrew Dunlap

(57) ABSTRACT

An ablation assembly includes a handle, a catheter assembly and a connector locking assembly. The catheter assembly includes: a catheter shaft, a balloon and a connector at the distal and proximal ends of the catheter shaft, and a delivery tube extending between there between. The connector includes a connector body secured to the proximal end and a plug secured to the delivery tube, the plug and delivery tube movable axially and rotationally. The handle includes an open portion receiving the plug and the connector body. The connector locking assembly includes: means for simultaneously automatically connecting the plug and the connector body to the handle to place the connector in a load state prior to use, and means for automatically releasing the
(Continued)

connector body and thereafter the plug from the handle to place the connector in an eject state to permit the connector to be removed from the handle.

19 Claims, 34 Drawing Sheets

Related U.S. Application Data

(60) Provisional application No. 62/339,611, filed on May 20, 2016.

(51) Int. Cl.
  *A61B 90/00* (2016.01)
  *A61B 17/00* (2006.01)
  *A61B 18/00* (2006.01)

(52) U.S. Cl.
  CPC .......... *A61B 2017/0046* (2013.01); *A61B 2017/00398* (2013.01); *A61B 2017/00477* (2013.01); *A61B 2017/00973* (2013.01); *A61B 2018/0022* (2013.01); *A61B 2018/00041* (2013.01); *A61B 2018/00208* (2013.01); *A61B 2018/00488* (2013.01); *A61B 2018/00494* (2013.01); *A61B 2018/00553* (2013.01); *A61B 2018/00577* (2013.01); *A61B 2018/00648* (2013.01); *A61B 2018/00714* (2013.01); *A61B 2018/00744* (2013.01); *A61B 2018/00815* (2013.01); *A61B 2018/00916* (2013.01); *A61B 2018/0212* (2013.01); *A61B 2018/0268* (2013.01); *A61B 2090/064* (2016.02); *A61B 2090/0809* (2016.02); *A61B 2090/0811* (2016.02)

(58) Field of Classification Search
  CPC ........... A61B 2018/00041; A61B 2018/00208; A61B 2018/0022
  See application file for complete search history.

(56) References Cited

U.S. PATENT DOCUMENTS

| | | | |
|---|---|---|---|
| 5,035,705 A | 7/1991 | Burns | |
| 5,342,301 A | 8/1994 | Saab | |
| 5,868,735 A | 2/1999 | Lafontaine | |
| 5,971,979 A | 10/1999 | Joye et al. | |
| 6,027,499 A | 2/2000 | Johnston et al. | |
| 6,283,959 B1 | 9/2001 | Lalonde et al. | |
| 6,355,029 B1 | 3/2002 | Joye et al. | |
| 6,383,181 B1 | 5/2002 | Johnston et al. | |
| 6,383,203 B1 | 5/2002 | Makihara | |
| 6,428,534 B1 | 8/2002 | Joye et al. | |
| 6,443,947 B1 | 9/2002 | Marko et al. | |
| 6,468,297 B1 | 10/2002 | Williams et al. | |
| 6,514,245 B1 | 2/2003 | Williams et al. | |
| 6,537,271 B1 | 3/2003 | Murray et al. | |
| 6,551,274 B2 | 4/2003 | Heiner | |
| 6,626,861 B1 | 9/2003 | Hart et al. | |
| 6,648,878 B2 | 11/2003 | Lafontaine | |
| 6,666,858 B2 | 12/2003 | Lafontaine | |
| 6,709,431 B2 | 3/2004 | Lafontaine | |
| 6,746,465 B2 | 6/2004 | Diederich et al. | |
| 6,786,901 B2 | 9/2004 | Joye et al. | |
| 6,875,209 B2 | 4/2005 | Zvuloni et al. | |
| 6,905,510 B2 | 6/2005 | Saab | |
| 6,908,462 B2 | 6/2005 | Joye et al. | |
| 6,929,639 B2 | 8/2005 | Lafontaine | |
| 6,953,469 B2 | 10/2005 | Ryan | |
| 7,022,120 B2 | 4/2006 | Lafontaine | |
| 7,025,762 B2 | 4/2006 | Johnston et al. | |
| 7,156,860 B2 | 1/2007 | Wallsten et al. | |
| 7,220,257 B1 | 5/2007 | Lafontaine | |
| 7,727,228 B2 | 6/2010 | Abboud et al. | |
| 8,038,598 B2 | 10/2011 | Khachi | |
| 8,172,747 B2 | 5/2012 | Wallace et al. | |
| 8,382,746 B2 | 2/2013 | Williams et al. | |
| 8,409,266 B2 | 4/2013 | Lafontaine | |
| 8,740,895 B2 | 6/2014 | Mayse et al. | |
| 9,017,324 B2 | 4/2015 | Mayse et al. | |
| 9,050,073 B2 | 6/2015 | Newell et al. | |
| 9,168,081 B2 | 10/2015 | Williams et al. | |
| 9,414,878 B1 | 8/2016 | Wu et al. | |
| 2002/0007179 A1 | 1/2002 | Dobak et al. | |
| 2002/0010460 A1 | 1/2002 | Joye et al. | |
| 2002/0026182 A1 | 2/2002 | Joye et al. | |
| 2002/0062122 A1 | 5/2002 | Lehmann et al. | |
| 2003/0060762 A1 | 3/2003 | Zvuloni et al. | |
| 2003/0060813 A1 | 3/2003 | Loeb et al. | |
| 2003/0088240 A1 | 5/2003 | Saadat | |
| 2004/0147811 A1 | 7/2004 | Diederich et al. | |
| 2004/0210281 A1 | 10/2004 | Dzeng et al. | |
| 2004/0215296 A1 | 10/2004 | Ganz et al. | |
| 2004/0243119 A1 | 12/2004 | Lane et al. | |
| 2005/0137619 A1 | 6/2005 | Schewe et al. | |
| 2005/0209587 A1* | 9/2005 | Joye | A61B 18/02 606/21 |
| 2005/0245943 A1 | 11/2005 | Zvuloni et al. | |
| 2006/0030843 A1 | 2/2006 | Lane et al. | |
| 2006/0041256 A1 | 2/2006 | Edwards et al. | |
| 2006/0086362 A1 | 4/2006 | Solomon | |
| 2006/0259029 A1 | 11/2006 | Utley et al. | |
| 2007/0066962 A1 | 3/2007 | Rutter | |
| 2007/0250050 A1 | 10/2007 | Lafontaine | |
| 2007/0299433 A1 | 12/2007 | Williams et al. | |
| 2007/0299443 A1 | 12/2007 | DiPoto et al. | |
| 2008/0262476 A1 | 10/2008 | Krause et al. | |
| 2008/0312644 A1 | 12/2008 | Fourkas et al. | |
| 2009/0099638 A1* | 4/2009 | Grewe | A61F 2/966 623/1.11 |
| 2009/0099639 A1 | 4/2009 | Sabaria | |
| 2009/0118723 A1 | 5/2009 | Lalonde et al. | |
| 2009/0182317 A1 | 7/2009 | Bencini | |
| 2009/0209949 A1 | 8/2009 | Ingle et al. | |
| 2009/0234345 A1 | 9/2009 | Hon | |
| 2010/0130970 A1 | 5/2010 | Williams et al. | |
| 2010/0249601 A1 | 9/2010 | Courtney | |
| 2011/0184398 A1 | 7/2011 | Desrochers | |
| 2012/0101485 A1 | 4/2012 | Wittenberger | |
| 2012/0130458 A1 | 5/2012 | Ryba et al. | |
| 2012/0143177 A1 | 6/2012 | Avitall | |
| 2012/0172072 A1 | 7/2012 | Baxter et al. | |
| 2012/0197245 A1 | 8/2012 | Burnett et al. | |
| 2013/0012772 A1 | 1/2013 | Gunday et al. | |
| 2013/0018366 A1 | 1/2013 | Wu et al. | |
| 2013/0023770 A1 | 1/2013 | Courtney et al. | |
| 2013/0030425 A1 | 1/2013 | Stewart et al. | |
| 2013/0110100 A1 | 5/2013 | Groves et al. | |
| 2013/0197500 A1 | 8/2013 | Williams et al. | |
| 2013/0231650 A1 | 9/2013 | Watson | |
| 2013/0231651 A1 | 9/2013 | Burr et al. | |
| 2013/0253491 A1 | 9/2013 | Burr et al. | |
| 2013/0289549 A1 | 10/2013 | Nash et al. | |
| 2013/0304061 A1 | 11/2013 | Chang et al. | |
| 2013/0345688 A1 | 12/2013 | Babkin et al. | |
| 2015/0045826 A1 | 2/2015 | Drasler et al. | |
| 2015/0126985 A1* | 5/2015 | Newell | A61B 18/02 606/21 |
| 2015/0190036 A1 | 7/2015 | Saadat | |
| 2015/0196345 A1 | 7/2015 | Newell et al. | |
| 2015/0230700 A1 | 8/2015 | Chandler et al. | |
| 2015/0265329 A1 | 9/2015 | Lalonde et al. | |
| 2015/0342660 A1 | 12/2015 | Nash | |
| 2016/0066975 A1 | 3/2016 | Fourkas et al. | |
| 2016/0302841 A1 | 10/2016 | Williams et al. | |

FOREIGN PATENT DOCUMENTS

| | | |
|---|---|---|
| CN | 102223848 A | 10/2011 |
| CN | 102639077 A | 8/2012 |
| CN | 102715950 A | 10/2012 |

(56) References Cited

FOREIGN PATENT DOCUMENTS

| | | |
|---|---|---|
| CN | 102883659 A | 1/2013 |
| CN | 103200891 A | 7/2013 |
| CN | 103930153 A | 7/2014 |
| CN | 104244854 A | 12/2014 |
| CN | 104271064 A | 1/2015 |
| CN | 105705108 B | 12/2017 |
| EP | 0925045 A1 | 6/1999 |
| JP | 2000504967 A | 4/2000 |
| JP | 2000516696 A | 12/2000 |
| JP | 2001511690 A | 8/2001 |
| JP | 2001524345 A | 12/2001 |
| JP | 2004516042 A | 6/2004 |
| JP | 2005503241 A | 2/2005 |
| JP | 2008000553 A | 1/2008 |
| JP | 4117958 B2 | 7/2008 |
| JP | 2008523897 A | 7/2008 |
| JP | 2008245954 A | 10/2008 |
| JP | 2012509146 A | 4/2012 |
| JP | 2015-509791 A | 4/2015 |
| JP | 6402317 B2 | 10/2018 |
| WO | 9804221 A1 | 2/1998 |
| WO | 9836783 A1 | 8/1998 |
| WO | 9927862 A1 | 6/1999 |
| WO | 9955401 A1 | 11/1999 |
| WO | 03026719 A2 | 4/2003 |
| WO | 2008042890 A1 | 4/2008 |
| WO | 2010059519 A1 | 5/2010 |
| WO | 2010078175 A1 | 7/2010 |
| WO | 2012162829 A1 | 12/2012 |
| WO | 2013110156 A1 | 8/2013 |
| WO | 2013163325 A2 | 10/2013 |
| WO | 2014026055 A1 | 2/2014 |
| WO | 2014089380 A2 | 6/2014 |
| WO | 2014137383 A1 | 9/2014 |
| WO | 2015066521 A1 | 5/2015 |
| WO | 2015188013 A1 | 12/2015 |
| WO | 2016025964 A1 | 2/2016 |
| WO | 2016186964 A1 | 11/2016 |
| WO | 2017200877 A1 | 11/2017 |

OTHER PUBLICATIONS

U.S. Appl. No. 14/530,288—Notice of Allowance dated Mar. 31, 2015, 8 pages.
U.S. Appl. No. 14/530,288—Office Action dated Jan. 14, 2015, 12 pages.
U.S. Appl. No. 14/530,288—Response to Office Action dated Jan. 14, 2015 filed Mar. 18, 2015, 15 pages.
U.S. Appl. No. 14/667,421—Final Office Action dated Nov. 10, 2016, 12 pages.
U.S. Appl. No. 14/667,421—Final Office Action dated Feb. 3, 2016, 10 pages.
U.S. Appl. No. 14/667,421—Notice of Allowance dated Mar. 6, 2017, 8 pages.
U.S. Appl. No. 14/667,421—Office Action dated Jun. 13, 2016, 10 pages.
U.S. Appl. No. 14/667,421—Office Action dated May 14, 2015, 9 pages.
U.S. Appl. No. 14/667,421—Response to Final Office Action dated Nov. 10, 2016 filed Feb. 10, 2017, 7 pages.
U.S. Appl. No. 14/667,421—Response to Final Office Action dated Feb. 3, 2016 Office filed May 3, 2016, 6 pages.
U.S. Appl. No. 14/667,421—Response to Office Action dated Jun. 13, 2016 filed Aug. 9, 2016, 6 pages.
U.S. Appl. No. 14/667,421—Response to Office Action dated May 14, 2015 filed Sep. 24, 2015, 6 pages.
U.S. Appl. No. 14/714,101—Notice of Allowance dated Apr. 18, 2016, 9 pages.
U.S. Appl. No. 14/714,101—Office Action dated Nov. 27, 2015, 12 pages.
U.S. Appl. No. 14/714,101—Response to Office Action dated Nov. 27, 2015 filed Feb. 23, 2016, 8 pages.
U.S. Appl. No. 14/876,035—Office Action dated May 29, 2018, 9 pages.
U.S. Appl. No. 15/593,790—Office Action dated Dec. 14, 2017, 19 pages.
U.S. Appl. No. 15/593,790—Office Action dated May 29, 2018, 19 pages.
CN 200980146533.8—1st Office Action dated Dec. 5, 2012, 9 pages with translation included.
CN 200980146533.8—2nd Office Action dated Aug. 19, 2013, 11 pages with translation included.
CN 200980146533.8—Notice of Allowance dated Feb. 25, 2014, 2 pages.
CN 200980146533.8—Response to 1st Office Action dated Dec. 5, 2012 filed Apr. 9, 2013, 14 pages with translation included.
CN 200980146533.8—Response to 2nd Office Action dated Aug. 19, 2013 filed Oct. 21, 2013, 11 pages with translation included.
CN 201480058955.0—First Office Action dated Feb. 28, 2017, 9 pages.
CN 201480058955.0—Notice of Allowance dated Sep. 8, 2017, 4 pages.
CN 201480058955.0—Response to First Office Action dated Feb. 28, 2017 filed Jul. 14, 2017, 15 pages.
EP 09828054.8—1st Office Action dated Jan. 23, 2013, 4 pages.
EP 09828054.8—Extended EP Search Report dated Apr. 19, 2012, 8 pgs.
EP 09828054.8—Notice of Allowance dated Jul. 15, 2013, 75 pages.
EP 09828054.8—Response to Extended EP Search Report dated Apr. 19, 2012 filed Nov. 16, 2012, 30 pages.
EP 09828054.8—Response to first Office Action dated Jan. 23, 2013 filed May 16, 2013, 11 pages.
EP 14858416.2—Extended European Search Report dated Jun. 22, 2017, 16 pages.
EP 14858416.2—Response to Extended European Search Report dated Jun. 22, 2017 filed Jan. 19, 2018, 24 pages.
JP 2011537520—1st Office Action dated Dec. 20, 2012, 8 pages.
JP 2011537520—2nd Office Action dated Oct. 10, 2013, 5 pages with translation included.
JP 2011537520—Notice of Allowance dated Jun. 5, 2014, 3 pages.
JP 2011537520—Response to 1st Office Action dated Dec. 20, 2012 filed Apr. 22, 2013, 16 pages with translation included.
JP 2011537520—Response to 2nd Office Action dated Oct. 10, 2013 filed Apr. 10, 2014, 13 pages.
JP 2014080934—1st Office Action dated Jan. 6, 2015, 6 pages with translation included.
JP 2015076854—1st Office Action dated Jan. 9, 2016, 5 pages.
JP 2015076854—Notice of Allowance dated Sep. 27, 2016, 3 pages.
JP 2015076854—Response to first Office Action dated Jan. 9, 2016 filed Apr. 25, 2016, 7 pages.
JP 2016-230681—Notice of Allowance dated Sep. 26, 2017, 3 pages.
JP 2016-230681—Request for Examination and voluntary amendment filed Dec. 28, 2016, 17 pages.
JP 2016-526033—First Office Action dated Jan. 9, 2018, 7 pages.
JP 2016-526033—Request for Examination and Voluntary Amendment filed Sep. 26, 2017, 32 pages.
JP 2016-526033—Response to First Office Action dated Jan. 9, 2018, as filed Mar. 29, 2018, 24 pages.
JP 2017-559683—1st Office Action dated Apr. 24, 2018, 5 pages.
PCT/US2009/064395—International Preliminary Report on Patentability dated Jun. 3, 2011, 9 pages.
PCT/US2009/064395—Search Report and Written Opinion dated Feb. 3, 2010, 14 pages.
PCT/US2014/063518—International Preliminary Report on Patentability dated May 3, 2016, 9 pages.
PCT/US2014/063518—International Search Report and Written Opinion dated Feb. 9, 2015; 15 pages.
PCT/US2016/032125—International Preliminary Report on Patentability dated Nov. 30, 2017, 5 pages.
PCT/US2016/032125—International Search Report and Written Opinion dated Aug. 25, 2016, 5 pages.
PCT/US2017/032467—International Preliminary Report on Patentability dated Nov. 20, 2018.

(56) References Cited

OTHER PUBLICATIONS

PCT/US2017/032467—International Search Report and Written Opinion dated Aug. 21, 2017, 17 pages.
U.S. Appl. No. 12/611,057—Notice of Allowance dated Nov. 5, 2012, 11 pages.
U.S. Appl. No. 12/611,057—Office Action dated Jun. 19, 2012, 22 pages.
U.S. Appl. No. 12/611,057—Response to Office Action dated Jun. 19, 2012 filed Oct. 18, 2012, 22 pages.
U.S. Appl. No. 12/611,057—Response to Restriction Requirement dated Apr. 28, 2012 filed May 24, 2012, 11 pages.
U.S. Appl. No. 12/611,057—Restriction Requirement dated Apr. 27, 2012, 11 pages.
U.S. Appl. No. 13/766,567—Notice of Allowance dated Jun. 22, 2015, 9 pages.
U.S. Appl. No. 13/766,567—Office Action dated Dec. 1, 2014, 10 pages.
U.S. Appl. No. 13/766,567—Office Action dated Mar. 12, 2014, 9 pages.
U.S. Appl. No. 13/766,567—Response to Office Action dated Dec. 1, 2014 filed Feb. 11, 2015, 8 pages.
U.S. Appl. No. 13/766,567—Response to Office Action dated Mar. 12, 2014 filed Sep. 4, 2014, 9 pages.
U.S. Appl. No. 13/766,567—Response to Restriction Requirement dated Nov. 19, 2013 filed Dec. 11, 2013, 6 pages.
CN 201780039970.4—First Office Action dated Dec. 3, 2020, 11 pages.
EP 14858416.2—First Office Action dated Jun. 27, 2018, 7 pages.
JP 2018-140150—Request for Examination and Voluntary Amendment filed Aug. 24, 2018, 23 pages.
U.S. Appl. No. 14/876,035—Final Office Action dated Jan. 4, 2019, 8 pages.
U.S. Appl. No. 14/876,035—Notice of Allowance dated Apr. 9, 2019, 8 pages.
CN 201780039970.4—First Office Action dated Dec. 3, 2020, 13 pages.
EP 17799918-2—Voluntary Amendments filed Jul. 23, 2019, 16 pages.
EP 17799918-2—Extended European Search Report dated Jan. 23, 2020, 10 pages.
AU 2017267476—Request for Exam and Amendment filed on Oct. 29, 2020, 17 pages.
JP 2018-561003—Request for Examination filed May 11, 2020, 12 pages.
JP 2018-561003—First Office Action dated May 25, 2021, 17 pages.
U.S. Appl. No. 15/593,790—Notice of Allowance dated Nov. 23, 2018, 7 pages.
CN 201780039970.4—Certificate of Grant dated Aug. 11, 2021, 4 pages.
AU 2017267476—First Office Action dated Jun. 3, 2021, 4 pages.
KR 10-2018-7036573—First Office Action dated May 25, 2021, 17 pages.
EP 14858416.2—Second Office Action dated May 18, 2020, 11 pages.
EP 14858416.2—Communication Under Rule 71(3) EPC dated Oct. 26, 2020, 38 pages.
U.S. Appl. No. 15/211,365—Notice of Allowance dated Jun. 13, 2018, 43 pages.
CN 201711084674.4—First Office Action dated Sep. 26, 2019, 19 pages.
CN 201711084674.4—Second Office Action dated Mar. 16, 2021, 16 pages.
JP 2018-140150—First Office Action dated Sep. 24, 2019, 8 pages.
JP 2018-140150—Second Office Action dated Jun. 2, 2020, 5 pages.
CN 201680024610.2—First Office Action dated Aug. 1, 2018, 8 pages.
JP 2017-559683—First Office Action dated Apr. 24, 2018, 4 pages.
EP 16796979.9—First Office Action dated Jan. 25, 2019, 9 pages.

* cited by examiner

United States Patent US 11,266,456 B2

CRYOGENIC ABLATION SYSTEM WITH ROTATABLE AND TRANSLATABLE CATHETER

CROSS-REFERENCE TO OTHER APPLICATIONS

This application is a continuation of co-pending U.S. patent application Ser. No. 15/593,790 filed on 12 May 2017, which application claims the benefit of U.S. provisional patent application 62/339,611, filed 20 May 2016, the disclosures of which are incorporated by reference.

This application is related to the following: (1) U.S. patent application Ser. No. 14/530,288, now U.S. Pat. No. 9,050,073; and (2) U.S. patent application Ser. No. 14/714,101, filed 15 May 2015, now U.S. Pat. No. 9,414,878, the disclosures of which are incorporated by reference.

BACKGROUND

The subject matter discussed in this section should not be assumed to be prior art merely as a result of its mention in this section. Similarly, a problem mentioned in this section or associated with the subject matter provided as background should not be assumed to have been previously recognized in the prior art. The subject matter in this section merely represents different approaches, which in and of themselves may also correspond to implementations of the claimed technology.

Throughout the human body there are lumens, such as the esophagus and colon, which may have components which may become metaplastic or neoplastic. Often, it is desirable to remove or destroy these unwanted tissues. One of these cases where tissue removal and/or ablation are desirable is Barrett's Esophagus, which is a pre-cancerous condition of the esophagus typically often associated with gastric reflux disease (GERD). Although GERD can be medically controlled, Barrett's Esophagus does not spontaneous resolve once the GERD has abated. However, it has been shown that if Barrett's Esophagus is ablated, the normal esophagus lining can be restored and therefore lower the risk of developing esophageal cancer.

A variety of techniques have been evaluated for ablation of this condition. These techniques include cryogenic ablation via a direct spray of liquid nitrogen. One challenge in treating these types of lesions with cryogenic ablation relates to delivery of sufficient refrigerant for ablation over a large lesion area.

BRIEF SUMMARY

A simplified summary is provided herein to help enable a basic or general understanding of various aspects of exemplary, non-limiting implementations that follow in the more detailed description and the accompanying drawings. This summary is not intended, however, as an extensive or exhaustive overview. Instead, the sole purpose of this summary is to present some concepts related to some exemplary non-limiting implementations in a simplified form as a prelude to the more detailed description of the various implementations that follow. Reference numerals are sometimes used to refer to elements of disclosed examples and not in a limiting sense.

An ablation assembly 10 includes a controller assembly 13 and a cryogenic ablation catheter 12. The controller assembly 13 comprises a handle assembly 14, a controller 50, and a user control assembly 15 coupled to the controller. The handle assembly comprises a connector receptacle 99. The cryogenic ablation catheter 12 comprises a catheter shaft 16, a connector 22, an expandable and collapsible balloon 24, and a delivery tube assembly. The catheter shaft 16 has proximal and distal ends and a catheter shaft lumen extending between the proximal and distal ends. The connector 22 is at the proximal end of the catheter shaft and is selectively connected to a first connector element of the handle assembly. The connector comprises a connector body 23 and a plug 38, also called second connector element 38. The expandable and collapsible balloon 24 is mounted to the distal end of the catheter shaft, the balloon having an inner surface defining a balloon interior. A delivery tube assembly comprises a delivery tube 30 and a diffuser 36. The delivery tube 30 is housed within the catheter shaft for axial and rotational movement relative to the catheter shaft. The delivery tube has a proximal end connected to the plug. The diffuser 36 is within the balloon and is fluidly coupled to the delivery tube. The handle assembly comprises a handle assembly body 90, the controller connector 100, a traveler 110, a refrigerant fluid source 96, the linear driver 104, 108, 106, and a rotary motion driver 120, 124, 122. The controller connector 100 is mounted to the handle assembly body and defines the first connector element, the connector body being securable to the controller connector. The traveler 110 is movably mounted to the handle assembly body for movement along an axis towards and away from the controller connector, the plug being securable to the traveler for axial movement therewith. The refrigerant fluid source 96 is selectively fluidly coupled to a delivery line 118 by the refrigerant controller 130, 128. The delivery line has a distal end connected to the traveler, whereby the refrigerant delivery source can be fluidly coupled to the delivery tube at the plug/second connector element. The linear driver 104, 108, 106 is operably coupled to the traveler for moving the traveler along the axis. The rotary motion driver 120, 124, 122 is operably coupled to the plug for selective rotation of the plug and the proximal end of the delivery tube therewith about the axis. The user control assembly is operably coupled to the refrigerant controller, the linear driver and the rotary motion driver. The user control assembly includes user inputs permitting the user to actuate the refrigerant controller, the linear driver and the rotary motion driver. Whereby the user can control the rotation and translation of the diffuser within the balloon to direct refrigerant outwardly in a desired pattern towards the inner surface of the balloon according to, for example, the size and location of the treatment site.

Examples of the ablation assembly can include one or more the following. The user control assembly 15, also called a foot pedal assembly 15, spaced apart from the handle assembly 14 and connected to the handle assembly by a line 17, the foot pedal assembly comprising foot actuated input devices. The foot pedal assembly 15 can comprise a left movement foot pedal 140, a right movement foot pedal 142 and movement mode button 144 by which the user can change the mode of operation of the left and right movement foot pedals to actuate either the linear driver or the rotary motion driver. The foot pedal assembly 15 can also include a refrigerant delivery foot pedal 132 by which a user can actuate the refrigerant controller to supply refrigerant to the balloon 24 and a balloon deflation button 134.

Examples of the ablation assembly can also include one or more the following. The traveler can be positionable along the axis at a first, eject position, a second, load position, and at a range of third, operational positions, the first, eject position being closest to the controller connector, the second, load position being between the first, eject positions and the third, operational positions. The ablation assembly can further comprise: means for automatically securing the connector body 23 to the controller connector 100 and the plug 38, also called the second connector element 38, to the traveler 110 when the connector is inserted into the first connector element and the traveler is at the second, load position; and means for automatically releasing the connector body from the controller connector and the plug from the traveler when the traveler is at the first, eject position to permit removal of the connector from the handle assembly body.

Examples of the ablation assembly can also include one or more the following. The refrigerant fluid source 96 can include a removable and replaceable refrigerant cartridge having a tip 178 through which refrigerant can pass to the delivery line 118 via the refrigerant controller 130, 128 when the refrigerant fluid source is at an operational position. The handle assembly body 90 can include a refrigerant venting chamber 180 and a pathway 182, 184, 186 fluidly connecting the interior of the refrigerant venting chamber to a region adjacent to the tip of the refrigerant cartridge when the refrigerant cartridge has been displaced from the operational position during removal of the refrigerant cartridge from the handle assembly body 90. Whereby residual liquid refrigerant from the refrigerant cartridge can flow into the refrigerant venting chamber for transformation into a refrigerant gas, the refrigerant venting chamber having an exit port 192 to permit the refrigerant gas to exit the refrigerant venting chamber. In some examples the exit port 192 opens into the handle assembly body 90, the handle assembly body having a plurality of exhaust ports 133, 135 opening into the ambient atmosphere.

In some examples the ablation assembly can include one or more the following. The traveler can be positionable along the axis at a first, eject position, a second, load position, in the range of third, operational positions, the first, eject position being closest to the controller connector, the second, load position being between the first, eject positions and the third, operational positions. The rotary motion driver can include a rotation motor 120, a drive gear 126 and gear teeth 85. Rotation motor 120 can be drivingly connected to a non-cylindrical rotation shaft 122. The drive gear 126 can be mounted to traveler 110 for axial movement with the traveler, the drive gear also slideably mounted to the rotation shaft. Whereby rotation of the rotation shaft causes the drive gear to rotate and axial movement of the traveler causes the drive gear to slide along the rotation shaft. The gear teeth 85 can be formed on the plug 38 and rotatably coupled to the drive gear when the traveler is in either the second, load position or the third, operational position, so that rotation of the drive gear causes the plug 38 to rotate. The linear driver can include a linear drive motor 104 connected to a threaded shaft 106 by a threaded shaft coupler 108, the threaded shaft threadably engaging the traveler 110 so that rotation of the threaded shaft causes the traveler to move axially.

In some additional examples, the ablation assembly can include one or more the following. The connector 22 can include an RFID device 198 containing information relating to the cryogenic ablation catheter 12, and handle assembly can include an RFID reader 200 used to obtain information from the RFID device. The RFID reader 200 can be mounted to the controller connector 100, the connector body 23 being made of PEEK (polyetheretherketone) to enhance the communication between the RFID reader and the RFID device 198. The controller assembly can include a controller 50, and the user control assembly can be operably coupled to the refrigerant controller, the linear driver, and the rotary motion driver through the controller. A pressure detecting lumen 32 can extend along the catheter shaft 16 fluidly coupling the balloon interior and the connector body 23, and the controller 50 can be configured to use input received from a pressure transducer 143 operably coupled to the pressure detecting lumen 32 through the connector body 23 to detect a pressure within the balloon 24. The controller 50 can be configured to monitor the pressure and temperature of the refrigerant fluid source 96, whereby the status of the refrigerant can be monitored. The first connector element can include a connector receptacle and the second connector element can include a plug.

An example of a second ablation assembly includes a handle assembly 14, a catheter 12, and a connector locking assembly. The catheter 12 includes a catheter shaft 16 having distal and proximal ends, a balloon 24 at the distal end of the catheter shaft, a connector 22 at the proximal end of the catheter shaft, and a delivery tube 30 extending between the balloon and the proximal end of the catheter shaft. The connector includes a connector body 23 secured to the proximal end of the catheter shaft and a plug 38 secured to the delivery tube, the plug and delivery tube therewith movable axially and rotationally relative to the catheter shaft. The handle includes an open portion for receipt of the plug and at least a portion of the connector body. The connector locking assembly includes connector body and plug clocking slots. The connector body locking slot 74 is formed in and circumscribes the connector body 23. The plug locking slot 84 is formed in and circumscribes the plug 38. The connector locking assembly also includes connector body and plug locking elements. The connector body locking element 160 is mounted to the handle and positioned to engage the connector body locking slot 74 when the connector 22 is in a load state. The plug locking element 152, 154 is mounted to the handle and positioned to simultaneously engage the plug locking slot 84 when the connector is in the load state, thereby simultaneously automatically connecting the plug 38 and the connector body 23 to the handle to place the connector in a load state prior to use. The connector body locking element 160 it is mounted to the handle and positioned to disengage from the body locking slot when the connector is being placed in an eject state. The plug locking element 152, 154 is mounted to the handle and positioned to disengage from the body locking slot when the connector is in the eject state, thereby automatically releasing the connector body 23 and thereafter the plug 38 from the handle to permit the connector to be removed from the handle.

Some examples of the second ablation assembly can include one or more the following. The connector body locking element can include a first spring 160 and the plug locking element can include a second spring 152, 154. The connector body 23 can include a tapered surface 162 engageable by the first spring 160 when the connector is placed into the load state, and the plug 38 can include a tapered surface 156 engageable by the second spring 152, 154 when the connector is placed into the load state. The connector locking assembly can include a ramp 170 engageable by the first spring 160 when the connector is placed into the eject state; and can include the connector locking assembly comprises a ramp 174 engageable by the second spring 152, 154 when the connector is placed into the load state.

An example of a third ablation assembly includes a handle assembly 14, a catheter 12 and a connector locking assembly. The catheter 12 includes: a catheter shaft 16 having distal and proximal ends, a balloon 24 at the distal end of the catheter shaft, a connector 22 at the proximal end of the catheter shaft, and a delivery tube 30 extending between the balloon and the proximal end of the catheter shaft. The connector includes a connector body 23 secured to the proximal end of the catheter shaft and a plug 38 secured to the delivery tube, the plug and delivery tube therewith movable axially and rotationally relative to the catheter shaft. The handle includes an open portion for receipt of the plug and at least a portion of the connector body. The connector locking assembly includes: means for simultaneously automatically connecting the plug 38 (84, 152, 154, 156, 158) and the connector body 23 (160, 174, 162) to the handle to place the connector in a load state prior to use, and means for automatically releasing the connector body (74, 110, 160, 170) and thereafter the plug (84, 110, 152, 154, 174) from the handle to place the connector in an eject state to permit the connector to be removed from the handle.

An example of a handle assembly for use with a cryogenic ablation assembly 10 includes a handle body 90, having anterior, and a refrigerant fluid source 96 within the interior. The refrigerant fluid source 96 includes a refrigerant discharge portion 178. The refrigerant fluid source includes a removable and replaceable refrigerant cartridge 96 from which refrigerant can pass for use by the cryogenic ablation assembly 10 when the refrigerant fluid source is at an operational position. The handle body 90 includes a refrigerant venting chamber 180 and a pathway 182, 184, 186 fluidly connecting the interior of the refrigerant venting chamber to a region adjacent to the refrigerant discharge portion of the refrigerant cartridge when the refrigerant cartridge has been displaced from the operational position during removal of the refrigerant cartridge from the handle body 90. The handle body includes an exhaust port 133, 135 opening into the ambient atmosphere. Residual liquid refrigerant from the refrigerant cartridge can flow into the refrigerant venting chamber for transformation into a refrigerant gas. The refrigerant venting chamber has an exit port 192 to permit the refrigerant gas to exit the refrigerant venting chamber and into a region external of the refrigerant venting chamber 180 and within the handle body 90, for passage through the exhaust port to the ambient atmosphere.

Examples of the handle assembly can include one or more the following. The refrigerant venting chamber 180 can be filled with a material with an entrance path 188 and an exit path 190 formed in the material, the entrance path connected to the pathway and the exit path 190 terminating at the exit port 192. Whereby under a reduced pressure within the refrigerant venting chamber 180, the liquid refrigerant can be absorbed by the foam material and transformed into a gas for collection within the exit path 190, passage through exit port 192 into said region external of the refrigerant venting chamber 180 and within the handle body 90. A thermal insulation material 194 can be used between the refrigerant venting chamber 180 and the handle body 90, and spacers 196 can be used between the thermal insulation material 194 and the handle body 90.

An example of a catheter identification structure, for a cryogenic ablation assembly 10 of the type including a handle assembly 14 and a catheter assembly, the catheter 12 including a catheter shaft 16 having distal and proximal ends, a connector 22 at the proximal end of the catheter shaft, and a connector 22, the handle assembly 14 including an open portion for receipt of at least a portion of the connector, the catheter identification structure including an RFID device 198 and an RFID reader 200. The RFID device 198 is carried by the connector 22 and contains information relating to the catheter 12. The RFID reader 200 is carried by the handle assembly and is used to obtain information from the RFID device.

In some examples of the catheter identification structure, the connector 22 includes a connector body 23 made of PEEK to enhance the communication between the RFID reader 200 and the RFID device 198.

Other features, aspects and advantages of the technology disclosed can be seen on review the drawings, the detailed description, and the claims which follow.

BRIEF DESCRIPTION OF THE DRAWINGS

The included drawings are for illustrative purposes and serve only to provide examples of possible structures and process operations for one or more implementations of this disclosure. These drawings in no way limit any changes in form and detail that may be made by one skilled in the art without departing from the spirit and scope of this disclosure. A more complete understanding of the subject matter may be derived by referring to the detailed description and claims when considered in conjunction with the following figures, wherein like reference numbers refer to similar elements throughout the figures.

DESCRIPTION

Figure 1:
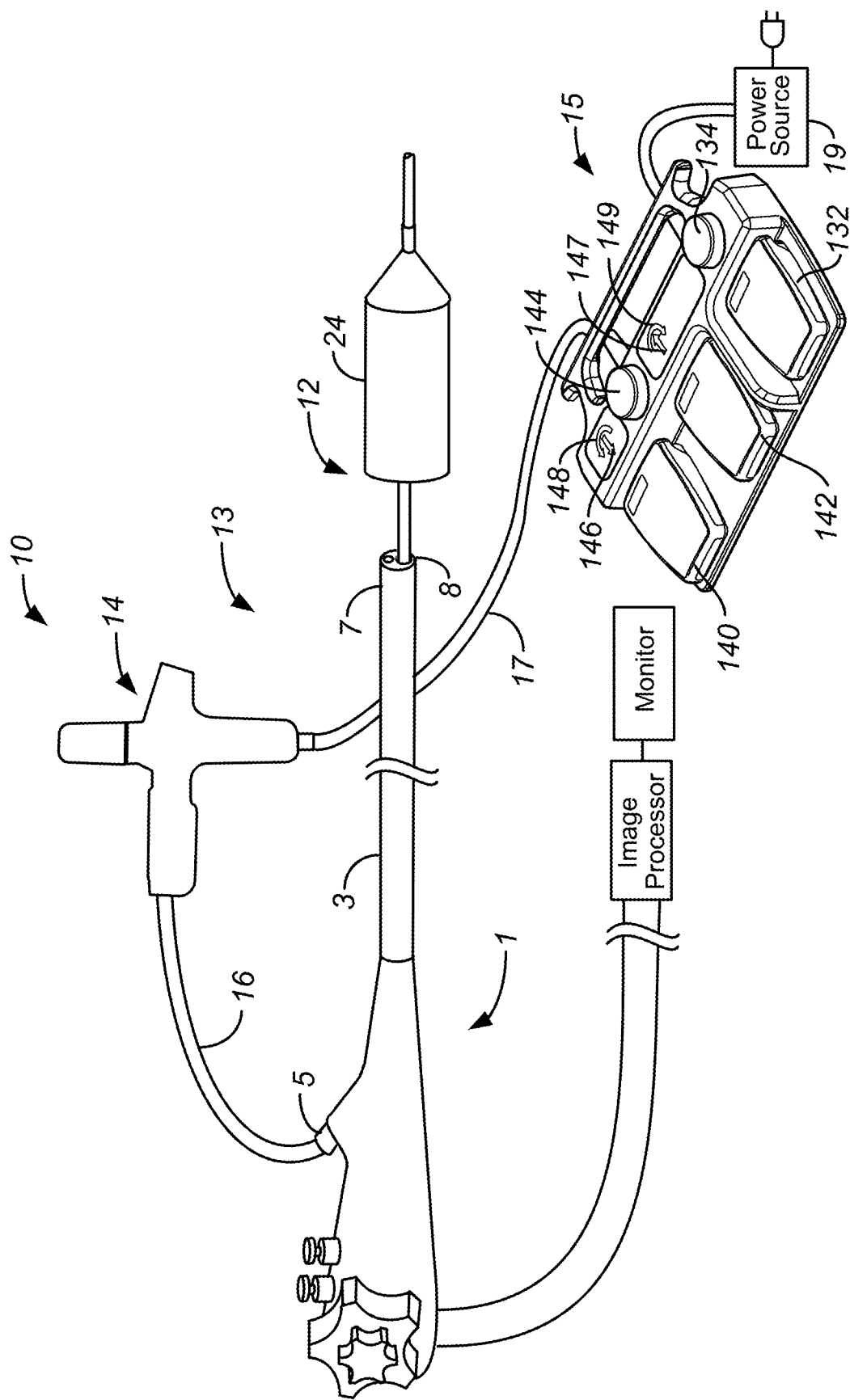
FIG. 1 is a simplified schematic overall view of an example of an ablation system including a cryogenic balloon ablation assembly and an endoscope.

The following description will typically be with reference to specific structural embodiments and methods. It is to be understood that there is no intention to-be limited to the specifically disclosed embodiments and methods but that other features, elements, methods and embodiments may be used for implementations of this disclosure. Preferred embodiments are described to illustrate the technology disclosed, not to limit its scope, which is defined by the claims. Those of ordinary skill in the art will recognize a variety of equivalent variations on the description that follows. Unless otherwise stated, in this application specified relationships, such as parallel to, aligned with, or in the same plane as, mean that the specified relationships are within limitations of manufacturing processes and within manufacturing variations. When components are described as being coupled, connected, being in contact or contacting one another, they need not be physically directly touching one another unless specifically described as such. Like elements in various embodiments are commonly referred to with like reference numerals.

An embodiment of an ablation system with improved refrigerant delivery area is shown in FIG. 1 and comprises an endoscope 1 and a cryogenic balloon ablation assembly 10. The endoscope 1 may be conventional and include an endoscopic tube 3 having proximal and distal ends 5, 7 defining a channel 8 extending between the proximal and distal ends.

In embodiments, an ablation assembly 10 comprises a cryogenic ablation catheter 12 and a controller assembly 13. Controller assembly 13 includes a handle assembly 14 and a foot pedal assembly 15 connected to handle assembly 14 by a power and control line 17. Power is supplied to controller assembly 13 by a power source 19 connected to foot pedal assembly 15. Ablation catheter 12 includes a catheter shaft 16 mounted to and extending from handle assembly 14.

Figure 2A:
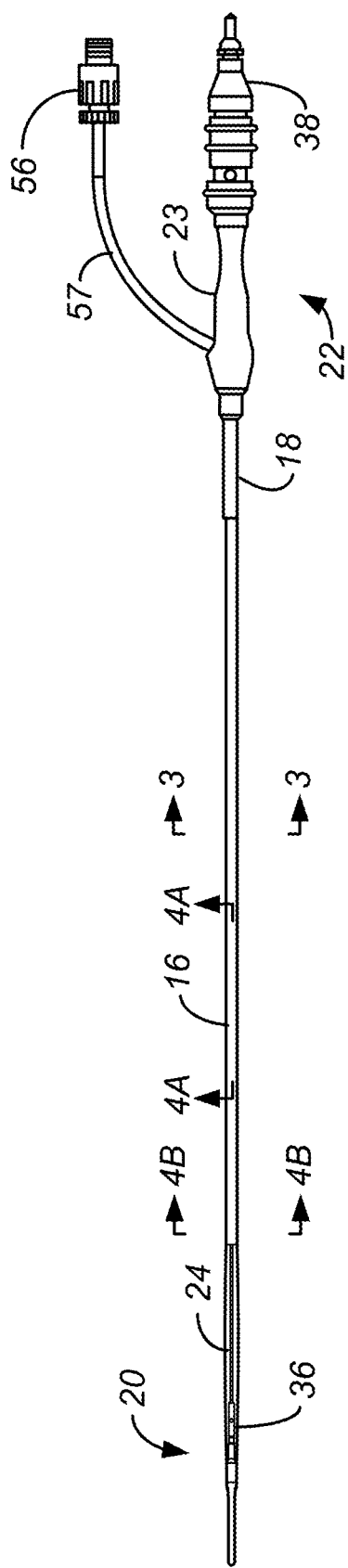
FIG. 2A illustrates an ablation catheter with a deflated balloon in tension.
Figure 2B:
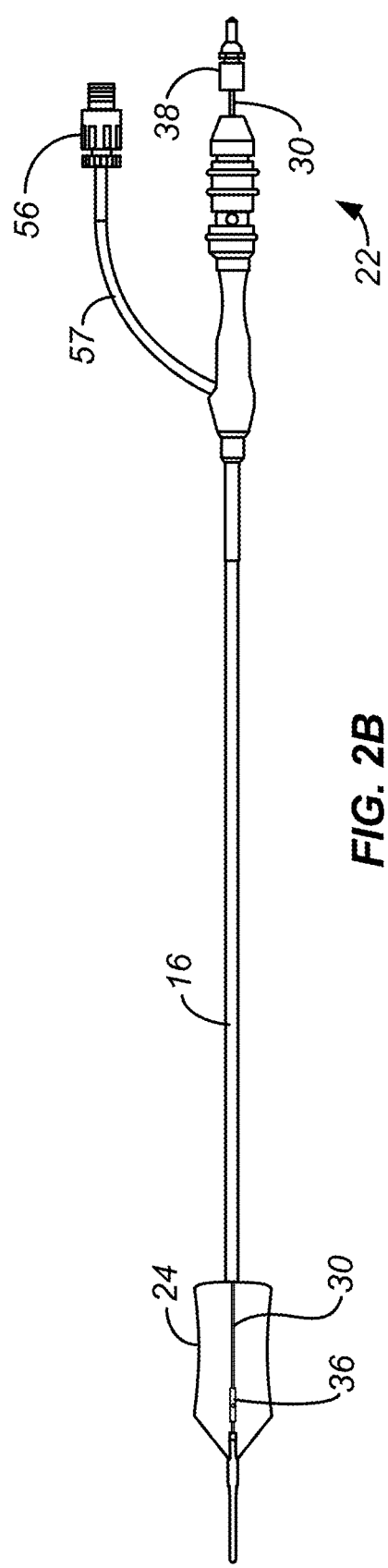
FIG. 2B illustrates an ablation catheter with an inflated balloon with the diffuser located at a distal region of the balloon.
Figure 2C:
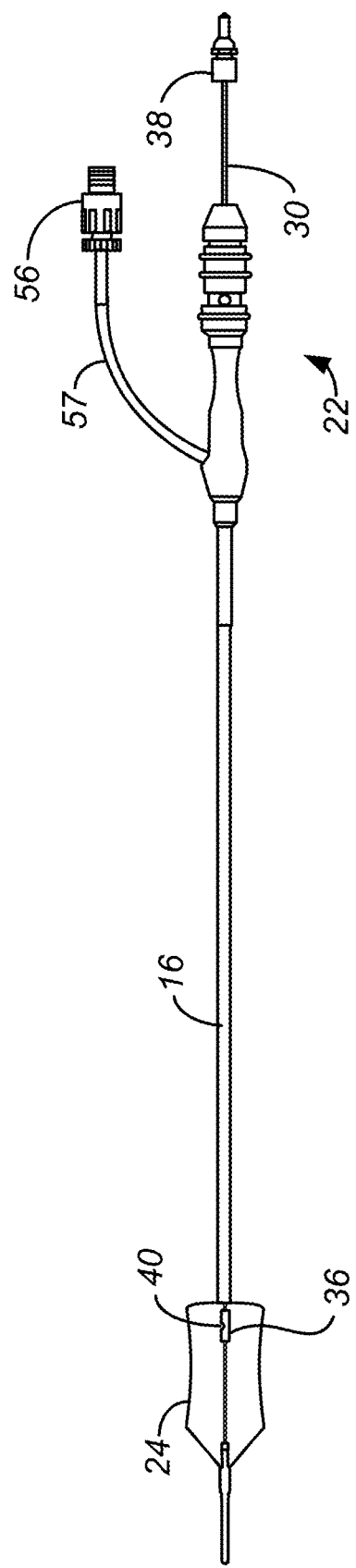
FIG. 2C illustrates an ablation catheter with an inflated balloon with the diffuser located in a proximal region of the balloon.

FIGS. 2A, 2B and 2C show an embodiment of a cryogenic ablation catheter in three states that will be discussed below. Catheter 12 includes a catheter shaft 16 having a proximal end 18 and a distal end 20. At the proximal end 18 is a connector 22 to be received in the handle assembly 14. Connector 22 includes a connector body 23 and a plug 38, also called the second connector element 38. At the distal end 20 is a balloon 24 that is inflatable by a refrigerant delivered from a refrigerant fluid source in the handle assembly 14 to a diffuser 36 located within the balloon. Diffuser 36 is secured to and is fluidly coupled to the distal end of a delivery tube 30. The diffuser 36 translates within the balloon through the axial movement of delivery tube 30 as is discussed in greater detail below. As illustrated in FIGS. 2B and 2C, translation of the diffuser 36 is caused by translation of a plug 38 affixed and fluidly coupled to the delivery tube 30 at the connector end of the catheter 12. As suggested by FIGS. 2B and 2C, plug 38 and delivery tube 30 and diffuser 36 therewith can be rotated to direct refrigerant in selected rotational directions and along selected rotational paths.

The catheter shaft 16 comprises a circular tube with a circular central lumen. The catheter shaft 16 may, for example, range from 120 cm to 350 cm in length and have an outer diameter ranging from, for example, 0.100" to 0.138". The proximal end of the catheter shaft 16 is affixed to the connector 22, and the distal end is affixed to the balloon 24.

Figure 3:
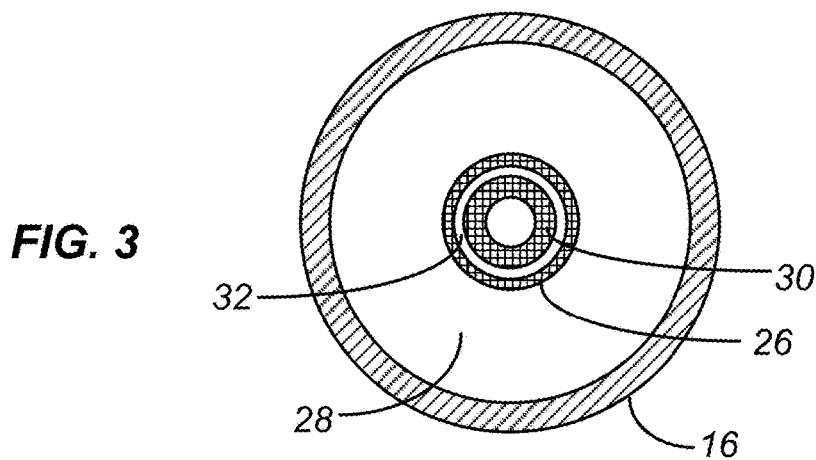
FIG. 3 is a cross-sectional view taken along line 3-3 of FIG. 2A.

FIG. 3 shows cross-section taken along line 3-3 of FIG. 2A. As shown, located within the catheter shaft 16 is a pressure detecting tube 26. The cavity between the inner wall of the catheter shaft and the outer wall of the pressure detecting tube defines an exhaust lumen 28 for the passage of gases from the balloon interior for discharge through the connector 22 and exhaust passageway 138 in controller connector 100, see FIG. 9A, which will be discussed in greater detail below. The pressure detecting tube 26 includes a circular central lumen containing a delivery tube 30. The cavity between the inner wall of the pressure detecting tube 26 and the outer wall of the delivery tube 30 defines a pressure detecting lumen 32 used to detect the pressure within the balloon 24.

Figure 4A:
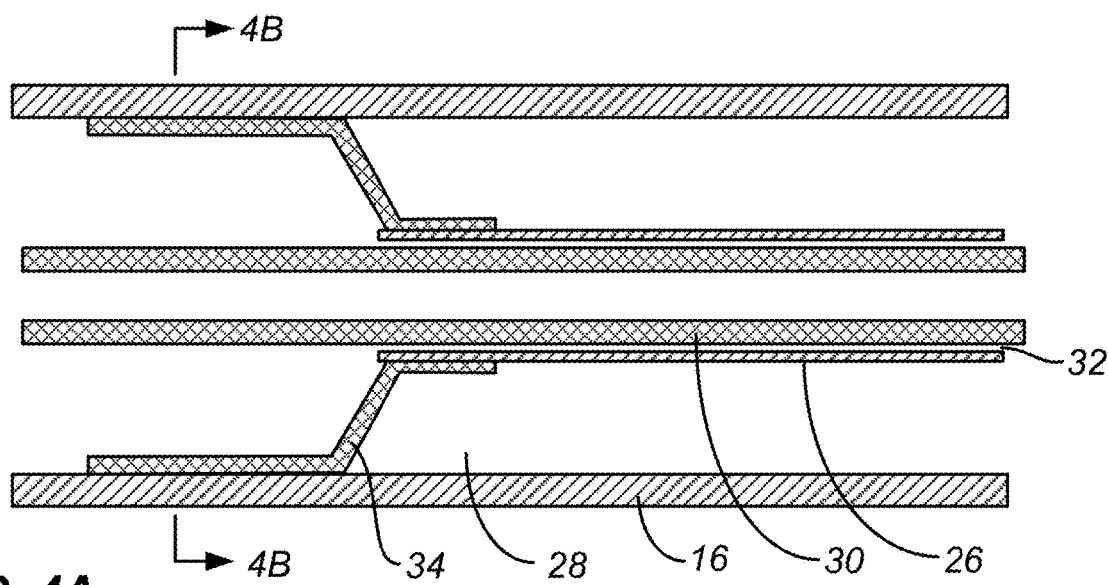
FIG. 4A is a cross-sectional view taken along line 4A-4A of FIG. 2A.
Figure 4B:
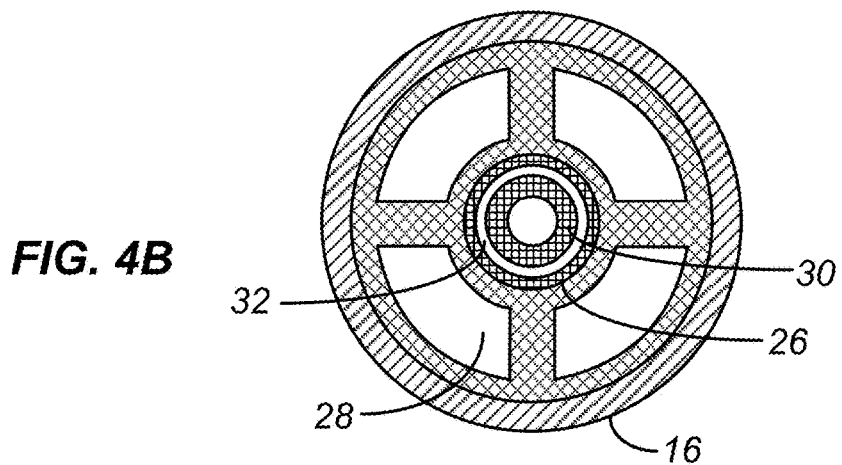
FIG. 4B is a cross-sectional view taken along line 4B-4B of FIG. 4A.

The pressure detecting tube 26 extends from near the balloon end of the catheter shaft 16 to the connector 22. The pressure detecting tube 26 is affixed to the catheter shaft 16 near the distal end 20 of the catheter shaft 16 to be concentric to the catheter shaft lumen. The affixing means includes a bracket 34 with minimal flow obstruction of the exhaust lumen as shown in FIGS. 4A and 4B. In embodiments, the bracket 34 is positioned a distance within the end of the catheter shaft 16 so that the a portion of the diffuser 36 may enter a portion of the catheter shaft 16 to allow delivery of refrigerant to portions of the balloon 24 located proximate to the distal end 20 of the catheter shaft 16.

As shown in FIG. 3, within the pressure detecting tube 26 is the delivery tube 30. The pressure detecting tube 26 is a guide for the delivery tube 30 ensuring consistent 1:1 translation and rotation of the delivery tube within the pressure detecting tube without backlash. To facilitate this, the interior surface of pressure detecting tube 26 is a low friction surface, such as can be achieved by coating the interior surface with PTFE and the exterior surface of the delivery tube 30 with PTFE. For example when the proximal or plug end of the delivery tube 30 is translated 4 mm and rotated 90°, then the diffuser end, and this diffuser 36, is also translated 4 mm and rotated 90°.

The delivery tube 30 extends from the plug 38 through the connector 22; through the pressure detecting tube 26, and to the diffuser 36. The delivery tube 30 is made of a strong, flexible tubing or tubing assembly. For example, the delivery tube 30 may be comprised of a tubing assembly including an outer nitinol tube, which is very elastic and does not plastically deform (e.g. kink) easily, and an inner thin-walled polyimide tube. The nitinol tubing provides structural support for the tubing assembly. The nitinol tubing provides the strength necessary to prevent buckling during axial translation of the delivery tube. Further, the nitinol tubing transmits torque well which allows for rotational movement of the delivery tube. In embodiments, the outer tube of a delivery tube assembly is a torque tube comprising stainless steel wires that undergo processes such as swaging, stretching, annealing, and then is wound around the inner tube to form a tubing assembly with good rotational and axial translation capabilities. The thin-walled polyimide inner tube is made with tight tolerances which allows for consist flow of refrigerant through the delivery tube. The delivery tube during use may experience internal pressures of 600 psi to 1200 psi and may be configured to have a wall thickness to withstand internal pressures up to 1500 psi. The delivery tube 30 translates within the pressure detecting tube 26 in response to movement of the plug/second connector element 38 relative to the connector 22.

FIG. 2A shows a state of the plug 38, wherein the plug 38 abuts the connector body 23 and the diffuser 36 is located at a position toward the distal end of the balloon 24, which is shown in a deflated state. FIG. 2B shows a state of the plug 38, wherein the plug 38 is located at a first intermediate position relative to the connector 22 and the diffuser 36 is located at a position in the balloon 24, shown in an inflated state. FIG. 2C shows a state of the plug 38, wherein the plug 38 is located at a proximal position and rotated 90° which changes the orientation of nozzle port 40 90°.

Figure 5A:
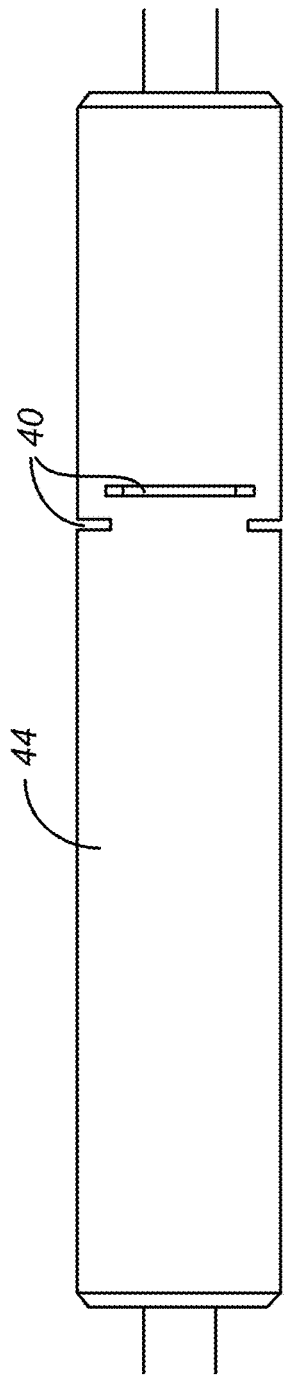
FIG. 5A illustrates an external view of the diffuser.
Figure 5B:
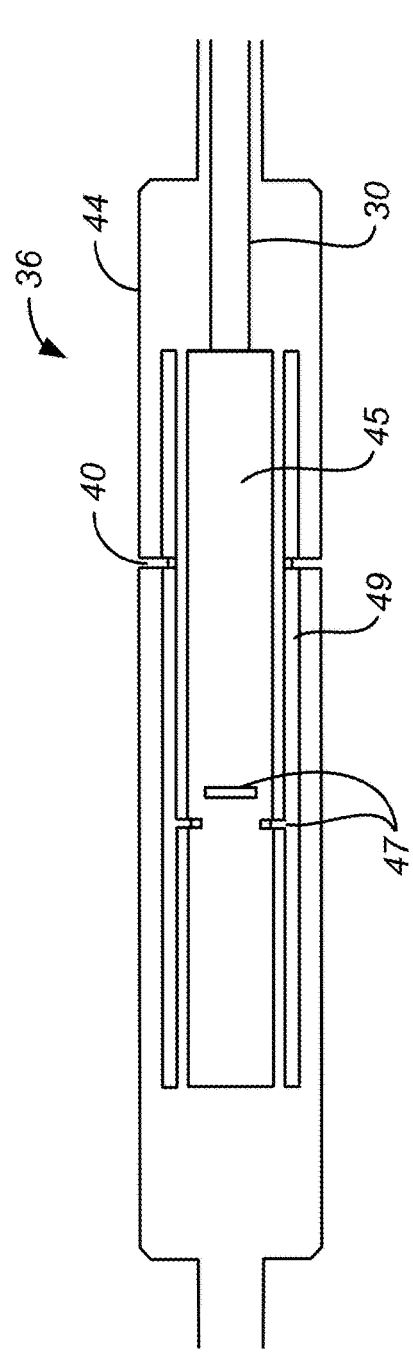
FIG. 5B is a cross section of the diffuser of FIG. 5A.
Figure 5C:
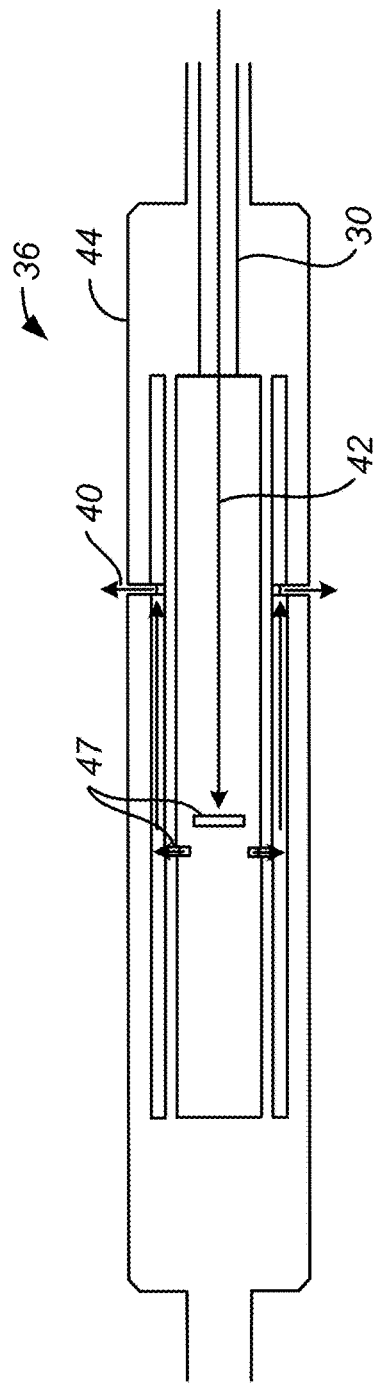
FIG. 5C is a cross section of the diffuser of FIG. 5A showing flow paths.

As shown in FIGS. 5A-5C, an alternative example of diffuser 36 is shown. The outer diffuser tube 44 of the diffuser 36 of FIGS. 5A-5C has a number of nozzle ports 40 arranged to direct refrigerant in a generally 360° rotary pattern in contrast with the limited rotary pattern created by the single nozzle port 40 shown in FIGS. 2A-2C and 6A-6D. The internal flow paths, discussed below with reference to FIGS. 5B and 5C, can be the same with both embodiments. The diffuser 36 comprises a hollow internal cavity 45 fluidly connected to the delivery tube 30. Cavity 45 has, in this example, four lateral passageways 47 extending from internal cavity 45 to a cylindrical cavity 49. Nozzle ports 40 extends through the outer surface of outer diffuser tube 44 and into cylindrical cavity 49 to permit refrigerant to flow as indicated by the refrigerant path 42 in FIG. 5C. This allows refrigerant supplied from a refrigerant fluid source in the handle assembly to be sprayed on the interior wall of the balloon 24. The nozzle ports 40 may be comprised of one or more slits located around the outer diffuser tube 44. The slits may be stacked in multiple rows to allow openings in the wall at all radial position, for example in embodiments where spray is to be delivered 360 degrees. In embodiments the desired delivery angle of the spray may be less than 360, for example 45 degrees, 90 degrees or 180 degrees. In these embodiments the nozzle ports 40 will be sized and positioned to deliver the desired angle of spray. In embodiments the nozzle ports 40 includes slits with a preferred height of 4 thousandths of an inch, but may range from 0.001" to 0.010". The path 42, as shown in FIG. 5C, is configured to allow for even distribution of refrigerant by the point the refrigerant is at the nozzle port end of the diffuser 36 so that the pressure is equal radially around the inner cavity. The single, circular nozzle port 40 shown in FIGS. 6A-6D may have a diameter of about 0.020" to 0.060", typically about 0.040". Additionally, the single port shape is not limited to a circle, but may be other shapes including ellipses and rectangles.

Figure 6A:
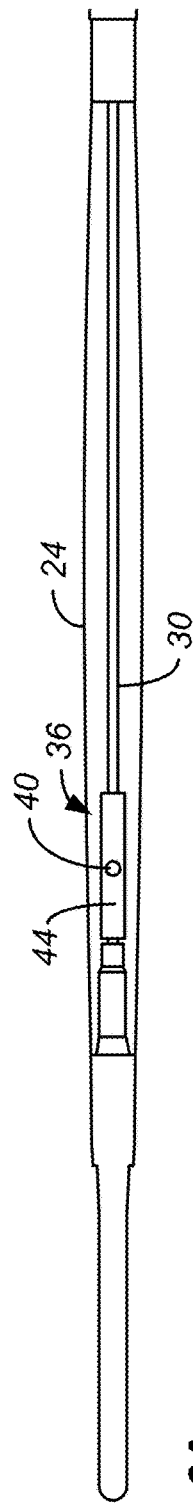
FIG. 6A is a detailed view of the balloon of FIG. 2A.
Figure 6B:
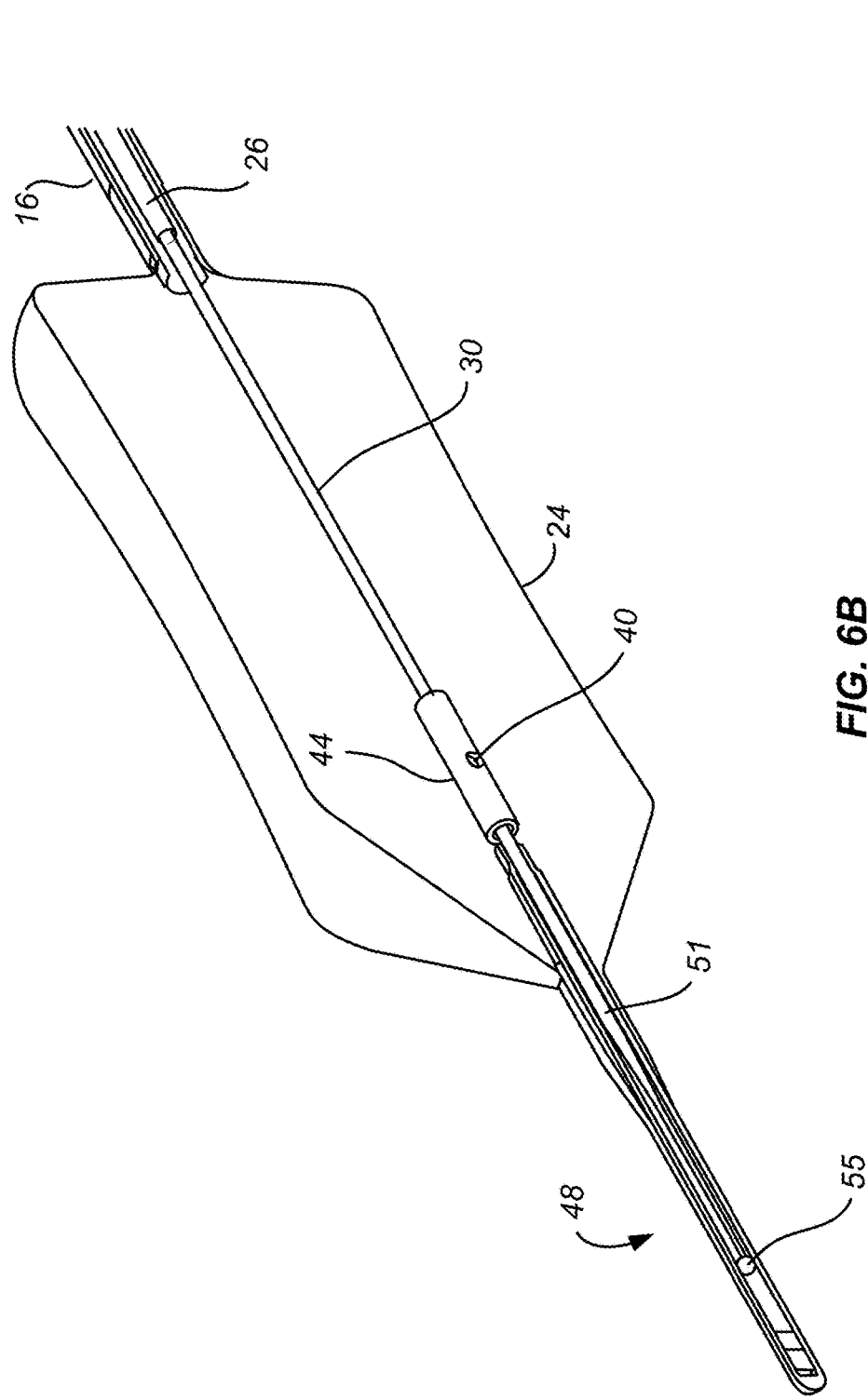
FIG. 6B is an isometric cross section view of the balloon of FIG. 2B.
Figure 6C:
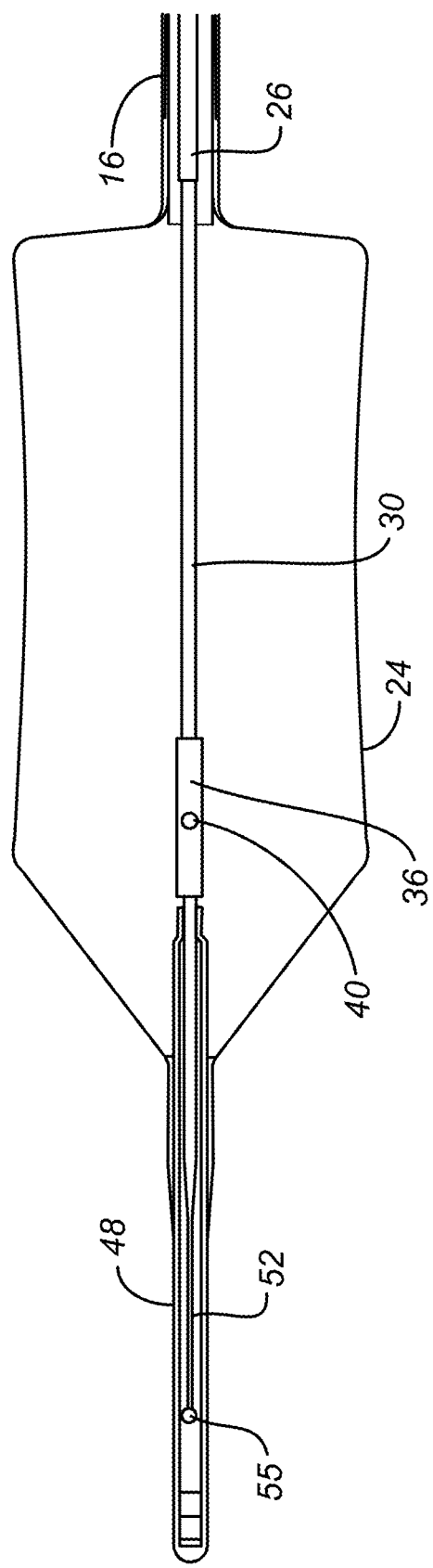
FIG. 6C is a cross section view of the balloon of FIG. 2B
Figure 6D:
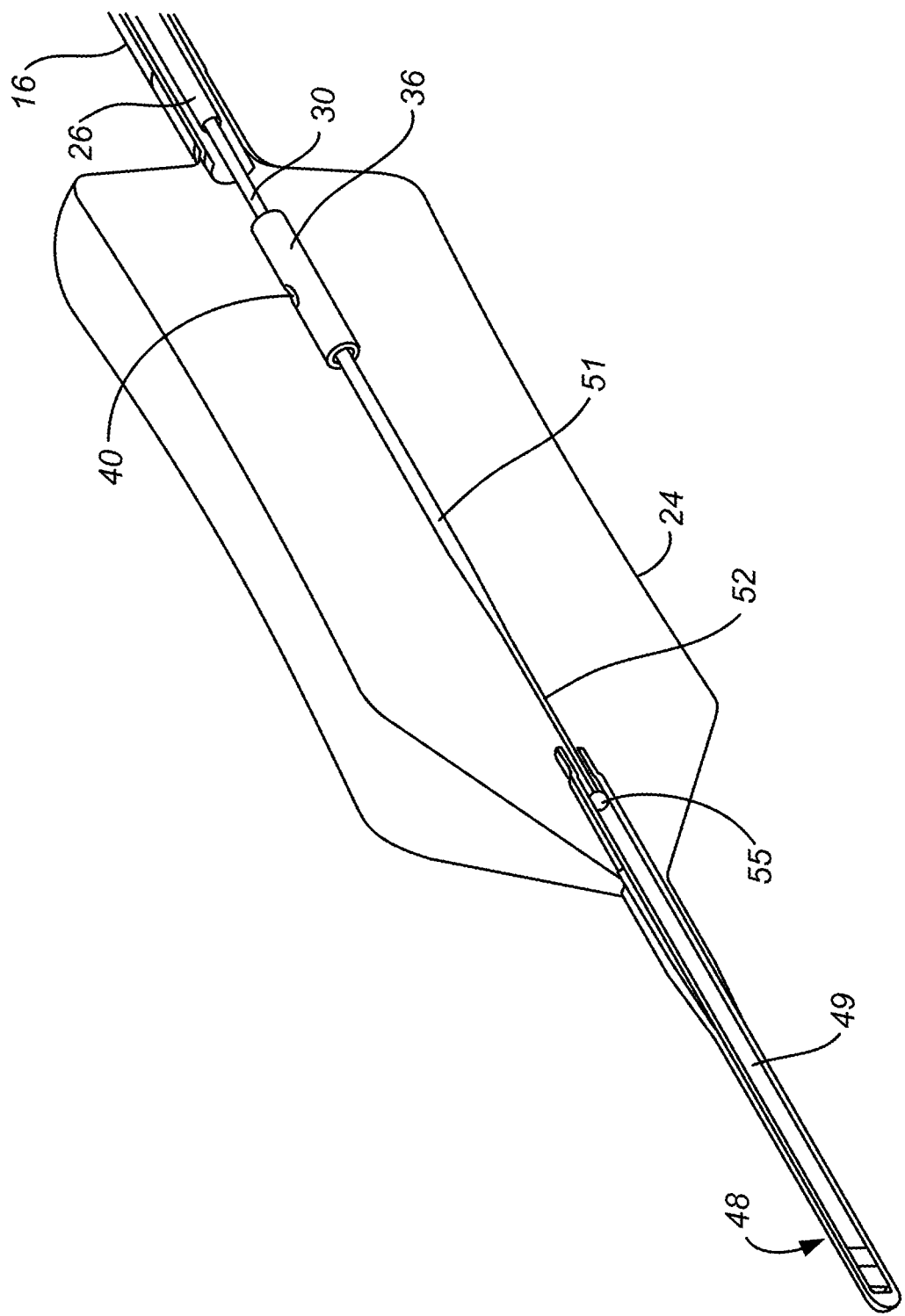
FIG. 6D is an isometric cross section view of the balloon of FIG. 2C

The balloon 24 is expandable and collapsible and is mounted to the distal end of the catheter shaft 16. FIG. 2A, shows a schematic of the balloon 24 in a deflated tension state, and FIGS. 2B and 2C, show the balloon 24 in an inflated state. Balloon 24 can be an elastic material, such as polyurethane, and can have an operating diameter in the range of 20 to 35 mm when inflated with less than 5 psi. Balloon 24 has an inner surface defining a balloon interior. In embodiments, the balloon 24 includes a tapered distal end secured to a flexible tip 48. During operation, refrigerant flows out through one or more nozzle ports 40 of the diffuser 36 generally radially outwardly to create refrigerant spray directed at a target site along the inner surface of the balloon 24. The target site of the inflated balloon is in contact with tissue and the delivery of refrigerant typically causes cryogenic ablation of tissue abutting target site of the balloon 24. In embodiments, the target site is larger than the area of spray delivery to the interior wall of the balloon 24 and the diffuser 36 translates along the length of the balloon and/or rotates within the balloon 24 while spraying to deliver refrigerant to the entire target site. The portion of the balloon capable of receiving refrigerant spray and shaped to be capable of contacting tissue is referred to as the working length of the balloon. In embodiments, the working length of the balloon 24 includes straight wall portions, as shown in FIGS. 2B and 2C. The balloon may further include tapered wall portions that usually do not contact tissue or receive refrigerant spray, as shown in FIGS. 2B and 2C. In embodiments, as shown in FIGS. 6B-6D, balloon 24 can have an hourglass shape with its smallest diameter, its waist, being smallest at a position spaced apart from either end. The balloon with this configuration can be selected because it facilitates properly locating and cryogenically ablating target tissue which extends inwardly within the hollow body structure being treated. Examples of such generally-extending tissue include tissue at the sphincter between the esophagus and stomach, and other tissue structures and shapes which are difficult to conform to using a balloon having, for example, a cylindrical outer surface. Therefore, during use a balloon can be selected having a non-cylindrical shape, such as an hourglass shape, which facilitates conforming the outer surface of the balloon to the tissue being treated. Balloons having shapes other than the moderate hourglass shape shown in FIGS. 6B-6D could be selected depending on the tissue being treated. For example, a balloon having two reduced diameter, waist portions could be chosen; the waist portions could have the same or different diameters. In embodiments the balloon 24 may include strain gauges used as input into a controller 50, which is discussed below.

The balloon 24 is shown in detail in FIGS. 6A, 6B, 6C and 6D. The flexible tip 48 is configured to assist in guiding the balloon end of the catheter while inserting the distal end of catheter 12 into a device, such as an endoscope, or into a bodily passage, such as an esophagus. For example, endoscopes commonly have a kink in the port at which the catheter is inserted. The flexible tip 48 is more flexible than the delivery tube 30 and prevents damage to the delivery tube 30 and balloon 24 during insertion of the catheter 12. For example, during initial insertion the flexible tip 48 may encounter an obstacle causing it to bend a substantial amount. This amount of bending may cause damage to the delivery tube 30 and render it inoperable. Therefore, the flexible tip 48 may act as a sacrificial bending point which may be caused to bend a large amount during initial insertion and not have an effect on the operability of the overall device because the delivery tube 30 will be able to pass by the obstacle with a more gentle bend because the flexible tip 48 is further along the path of insertion and able to guide the remainder of the catheter 12. Further, the flexible tip 48 may prevent damage to tissue in the body if during insertion the tip impacts tissue.

Flexible tip 48 includes a cylindrical cavity 49 slideably housing a delivery tube extension 51. Extension 51 is affixed to and extends from diffuser 36. Extension 51 is preferably made from a flexible material which resists kinking, such as nitinol. As shown best in FIG. 6D, extension 51 has a reduced diameter distal portion 52 to enhance the flexibility of the flexible, atraumatic tip 48. One way to create the reduced diameter portion 52 is through the use of centerless grinding. As shown in FIG. 6B, the flexible tip 48 includes a rounded end 55.

Translating the delivery tube 30 toward the flexible tip 48 can cause rounded and 55 to contact the distal end of flexible tip 48. This can cause the balloon 24 to stretch in tension to the collapsed, minimum diameter position shown in FIG. 2A. The uses and benefits of this stretched position will be discussed in detail below.

Figure 7A:
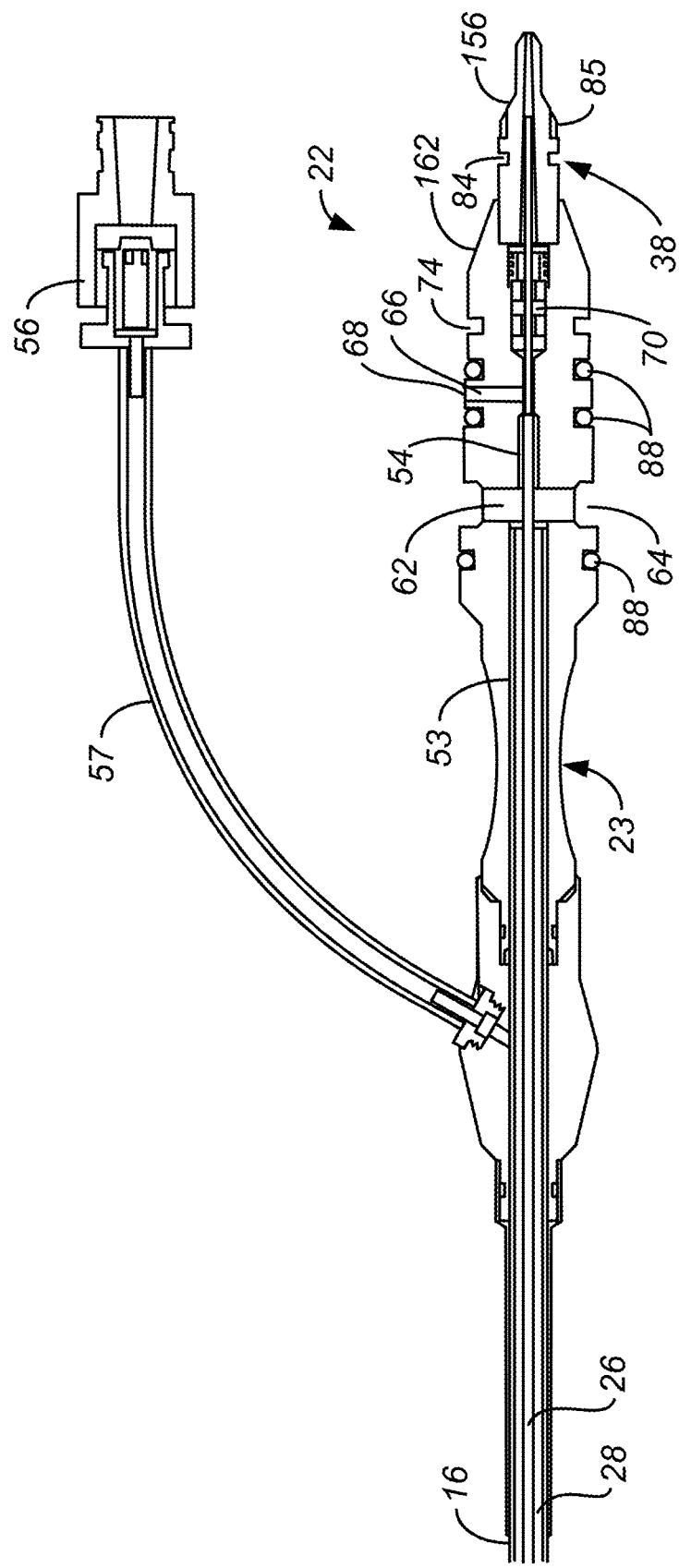
FIG. 7A illustrates an enlarged cross section view of the connector of FIG. 2A.
Figure 7B:
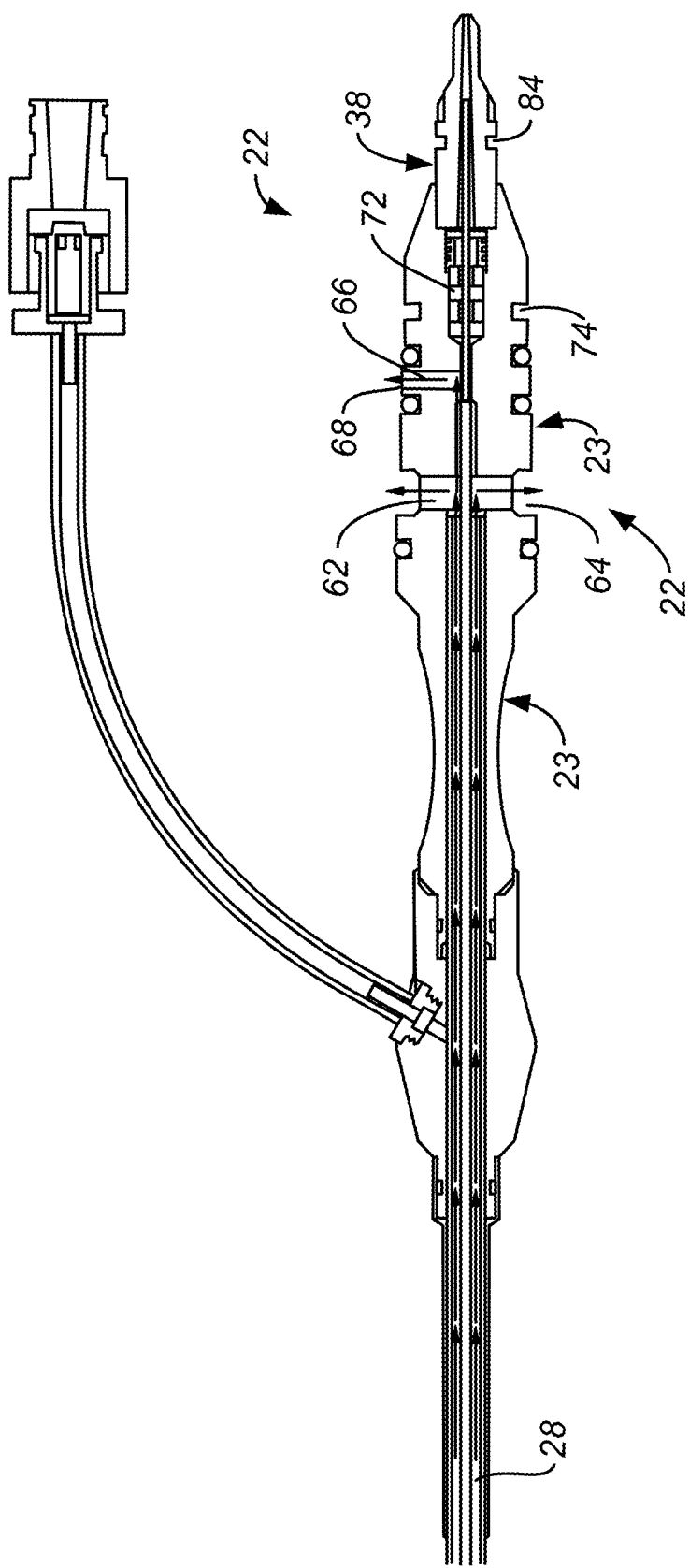
FIG. 7B illustrates the connector of FIG. 7A with flow lines.
Figure 7C:
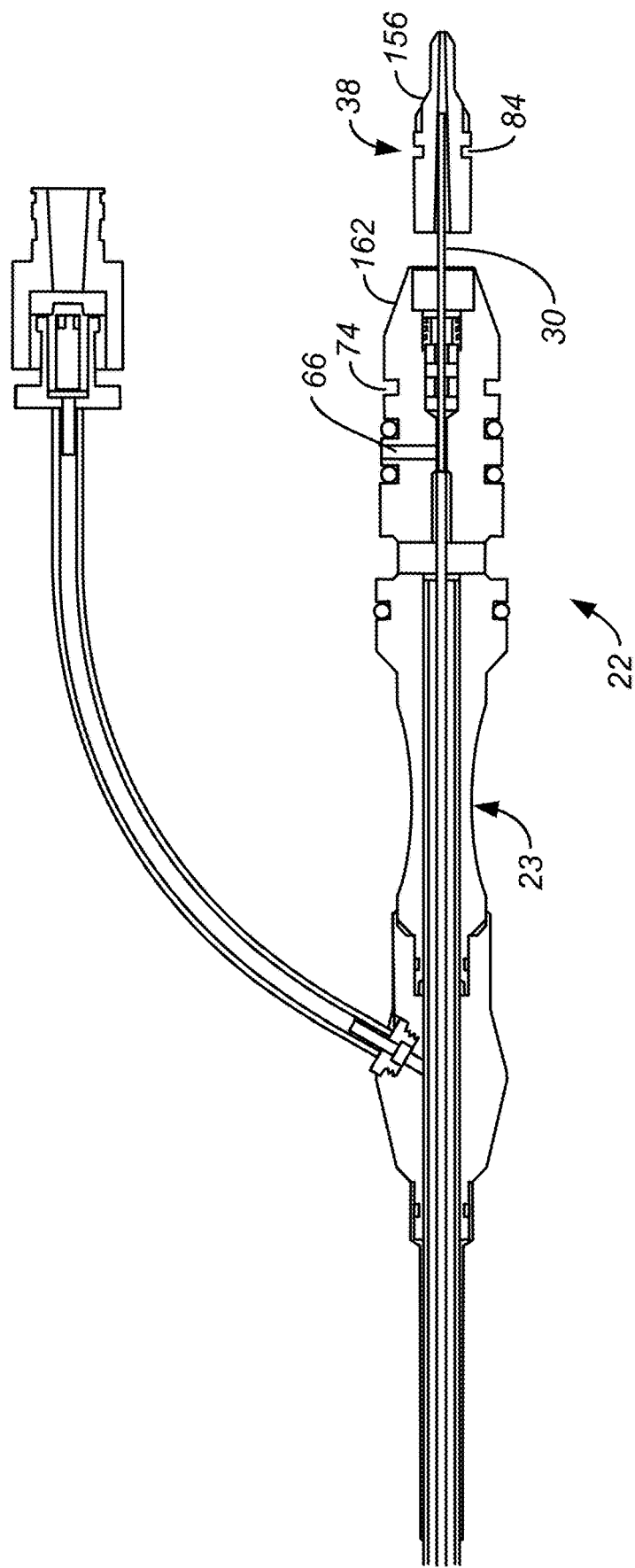
FIG. 7C illustrates an enlarged cross section view of the connector of FIG. 2B omitting the flow paths and showing the plug pulled distally in short distance.

FIGS. 7A-7C show the connector 22. The proximal end of the catheter shaft 16 and the pressure detecting tube 26 are affixed to positions 53 and 54 within the connector body 23. The connector 22 includes an exhaust passage 62 that fluidly couples the exhaust lumen 28 to a radial exhaust port 64 on the exterior of the connector body 23. The connector body 23 includes a pressure detecting passage 66 that fluidly couples the pressure detecting lumen 32, see FIGS. 4A and 4B, to a radial pressure detecting port 68 on the exterior of the connector body 23. The connector body 23 further includes a central passage 70 that the delivery tube 30 passes through between the pressure detecting passage 66 at the proximal end of the connecter 22. The delivery tube 30 is free to translate and rotate in the central passage 70 as well as pressure detecting tube 26. The central passage 70 is separated from the pressure detecting passage 66 by one or more seals 72 that allow the delivery tube 30 to translate and rotate in the pressure detecting tube 26 and pressure detecting passage 66 but prevents gas from the pressure detecting passage 66 being leaked out the central passage 70. Connector body 23 also includes a circumferentially extending body locking slot 74 used to secure connector body 23 to handle assembly 14. This will be described in more detail below.

Balloon 24 can be deflated by connecting the interior of the balloon 24 to the ambient atmosphere through exhaust lumen 28 for the passage of gas into handle assembly 14 and then out to the ambient atmosphere. Doing this does not necessarily fully collapse the balloon. A syringe, or other appropriate device, can be fluidly coupled to the exhaust lumen 28 within connector body 23 through a syringe coupler 56 connected to connector body 23 by tubing 57. Syringe coupler 56 includes a one-way valve which opens only when a syringe, or other vacuum/pressure application structure, is mounted to syringe coupler 56. In addition to removing gas from the balloon, a syringe can be used to expand the balloon, or expand and contract the balloon, such as during placement of the balloon.

Figure 7D:
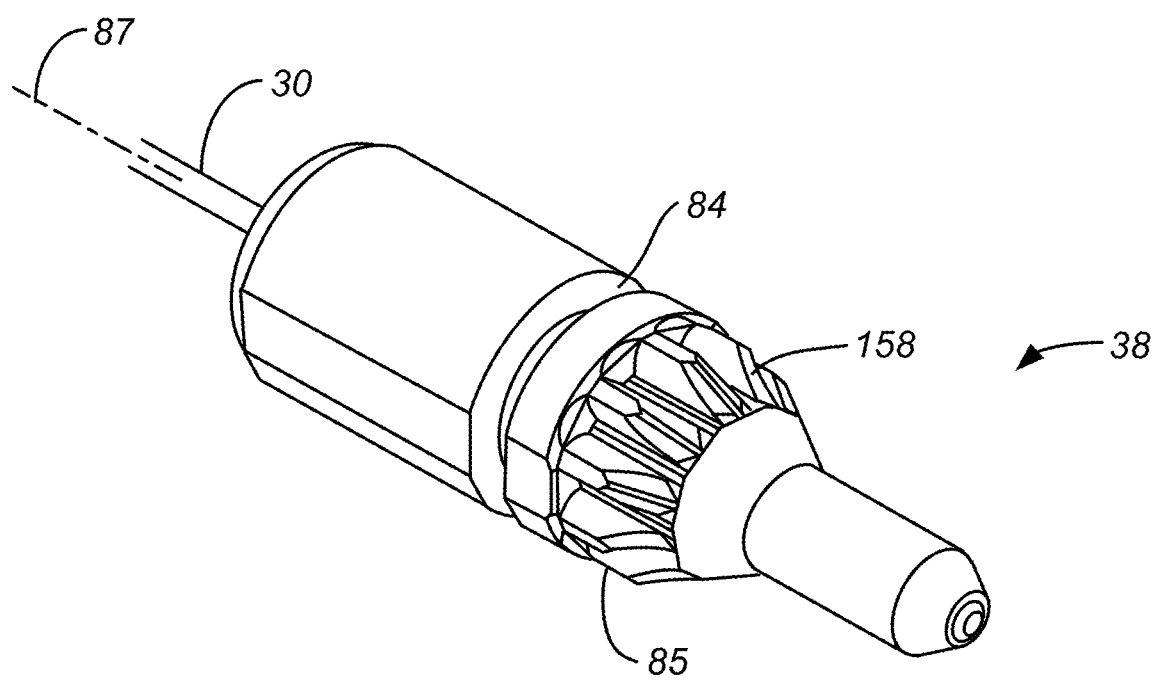
FIG. 7D is an enlarged isometric view of the plug of FIG. 7C.

FIG. 7D is an enlarged perspective view of the plug 38 with delivery tube 30 passing through the plug and extending distally therefrom. As discussed above, delivery tube 30 is affixed to plug 38, such as with an epoxy type adhesive. Plug 38 has a circumferentially extending plug locking slot 84 used to pull plug 38 proximally and push plug 38 distally along the delivery tube axis 87. This causes corresponding movement of the delivery tube 30 and diffuser 36. Plug 38 also has gear teeth 85 used to allow plug 38, and delivery tube 30 therewith, to be rotated about the delivery tube axis 87.

Figure 8:
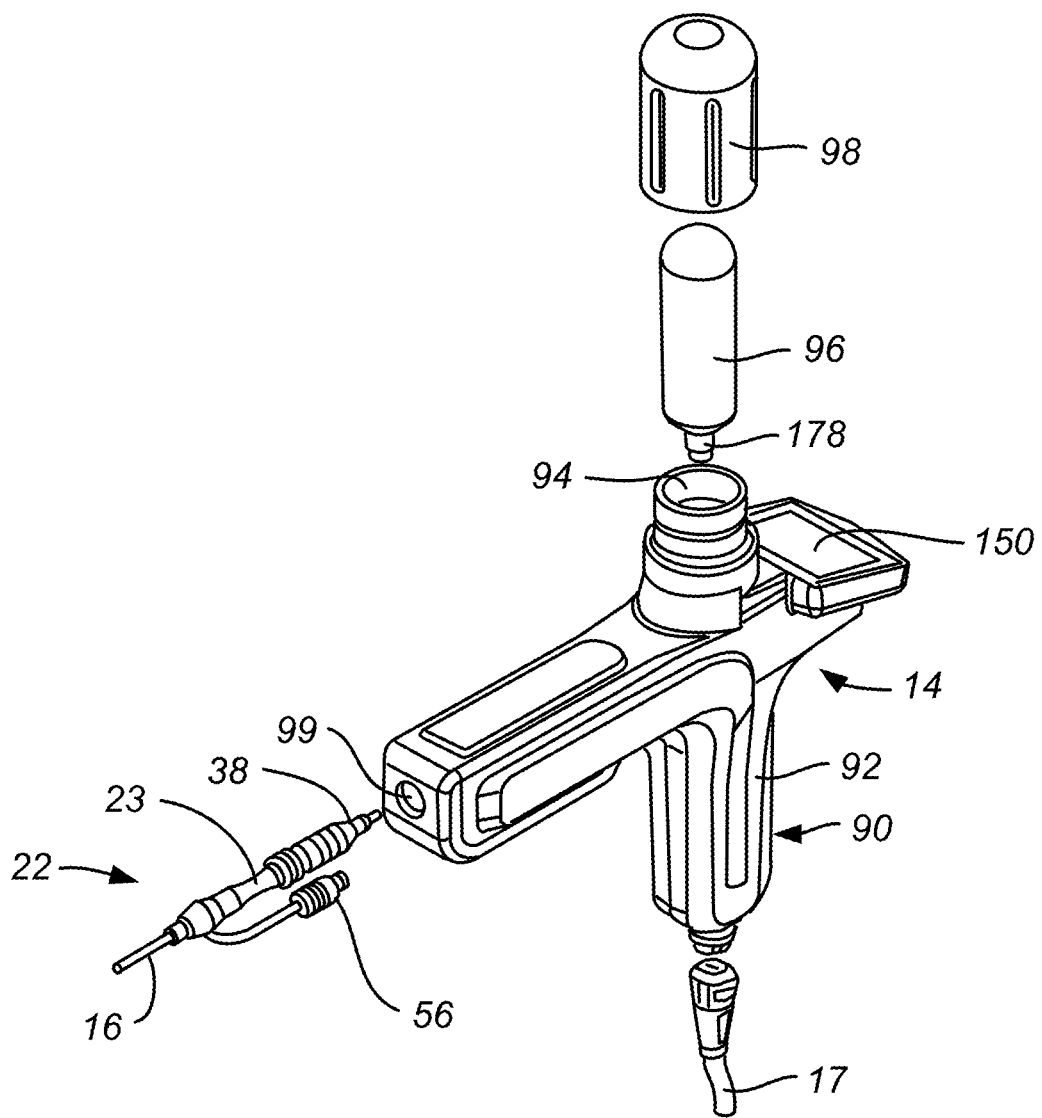
FIG. 8 is a partially exploded isometric view of portions of the ablation assembly of FIG. 1.

FIG. 8 is a partially exploded isometric view of portions of ablation assembly 10. Handle assembly 14 is shown to include a handle assembly body 90 having a handgrip portion 92 to which power and control line 17 is attached. Body 90 also includes a hollow, externally threaded tower 94 used to receive a refrigerant source 96, typically a nitrous cartridge with a preferred size of ~50 mL containing about 36 grams of nitrous oxide. A hollow, internally threaded cap 98 secures refrigerant source 96 within handle assembly body 90. Handle assembly 14 also includes a connector receptacle 99, also called first connector element 99, of controller connector 100, see FIG. 8A, for receipt of connector 22.

Figure 8A:
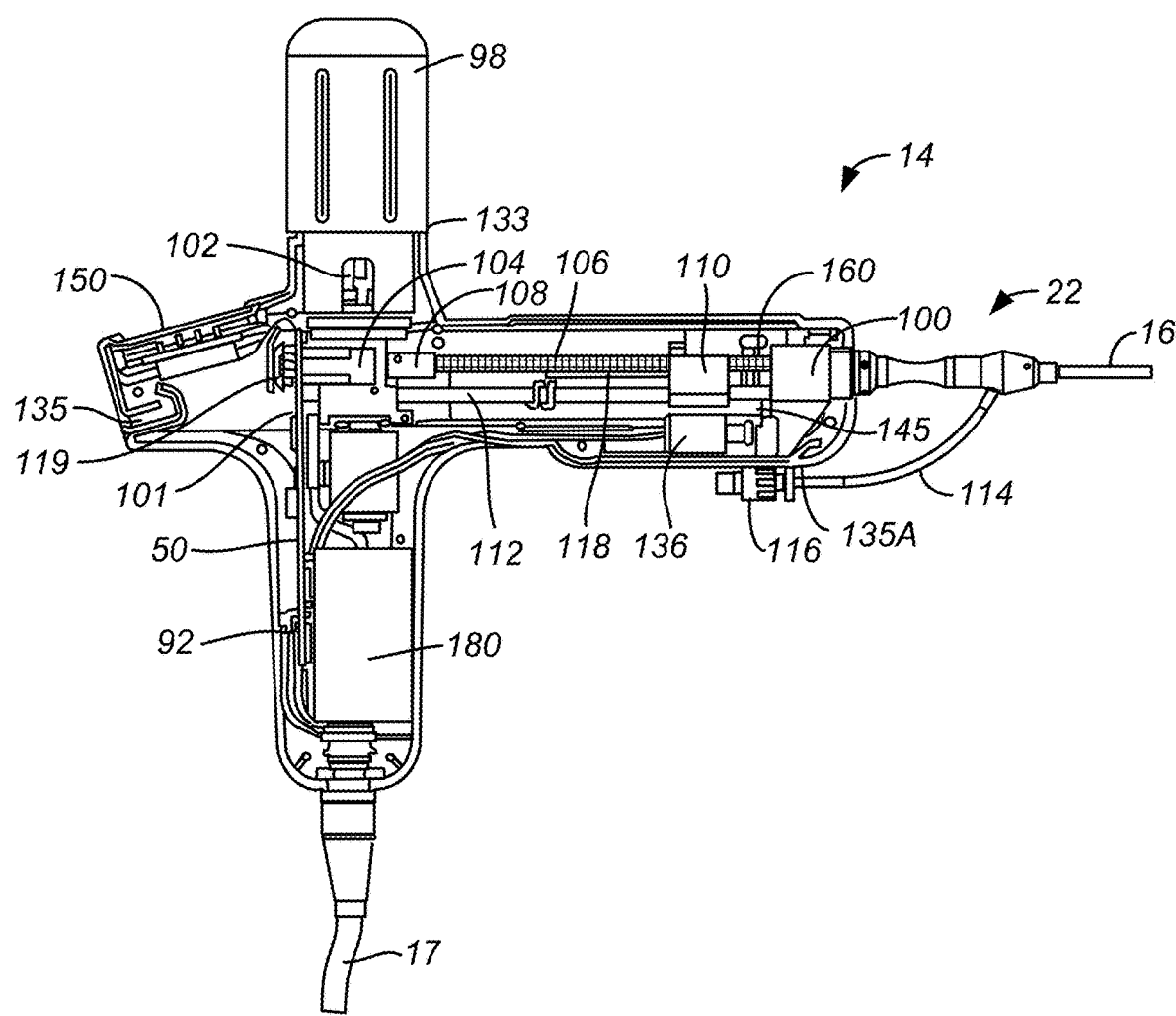
FIG. 8A is a right side cross section view of the handle assembly.
Figure 8B:
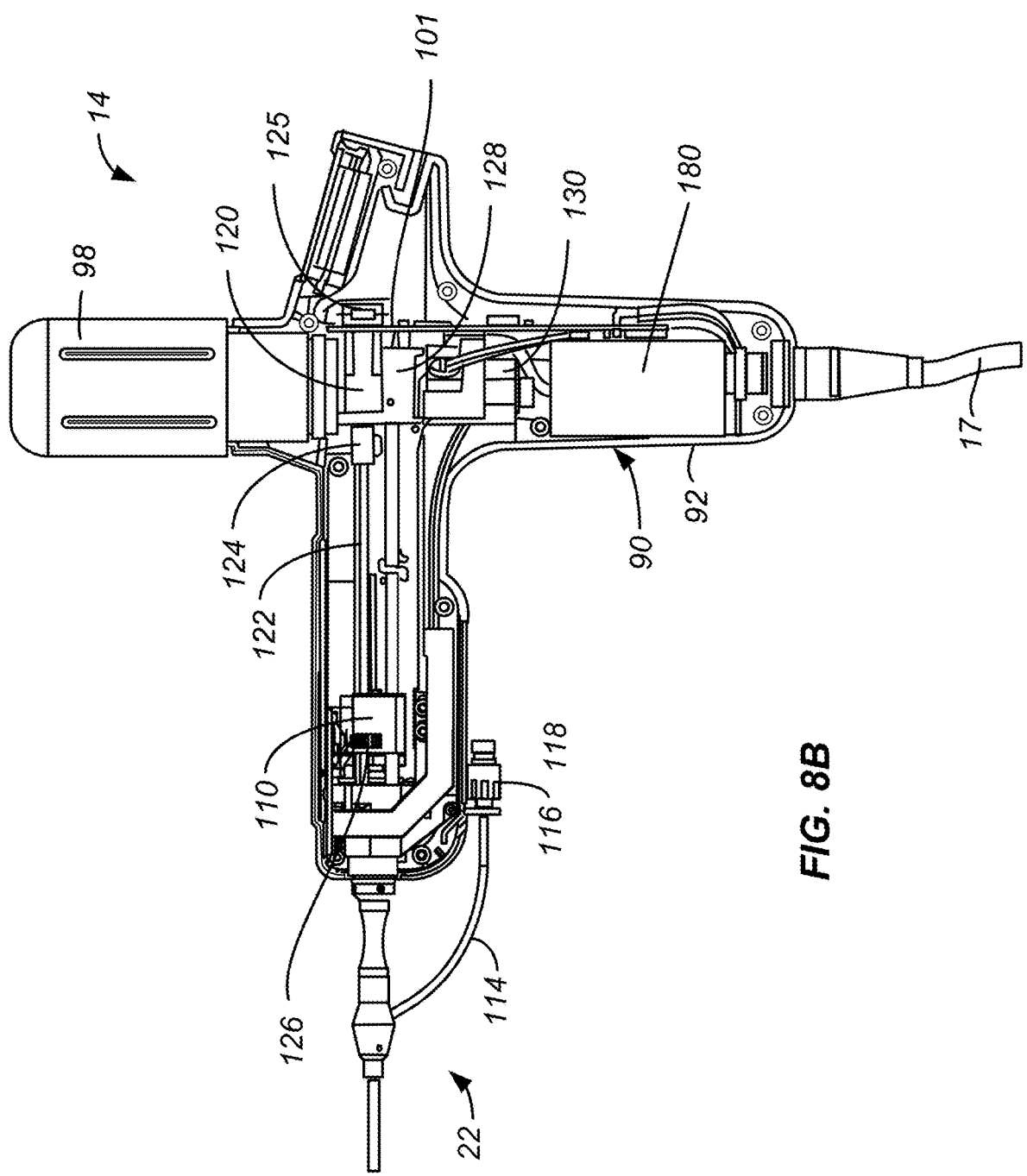
FIG. 8B is a left side cross section view of the handle assembly.

FIG. 8A is a right side view of the structure shown in FIG. 8 in a partially assembled form with the right side of the handle assembly body 90 removed to show internal components. Controller 50 shown mounted to a main printed circuit board 101. Connector 22 is shown in the process of being fully inserted into connector receptacle 99 to be placed in the load position. Assembly 14 includes a heater 102 used to heat nitrous cartridge 96 when needed. A linear drive motor 104 is connected to a rotatable, threaded shaft 106 by a threaded shaft coupler 108. Threaded shaft 106 passes through and is threadably connected to a traveler 110, also referred to as the traversing member, resulting in the linear, axial movement of the traveler. Traveler 110 is supported by and guided by a pair of bearing shafts 112, 113 along which traveler 110 slides. Bearing shaft 113 is shown in FIG. 8B. Extending from connector 22 is a balloon inflation/deflation line 114 terminating at the connector 116, typically configured to attach to a syringe. The syringe is typically used when desired to completely deflate balloon 24. Refrigerant from cartridge 96 passes through a delivery line 118 terminating at traveler 110. Delivery line 118 is a flexible delivery line and can be looped around bearing shafts 112, 113 without kinking to accommodate the linear, axial movement of traveler 110. The rotation of linear drive motor 104 is monitored by controller 50 through the use of a counter wheel 119, having light and dark segments, and an appropriately located light sensor to monitor the rotation of counter wheel 119.

FIG. 8B corresponds to FIG. 8A but illustrates the left side of the structure. Handle assembly 14 includes a rotation motor 120 connected to a rotation shaft 122 by a rotation coupler 124. Rotation of rotation motor 120 is monitored by controller 50 through the use of a counter wheel 125 and an appropriately located light sensor in a manner similar to that used with linear drive motor 104. Rotation shaft 122 has, in this example, a square cross-sectional shape; other rotationally driving shapes can also be used. Rotation shaft 122 passes through traveler 110 a manner which allows shaft 122 to freely rotate within traveler 110 and allows traveler 110 to move freely in a linear, axial manner. A drive gear 126 is bracketed by traveler 110 to move with the traveler. Drive gear 126 is rotationally coupled to rotation shaft 122 so that rotation of shaft 122 causes drive gear 126 to rotate. Drive gear 126 is slideably mounted to rotation shaft 122 so that the drive gear slides along rotation shaft 122 as traveler 110 moves in its linear, axial manner. As will be explained below, when connector 22 is mounted to handle assembly 14, rotation of shaft 122 causes the plug 38 and delivery tube 30 therewith to rotate.

Figure 9B:
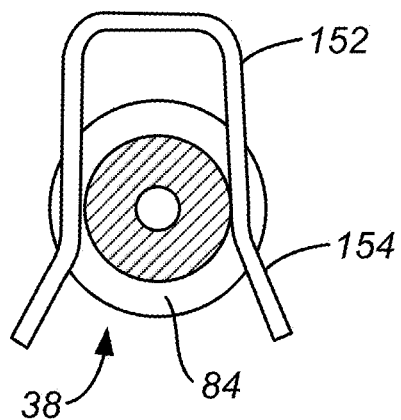
FIGS. 9B and 9C show the catheter plug locking wire engaging the plug locking slot.
Figure 9D:
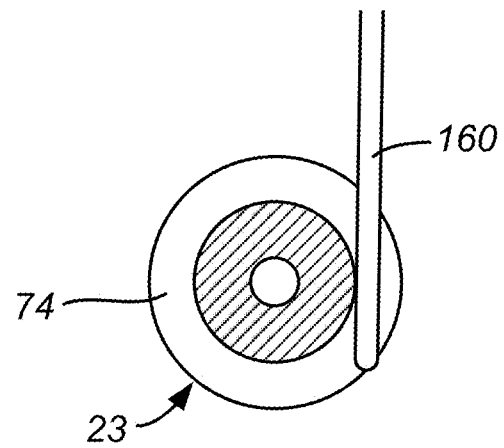
FIG. 9D shows the structure of FIG. 8E but with the connector body locking wire engaging the body locking slot of the catheter body.
Figure 9:
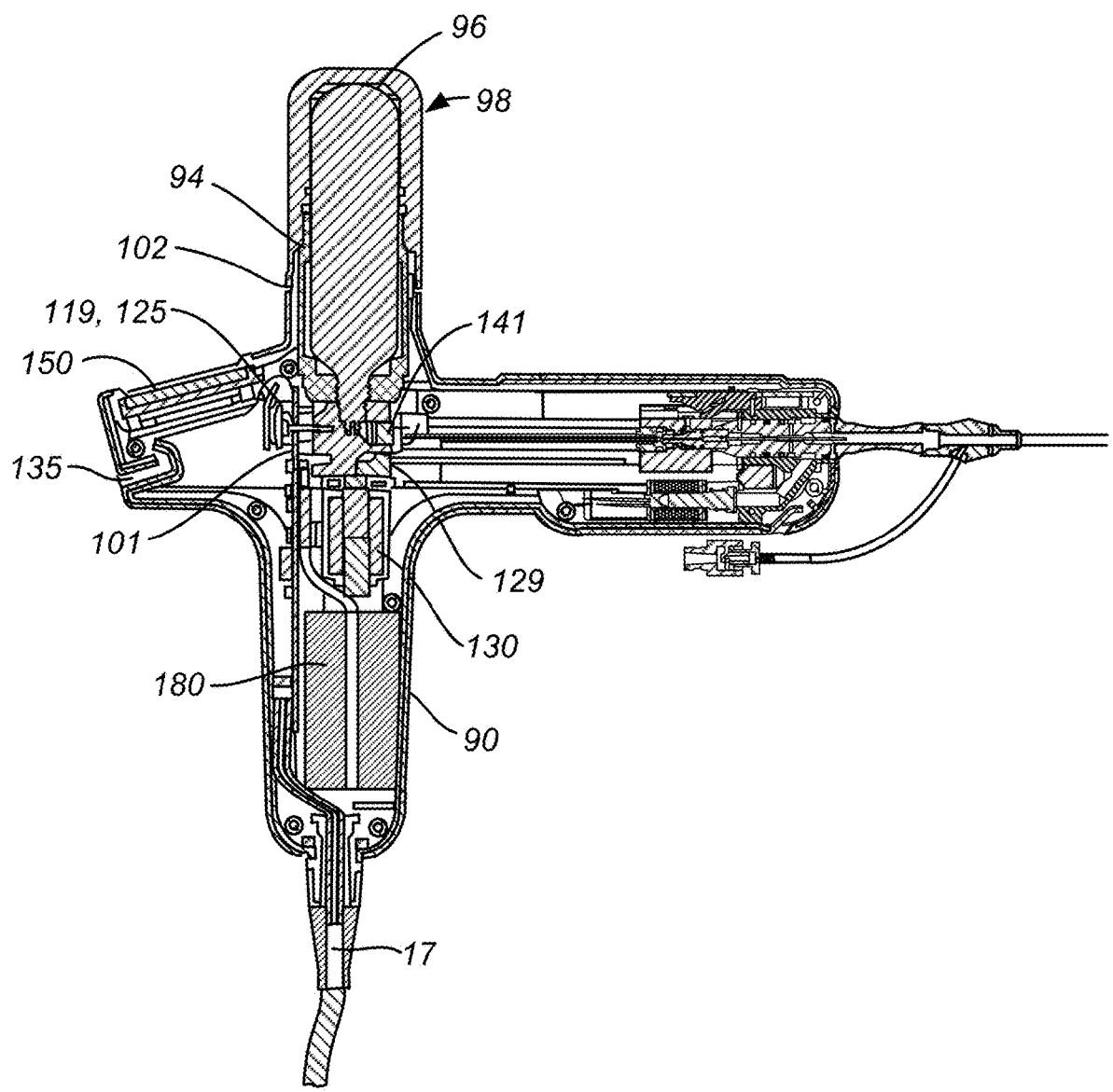
FIG. 9 is a cross-sectional view of the handle assembly in the controller load position

Refrigerant from refrigerant source 96 passes through a manifold 128 (FIG. 8B) under the control of the refrigerant controlling delivery solenoid 130, through a delivery line coupler 129, see FIG. 9, and into delivery line 118. The pressure within refrigerant source 96 is monitored by controller 50 through a pressure transducer 141. The operation of delivery solenoid 130 can be controlled by the operator using foot pedal assembly 15. As will be discussed in more detail below, tapping refrigerant delivery foot pedal 132 typically provides enough refrigerant to expand balloon 24 and provide visualization of the location of the refrigerant port. Application of refrigerant to the inner surface of balloon 24 to ablate tissue can be controlled manually by the user pressing on foot pedal 132. The system can be programmed to provide a set period of refrigerant delivery depending on the particular therapy, through either a regulated time such as 2 to 20 seconds or regulated translation speed such as 0.5 to 1.5 mm/sec, and is preferably programmed to limit the maximum length of time for refrigerant delivery to a target treatment site to, for example, 10 seconds. Foot pedal assembly 15 also includes a foot-actuated deflation button 134 which allows the operator to deflate the balloon, typically placing the balloon interior of the balloon at atmospheric pressure. Pressing deflation button 134 actuates an exhaust solenoid valve 136, see FIG. 9A, which is connected to exhaust passage 62 (FIG. 7B) of connector body 23 by a passageway 138. The exhaust from the balloon 24 through the actuation of exhaust solenoid valve 136 enters the interior of handle assembly body 90. Body 90 has two, redundant ports 133, 135 to help ensure that gases vented into the interior of handle assembly body 90 can escape to the ambient environment regardless of how handle assembly body 90 is being held. Furthermore, if the exhaust valve 136 fails to open or is otherwise occluded, pressure relief valve 145 will actuate, mitigating the risk of balloon over pressurization. See FIGS. 9E and 9F. Pressure relief valve 145 also enables the balloon to remain statically inflated at a regulated pressure of, for example, 2.9 psig.

Figure 14:
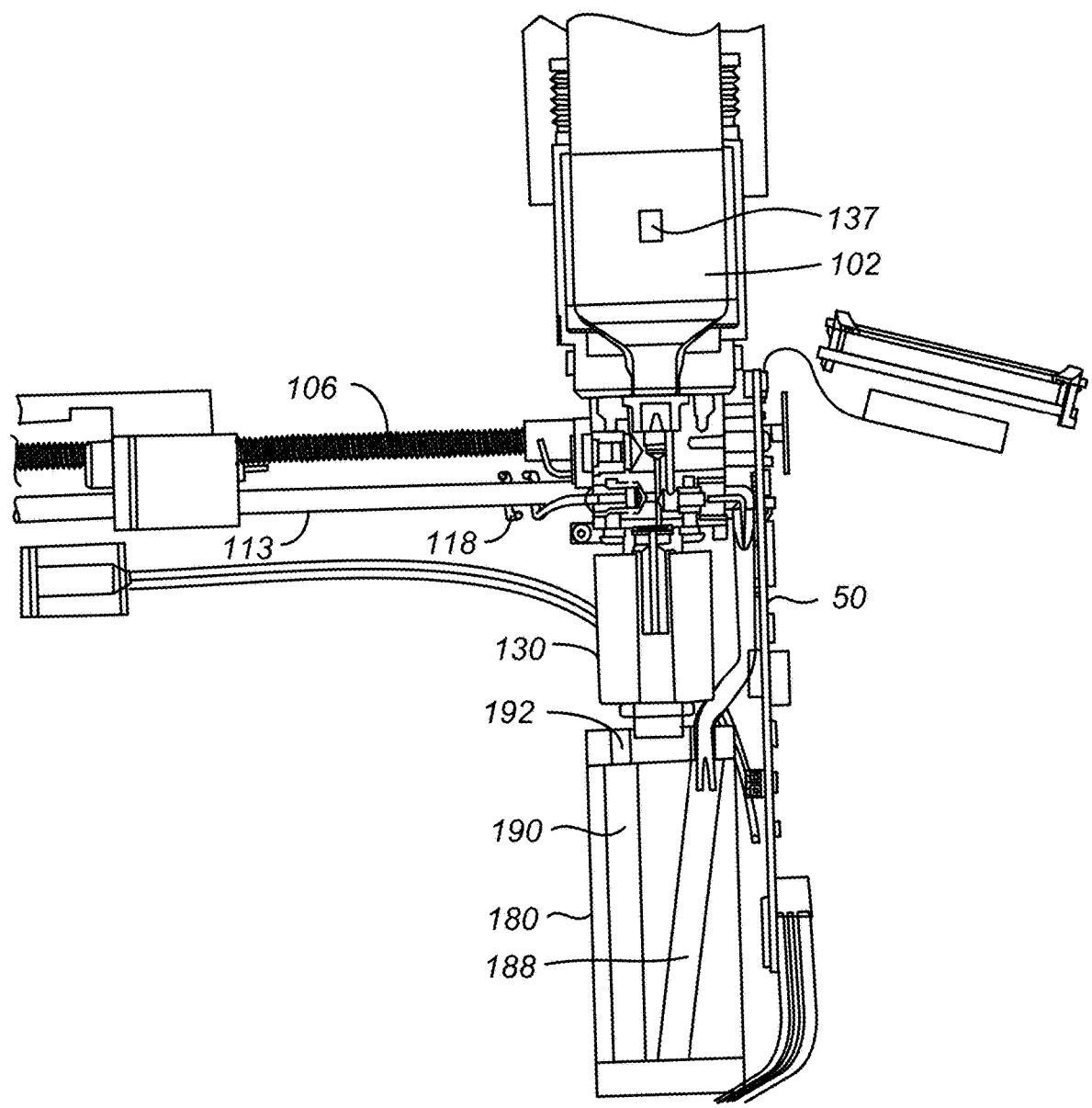
FIGS. 14, 14A, 14B and 14C illustrates how excess liquid refrigerant is directed into a refrigerant venting chamber: removal of the refrigerant canister from the handle assembly.
Figure 14A:
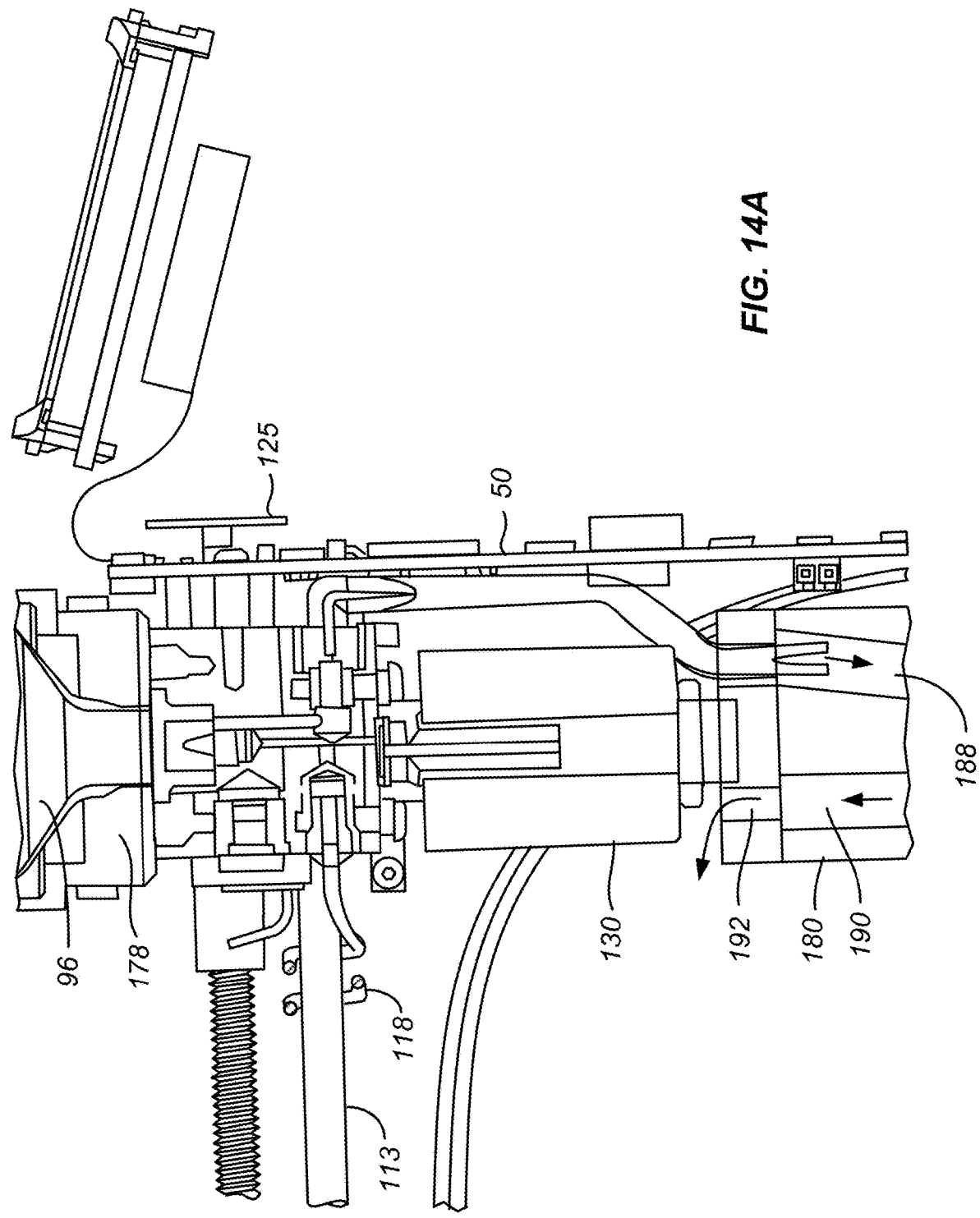
Figure 14B:
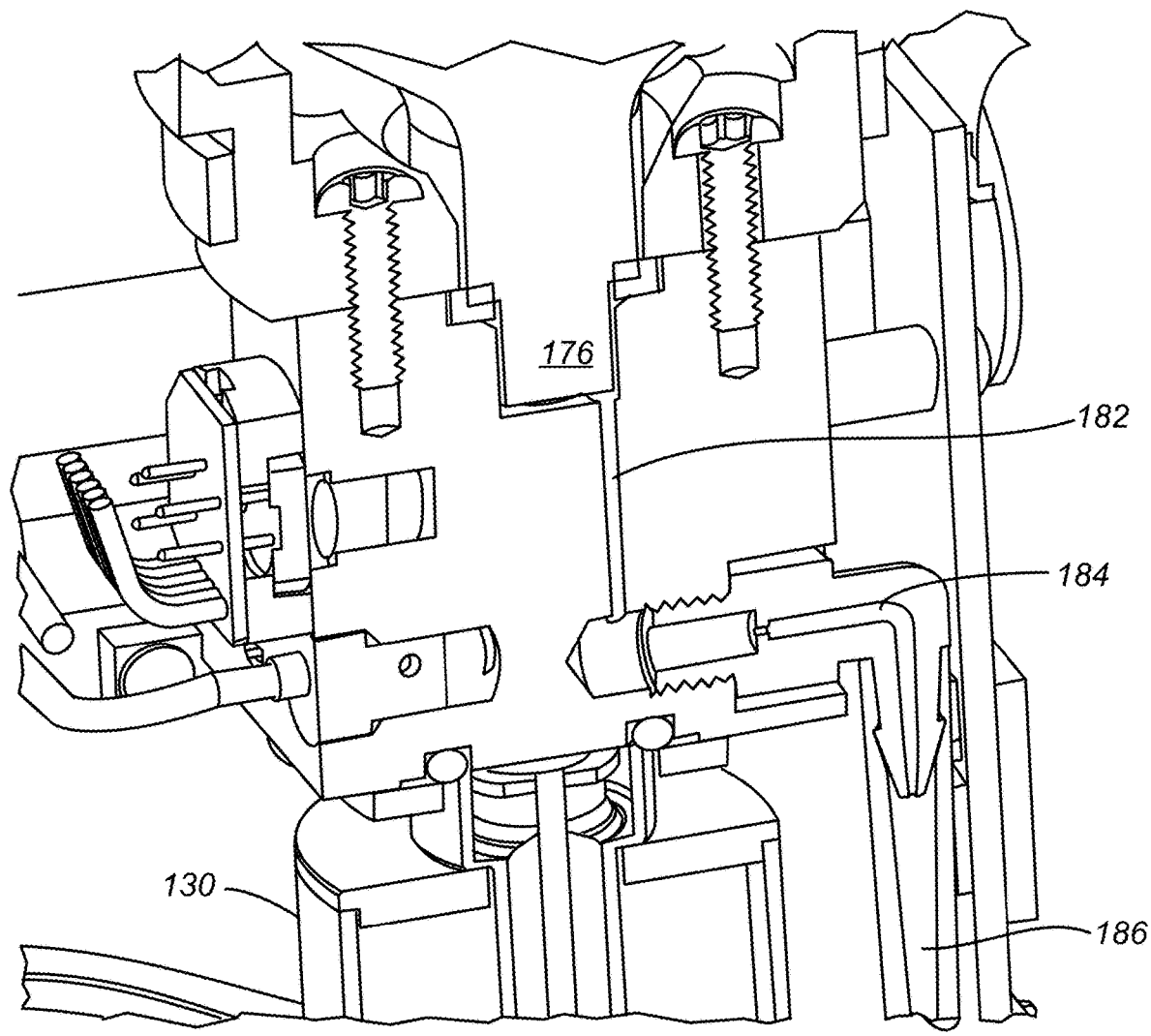
Figure 14C:
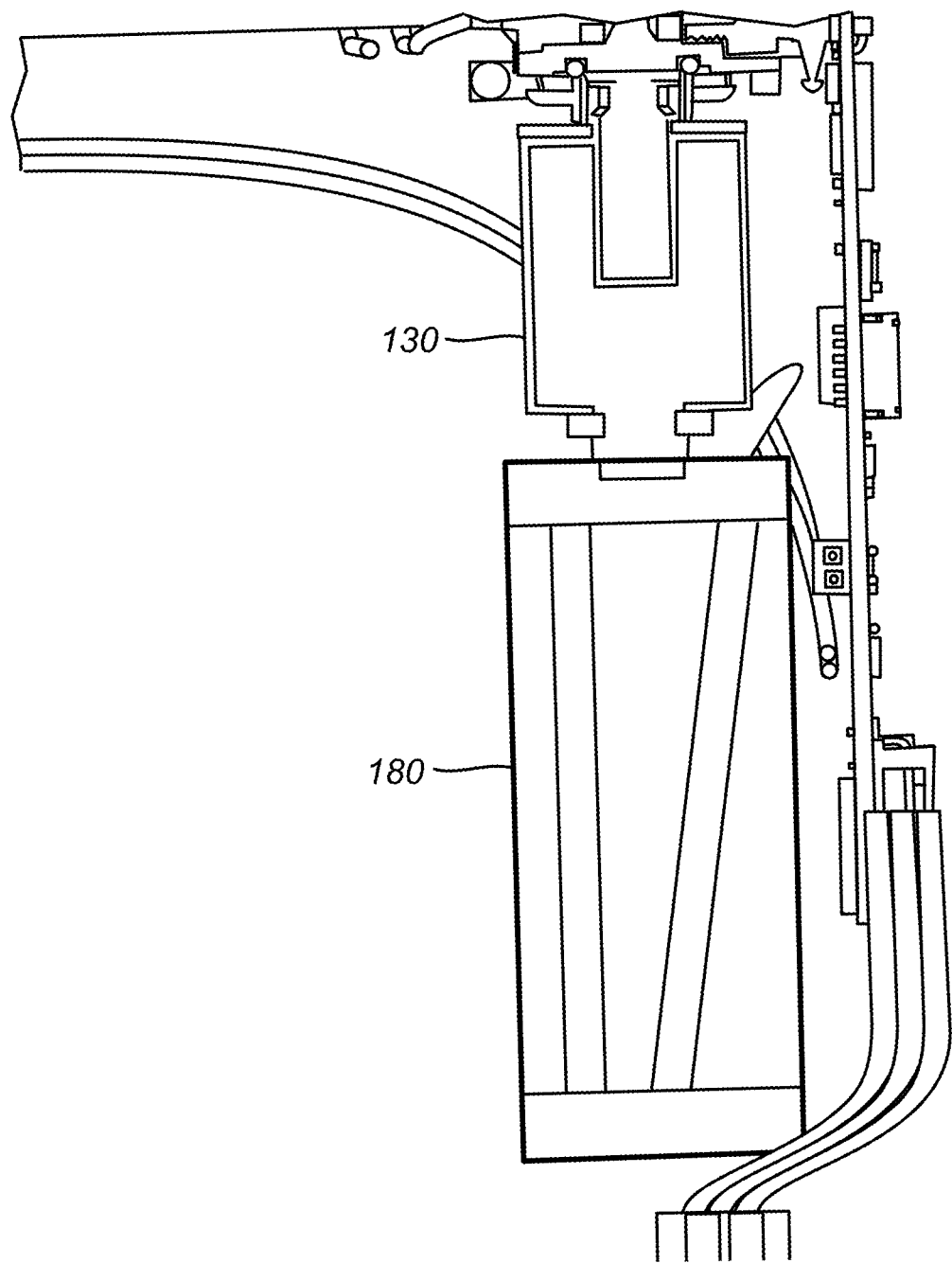

Controller 50 controls and monitors the pressure of the refrigerant within refrigerant source 96 using a temperature sensor such as a thermistor 137, see FIG. 14, and pressure transducer 141, see FIG. 9. Having accurate pressure and temperature information for the refrigerant within refrigerant source 96 allows the system to determine if the nitrous oxide cylinder contains liquid based on the saturated liquid/gas properties of the refrigerant. Additionally, the temperature sensor can be used to detect a malfunction in the heater circuit that may result in overheating and hence over pressurization of the refrigerant cartridge. If overheating is detected, the controller will turn of the heater and/or completely disconnect itself from power.

Foot pedal assembly 15 also includes the left and right movement foot pedals 140, 142. Left and right foot pedals 140, 142 are used to control linear drive motor 104 and rotation motor 120. The user selects which function left and right foot pedals 140, 142 will be used for, that is linear movement or rotational movement. Upon the use of movement mode button 144, foot pedal assembly 15 provides the operator with an indication of which mode has been selected by the illumination of either straight arrows 146, 147, or curved arrows 148, 149. Assuming movement mode button 144 is pressed and straight arrows 146, 147 are illuminated, actuation of left or right foot pedals 140, 142 will cause linear drive motor 104 to operate thus rotating threaded shaft 106 and causing traveler 110 to translate a linear manner. As indicated by the orientation of arrow 146, in this example pressing on left foot pedal 140 causes traveler 110 to move to the left in FIG. 8A thus causing diffuser 36 to move in a proximal direction. Similarly, pressing on right foot pedal 142 causes traveler 110 to move to the right in FIG. 8A causing diffuser 36 to move in a distal direction. This movement can also be preprogrammed and/or limited in the length of travel permitted.

Depressing movement mode button 144 again changes the mode from linear motion to rotational motion. When the system is in the rotational motion mode, counterclockwise curved arrow 148 and clockwise curved arrow 149 are illuminated indicating the direction of rotation of delivery tube 30 and diffuser 36 associate with pressing left and right foot pedals 140, 142. Depressing the left foot pedal 140 provides a signal to rotation motor 120 to rotate rotation shaft 122 in a counterclockwise direction thus causing delivery tube 30 and diffuser 36 therewith to rotate in a counterclockwise direction. Depressing right foot pedal 142 provides a signal to rotation motor 120 to rotate rotation shaft 122 in a clockwise direction thus causing delivery tube 30 and diffuser 36 to rotate in a clockwise direction.

Typical operational parameters for ablation assembly 10 include the following. Translation at a rate between 0.25 mm/sec to 2.5 mm/sec, wherein the rate of translation for therapeutic use is between 0.5 mm/sec and 1.5 mm/sec. Rotation can be at a rate between 1 and 10 RPM.

In addition to having arrows 146-149 illuminate, controller 50 could create a visual indication of the selection on an LCD display 150 on handle assembly 14. In addition, an audible indication of the selection can be provided by broadcasting a verbal alert, such as linear movement selected, or by a nonverbal alert, for example a single beep for counterclockwise rotation, and a double beep for clockwise rotation, a long tone for proximal linear movement, and a double long tone for distal linear movement.

Figure 9A:
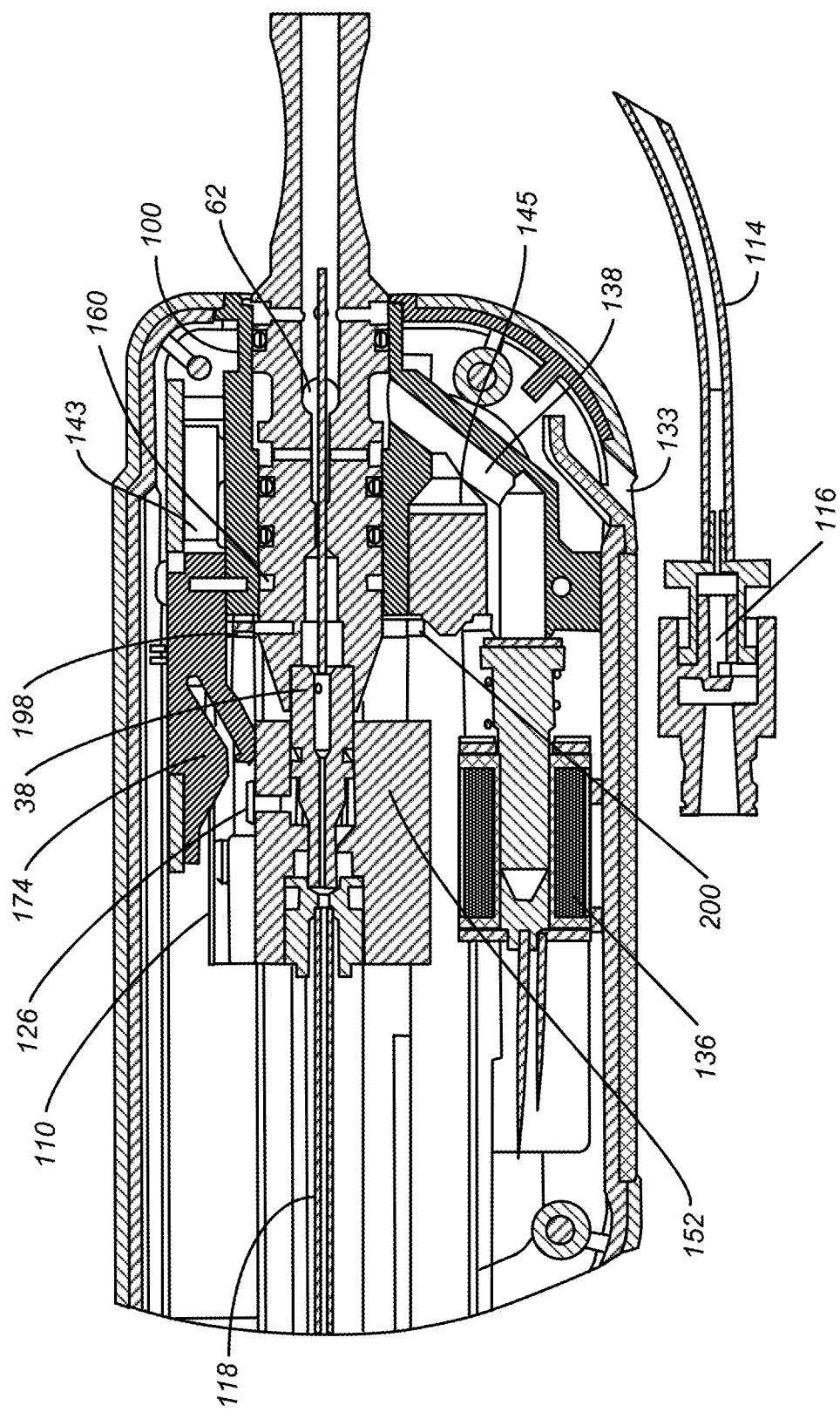
FIG. 9A is an enlarged view of a portion of the structure of FIG. 9.
Figure 9C:
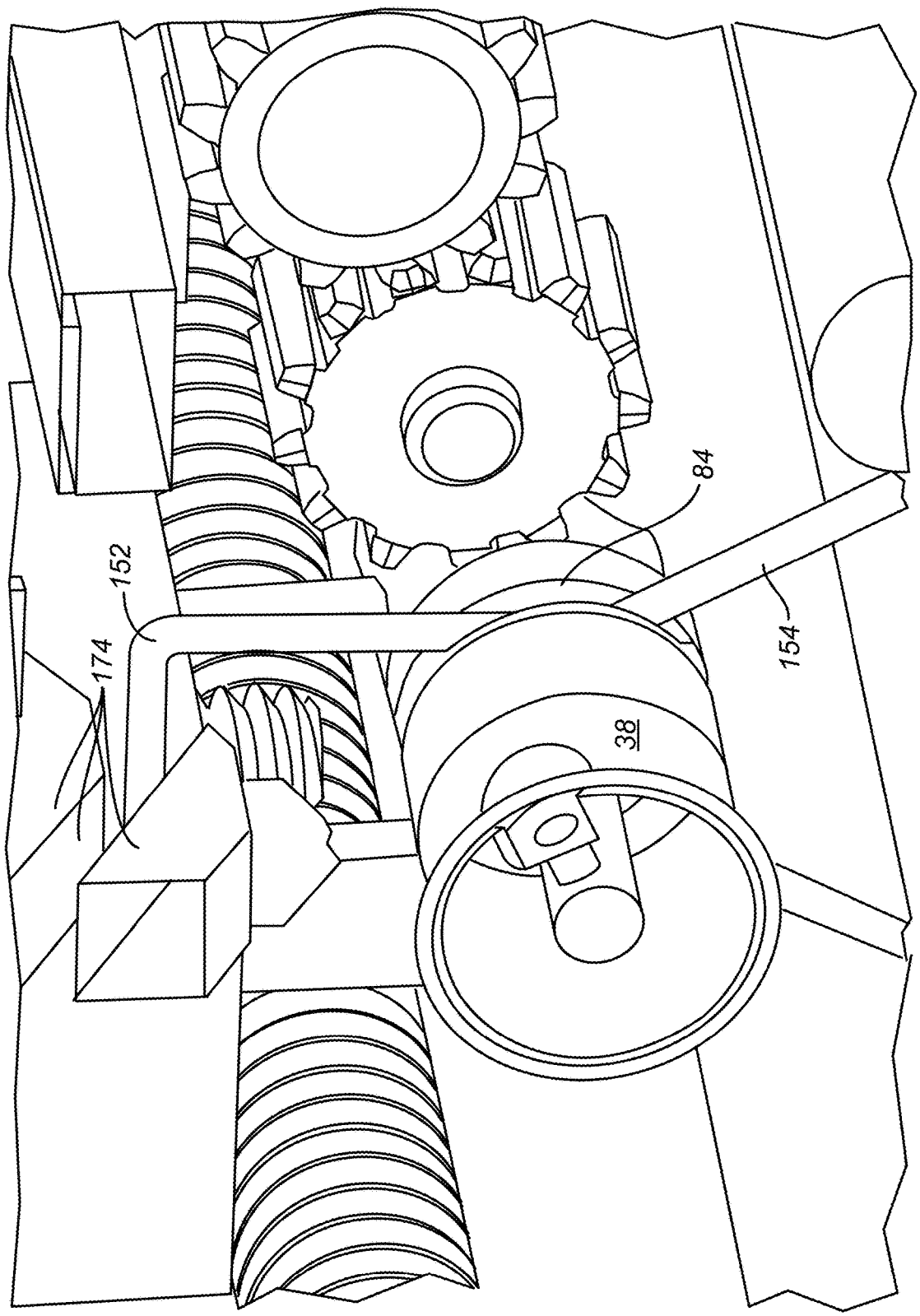
Figure 9E:
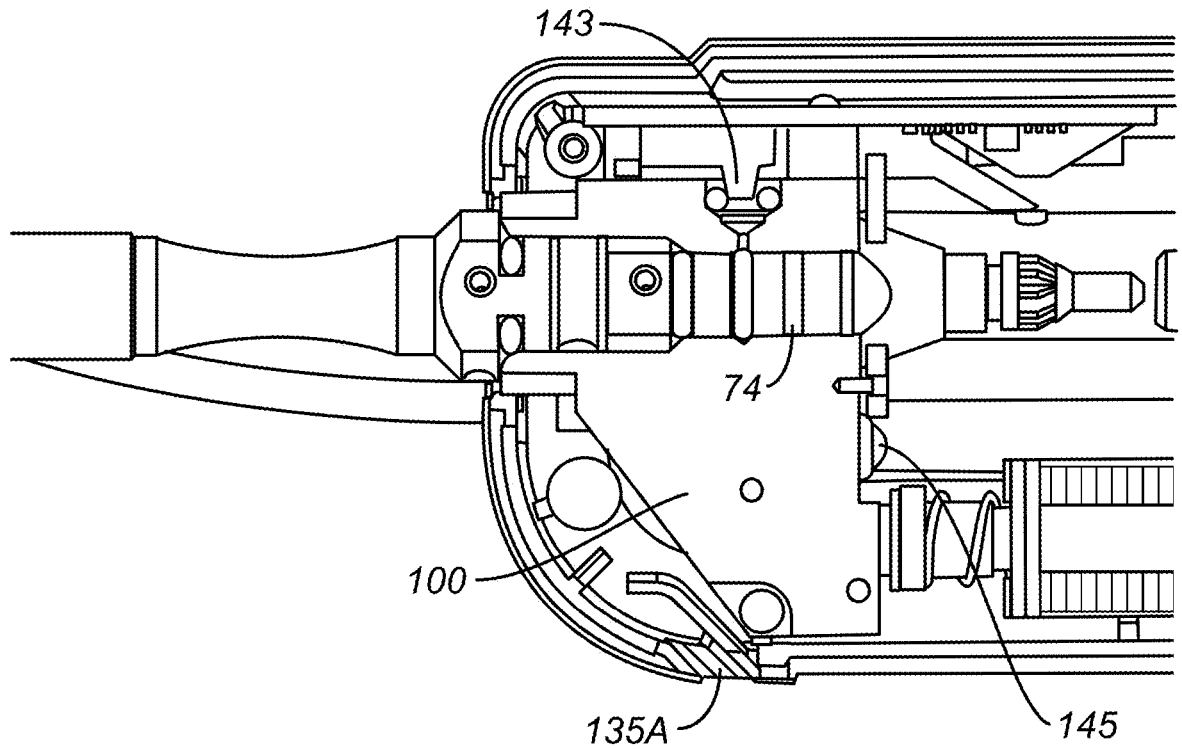
FIGS. 9E and 9F illustrate how the pressure within the balloon is communicated to a pressure transducer in the controller connector.
Figure 9F:
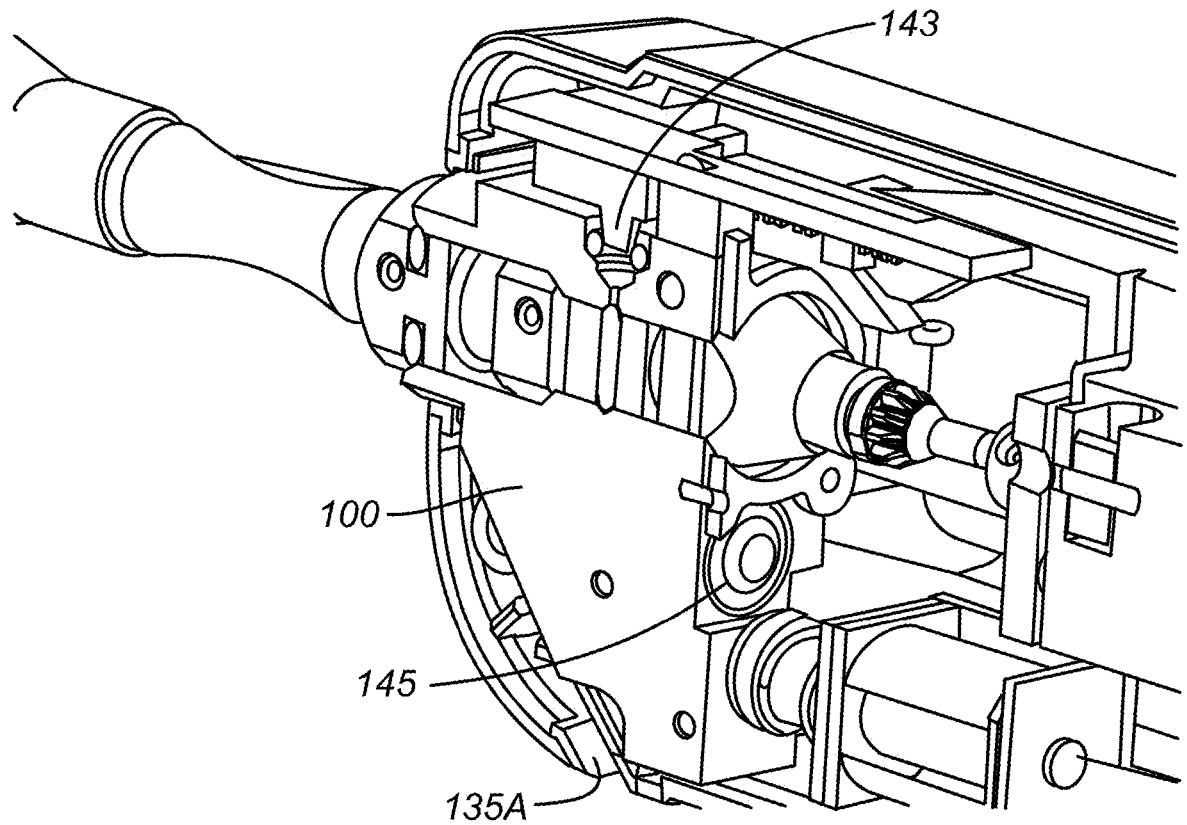

FIG. 9B is a simplified illustration showing the relationship of catheter plug locking wire 152 relative to plug locking slot 84 of plug 38 when assembly 10 is in the connector-attachment state of FIGS. 9 and 9A. This state is also shown in FIG. 9C. As plug 38 is inserted through first connector element 99 and into handle assembly body 90, the legs 154 are expanded outward while riding along tapered surface 156 of plug 38, see FIG. 7D, and the tapered leading edges 158 of gear teeth 85. When connector 22 is fully inserted into handle assembly body 90, the legs 154 of catheter plug locking wire 152 will snap into plug locking slot 84 as shown in FIGS. 9B and 9C.

FIG. 9D is a simplified illustration showing the relationship of connector body locking wire 160 relative to body locking slot 74 of connector body 23 when ablation assembly 10 is in the connector attachment state of FIGS. 9 and 9A. As connector body 23 is inserted through connector receptacle 99 and into handle assembly body 90, connector body locking wire 160 is deflected away, FIG. 8E, as it rides along tapered surface 162 of connector body 23, see FIG. 7A. When connector 22 is fully inserted into handle assembly body 90, connector body locking wire 160 will snap into body locking slot 74 as shown in FIG. 9D. Accordingly, examples of ablation assembly 10 provide for the automatic attachment of connector 22 to handle assembly 14.

Figure 10:
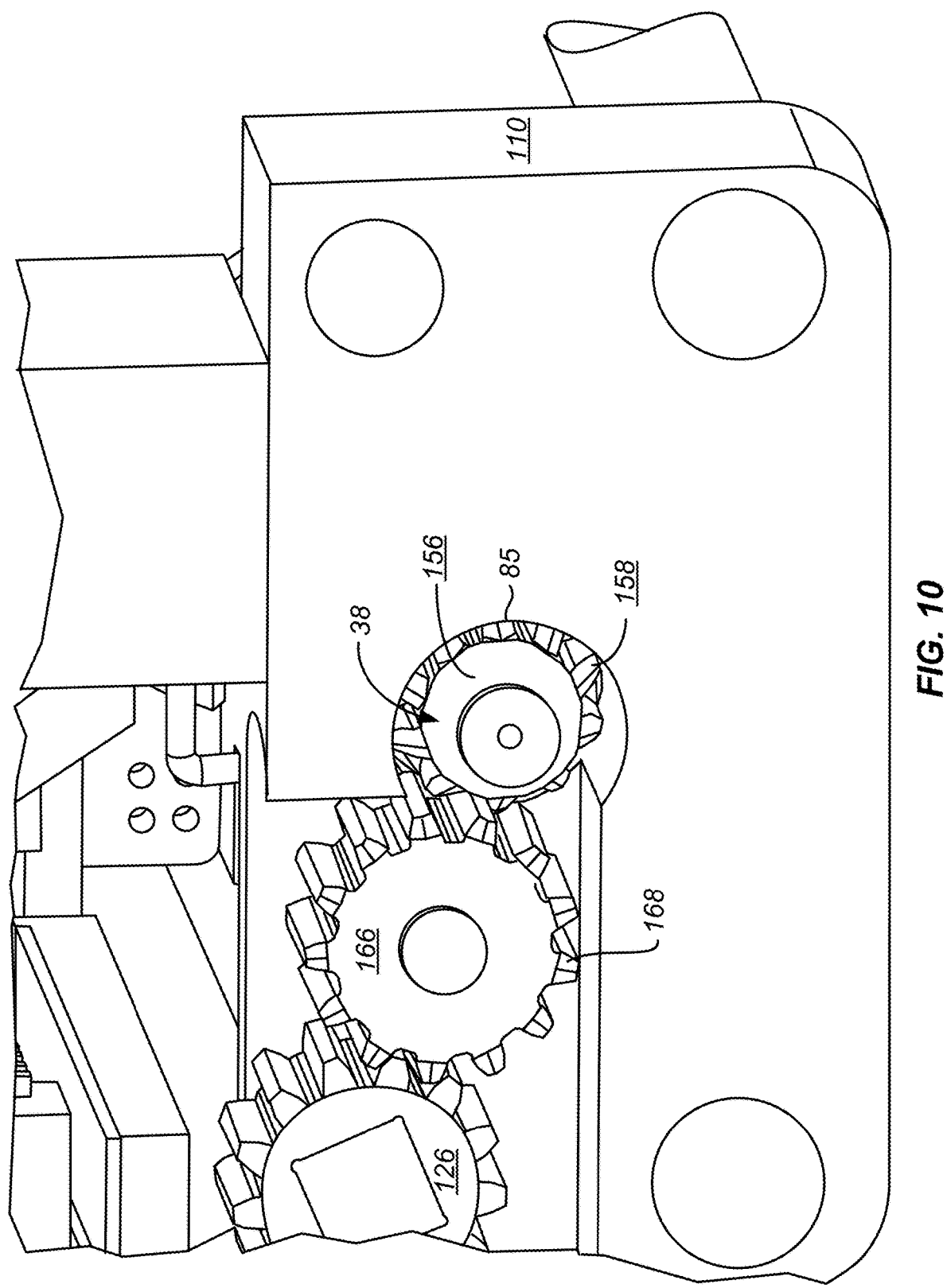
FIG. 10 is a partial cross-sectional view of the traveler of FIG. 8A showing the idler gear connecting the drive gear and the purity of the plug.

FIG. 10 illustrates the relationship among drive gear 126, driven by rotation shaft 122, gear teeth 85 of plug 38, and an idler gear 166 coupling the two. Drive gear 126 and idler gear 166 are both mounted to traveler 110 at fixed locations relative to traveler 110, but are free to rotate, and remain engaged as traveler 110 is moved in a linear manner by the rotation of threaded shaft 106. The ends 168 of the gear teeth of idler gear 166 have a V-shaped taper to promote the proper engagement with gear teeth 85 as plug 38 is inserted through first connector element 99 when ablation assembly 10 is in the connector attachment state of FIG. 9.

Figure 11:
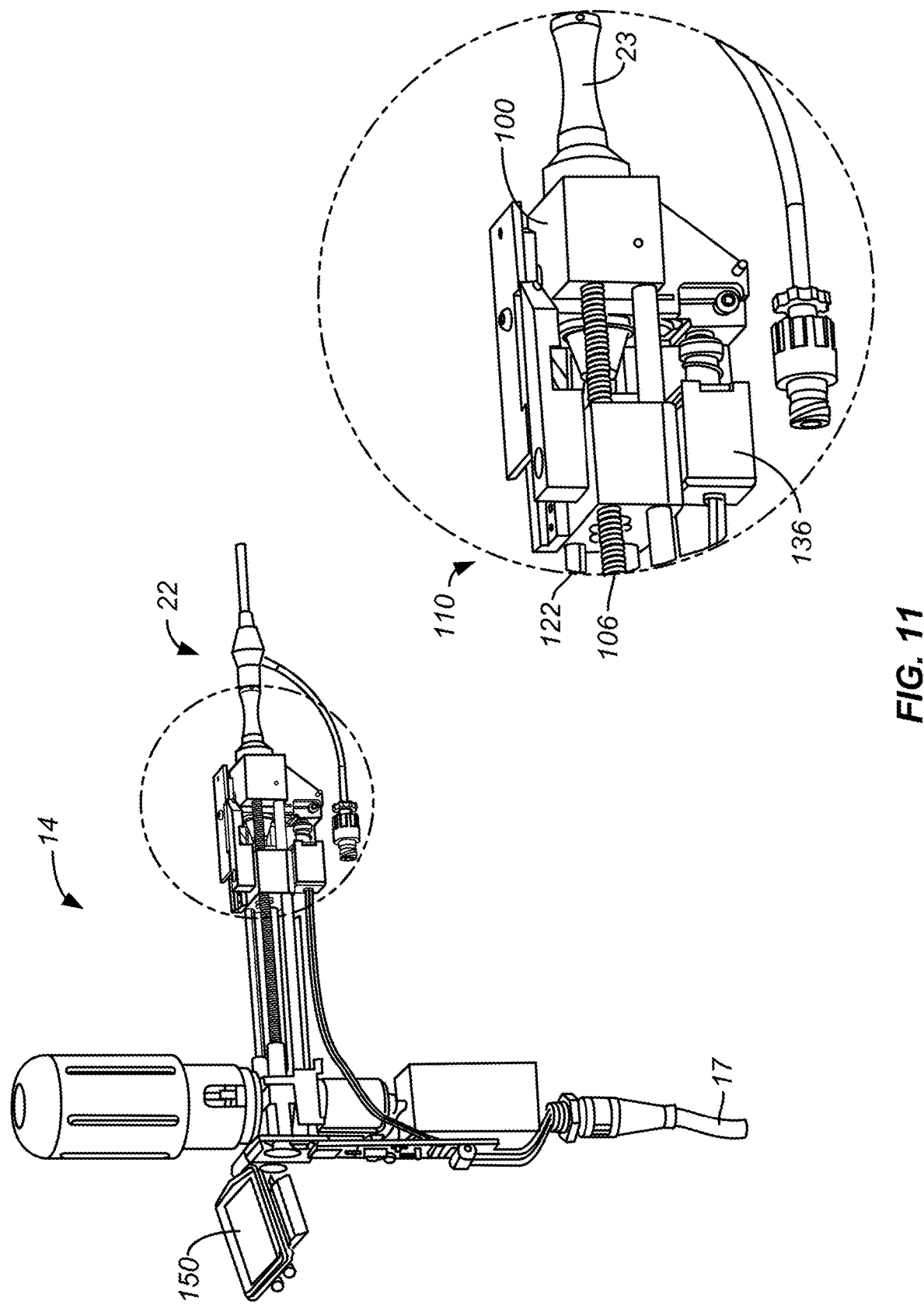
FIG. 11 shows isometric views of portions of the handle assembly at the start of treatment.
Figure 12:
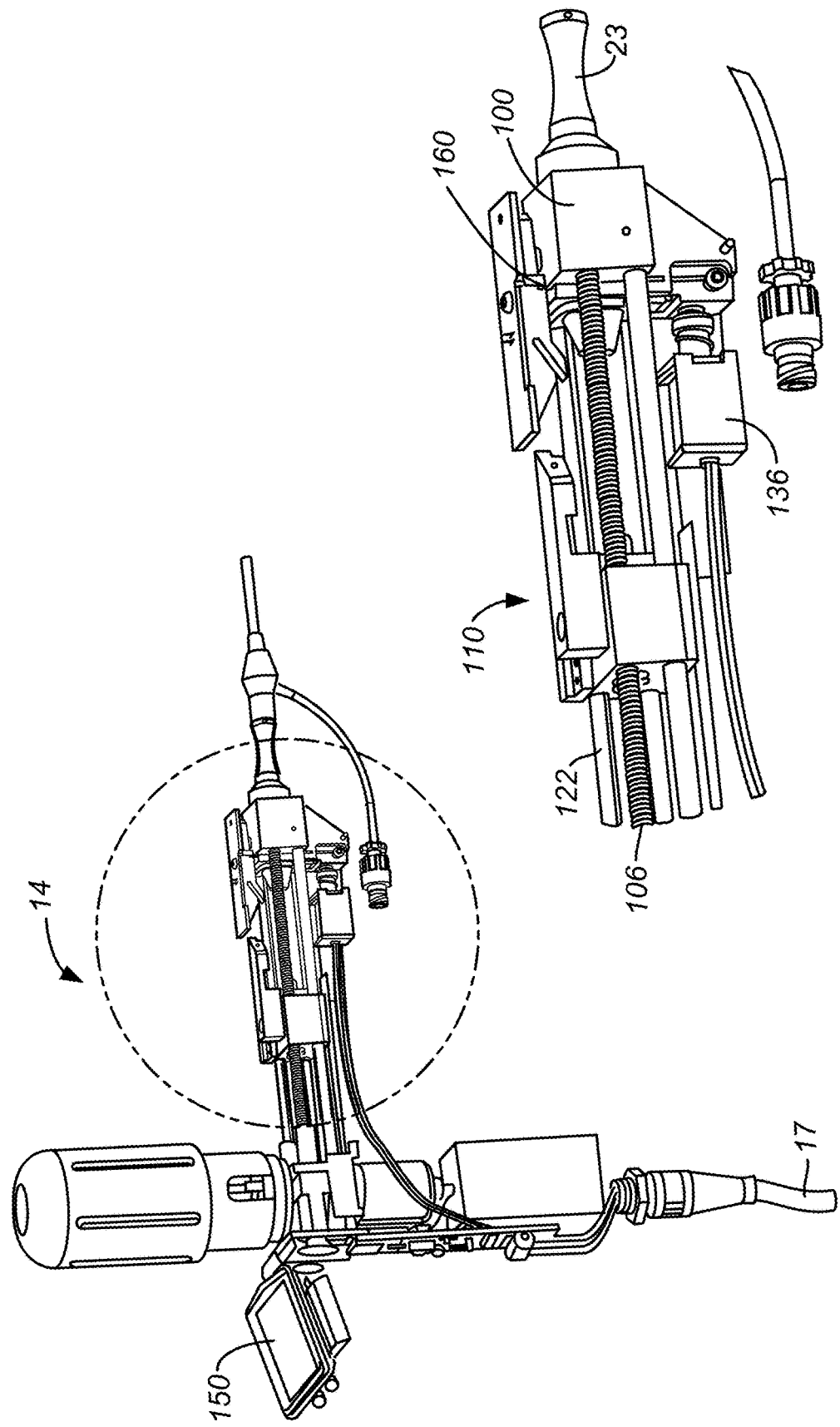
FIG. 12 shows the structure of FIG. 11 at the end of treatment.

FIG. 11 illustrates a portion of the structure of FIG. 9 after movement of traveler 110 a short distance proximally, to the left in FIG. 11, placing assembly 10 in a distal, typically starting, treatment position corresponding to FIG. 2B. FIG. 12 shows the structure of FIG. 11 after further movement of traveler 110 in a proximal direction, that is to the left in FIG. 12, placing assembly 10 in a proximal, typically ending, treatment position corresponding FIG. 2C. Because refrigerant is sprayed into the interior of the balloon 24 during treatment, the exhaust valve 136 can remain open during the treatment.

Figure 8C:
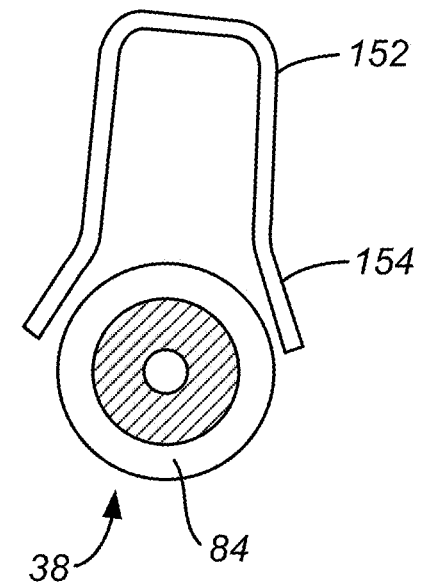
FIGS. 8C and 8D show the relationship of the catheter plug locking wire relative to the plug locking slot of the plug when the ablation assembly is in the catheter connector disconnect state of FIGS. 13 and 13A.
Figure 8E:
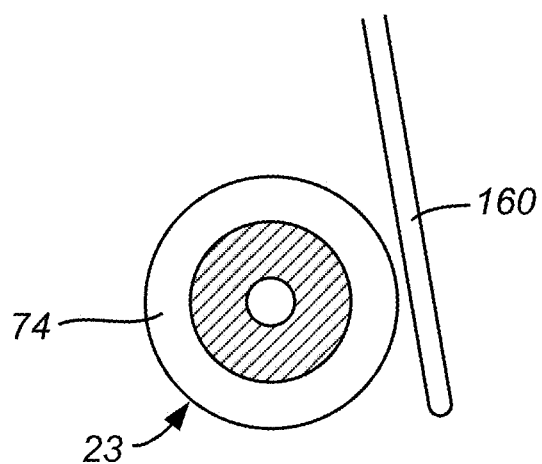
FIG. 8E is a simplified schematic cross section the connector body locking wire biased away from the body locking slot of the connector body.
Figure 8D:
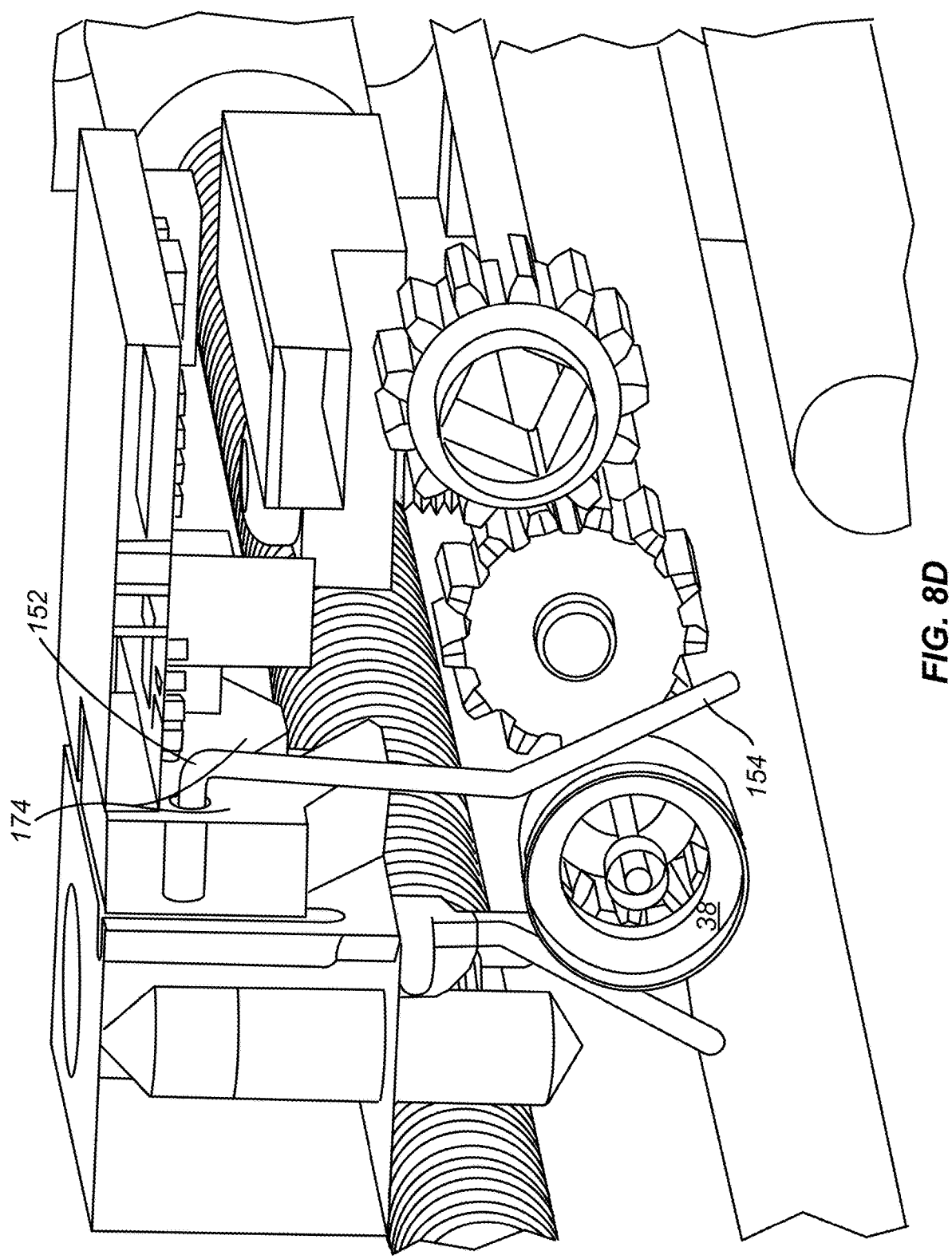
Figure 13:
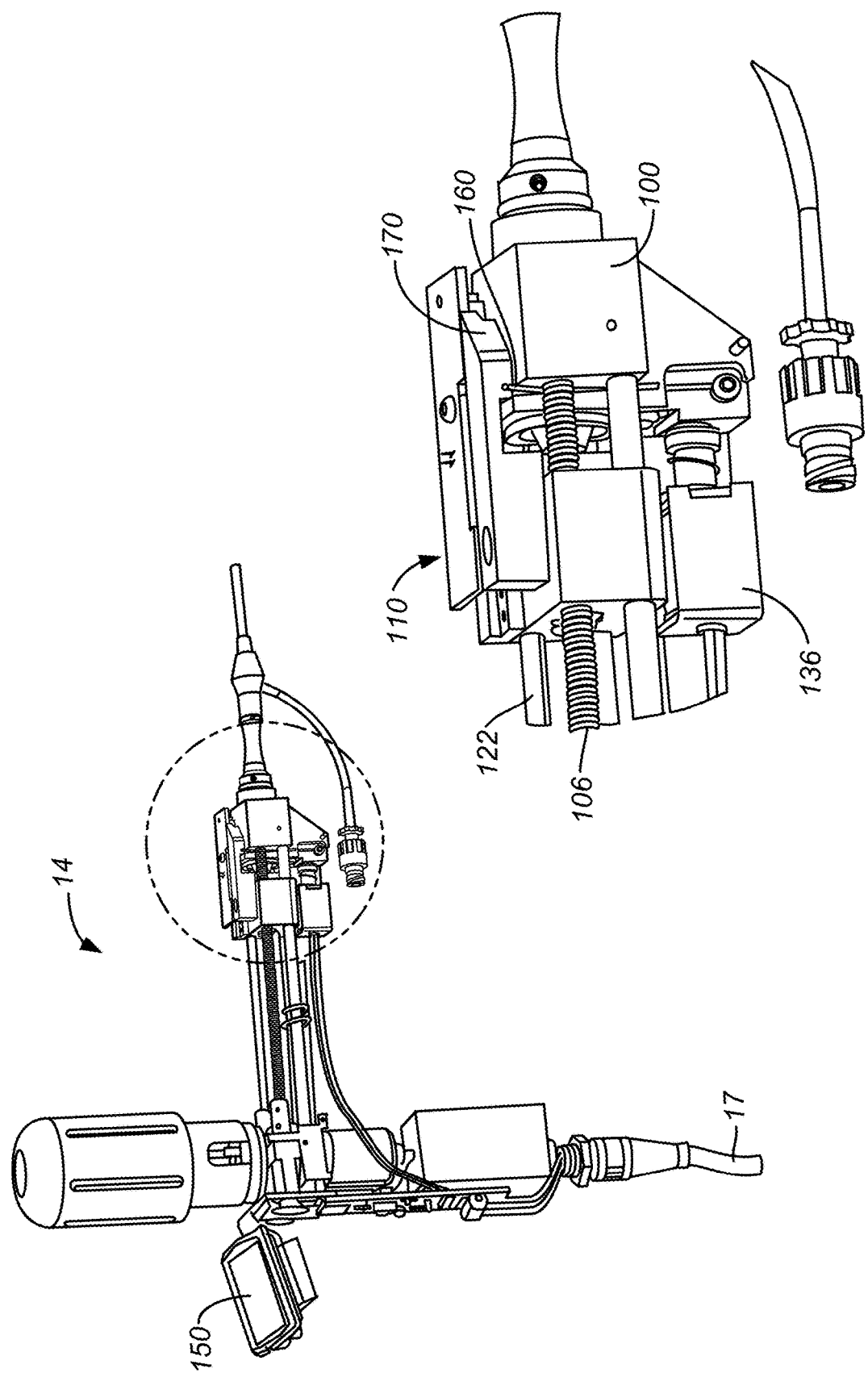
FIG. 13 shows the structure of FIG. 12 in a catheter connector disconnect state.
Figure 13A:
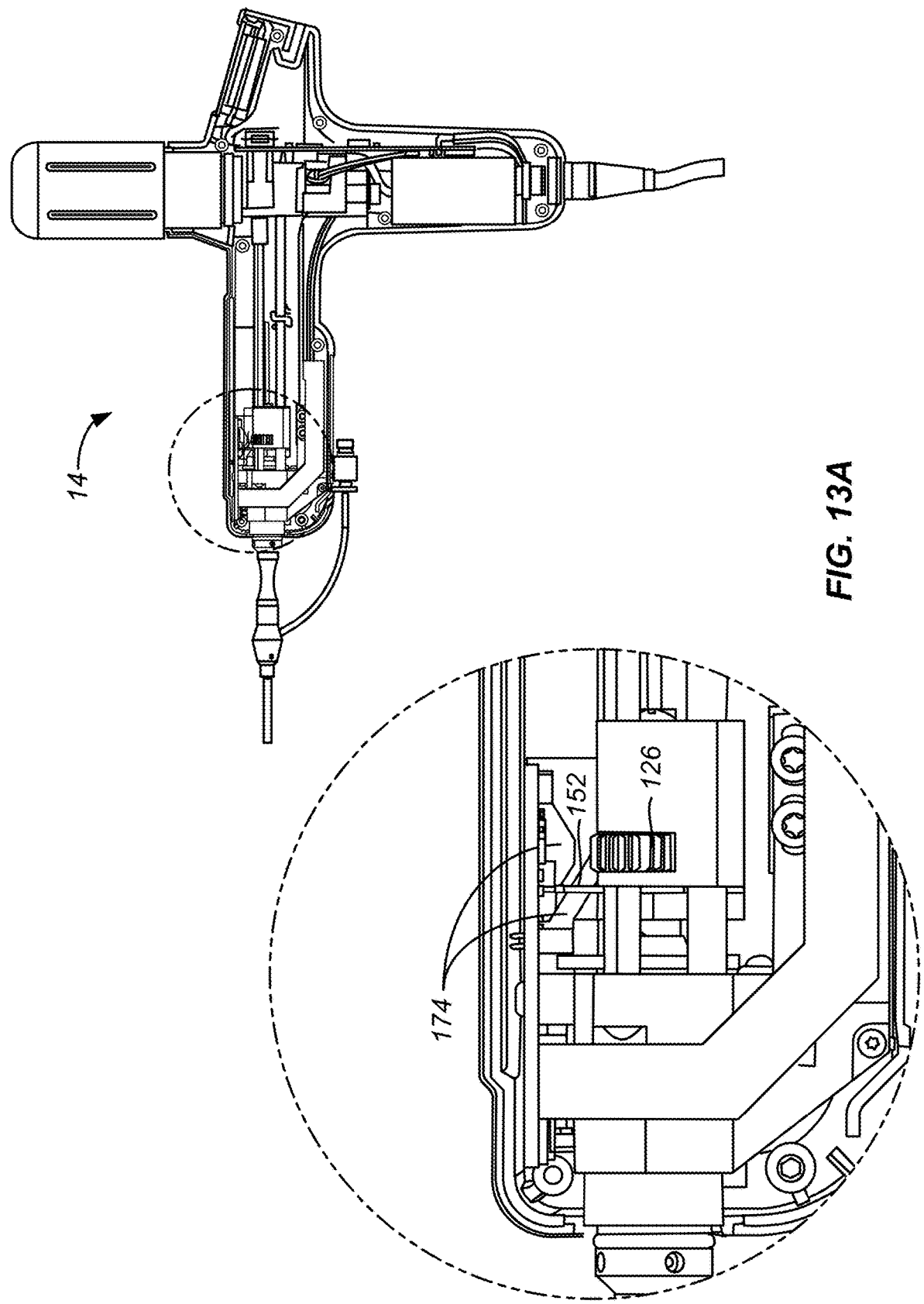
FIG. 13A is a left side partial cross-sectional view of the handle assembly in the catheter-disconnect state of FIG. 13.
Figure 13B:
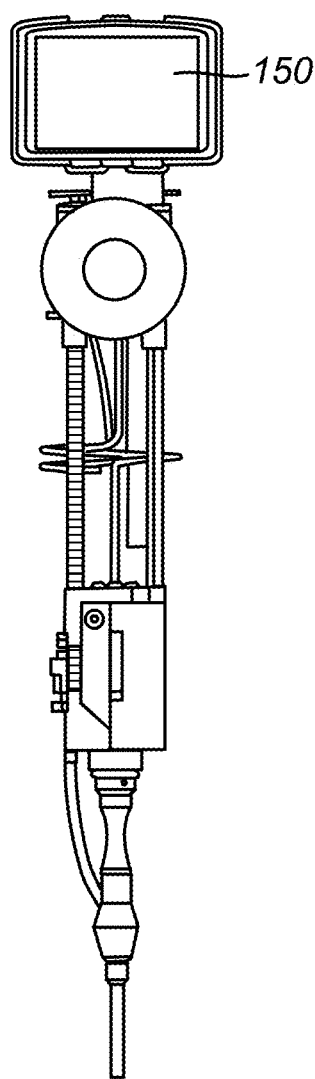
FIG. 13B and 13C are top views of the structure of FIG. 13.
Figure 13C:
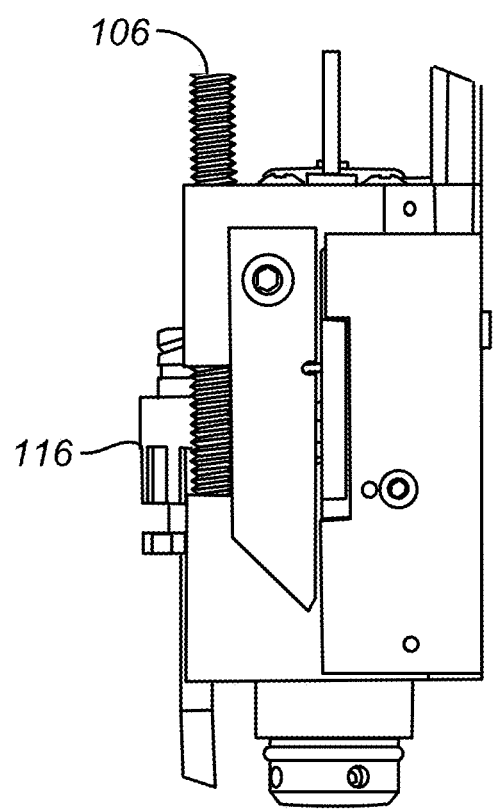

FIGS. 13, 13A, 13B and 13C show handle assembly 14 in a connector disconnect state with traveler 110 moved in the distal direction, that is to the right in FIG. 13, to a catheter disconnect position. Doing so causes connector locking wire 160, mounted to controller connector 100, be deflected outwardly by the engagement of ramp 170, ramp 170 being a part of traveler 110, so that it moves out of body locking slot 74 as shown in FIG. 8E. Continued movement of traveler 110 to the catheter disconnect position also causes catheter plug locking wire 152, which moves with traveler 110, to be engaged by a ramp 174 causing plug locking wire 152 to move out of plug locking slot 84 from the plug engaged position of FIGS. 9B and 9C to the plug disengaged position of FIGS. 8C and 8D. Ramp 174 is part of controller connector 100. The distal motion of traveler 110 to the catheter disconnection position results in the partial rejection of connector 22 from first connector element 99 of controller connector 100. Connector body 23 is released first, followed by the release of plug 38. Accordingly, examples of ablation assembly 10 provide for the automatic detachment/ejection of connector 22 from handle assembly 14.

When a nitrous cartridge 96 is removed from handle assembly 14, it is important to safely deal with any remaining refrigerant within the cartridge. Handle assembly 14 has a liquid path, shown in FIGS. 14, 14A, 14B, and 14C, for the passage of liquid refrigerant from a region 176 adjacent to the tip 178 to a refrigerant venting chamber 180. Liquid path includes first, second and third portion 182, 184, 186. First portion 182 extends to region 176, and second portion 184 connects first portion 182 to third portion 186. Third portion 186 extends to refrigerant venting chamber 180. The excess refrigerant released from refrigerant source 96, typically nitrous oxide, when the cartridge is removed from handle assembly 14 is typically in liquid form. Refrigerant venting chamber 180 is filled with a foam material, typically open cell polyurethane foam, and has an entrance path 188 and an exit path 190 formed in the foam material. Exit path 190 opens into the interior of handle assembly 14 at an exit port 192. Under the reduced pressure within venting chamber 180, the liquid refrigerant is absorbed by the foam material and transformed into a gas for collection within exit path 190, passage through exit port 192 into the interior of handle assembly body 90. The gas exits through one or more of the exhaust ports 133, 135 in the handle assembly body.

Figure 15:
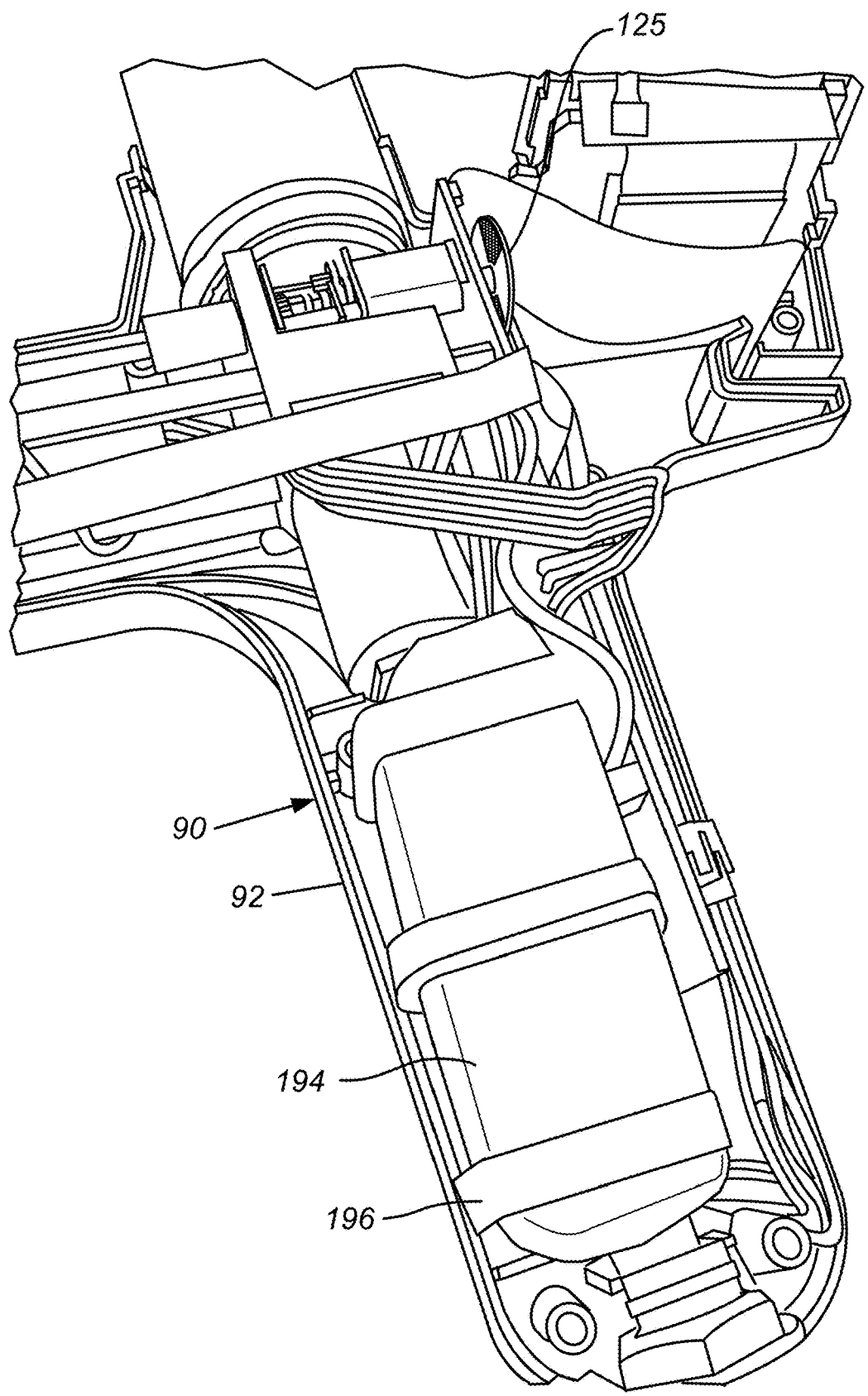
FIG. 15 illustrates how the handgrip portion of the handle assembly body is thermally insulated from the refrigerant venting chamber.

The transformation of the liquid refrigerant into a gas causes refrigerant venting chamber 180 to become quite cold. To prevent handgrip portion 92 of handle assembly body 90 from becoming too cold, refrigerant venting chamber 180 is wrapped with a thermal insulation material 194, see FIG. 15, and is spaced apart from the handle assembly body by insulating spacers 196. In this example 3 insulating spacers 196 are used to maintain a gap between refrigerant venting chamber 180 and handgrip portion 92 of handle assembly body 90. Thermal insulation material can be made of, for example, air, and insulating spacers 196 can be made of, for example, neoprene.

The pressure within the balloon 24 is communicated to a pressure transducer 143 in the controller connector 100. See FIGS. 9E and 9F. The pressure detecting lumen 32 of the catheter is fluidly coupled to the pressure transducer 143 in the controller through the pressure detecting passage 66 and the pressure detection port 68 of the connector body 23. The pressure detecting passage 66 and the pressure detecting port 68 are shown in FIG. 7B. The O-rings 88 on either side of the pressure detection port 68 form a seal within the controller connector 100, as shown in FIG. 9A. Pressure transducer 143 is coupled to controller 50 to provide a pressure signal thereto. For clarity connection wires from components to the controller 50 are omitted from the figures.

Figure 18:
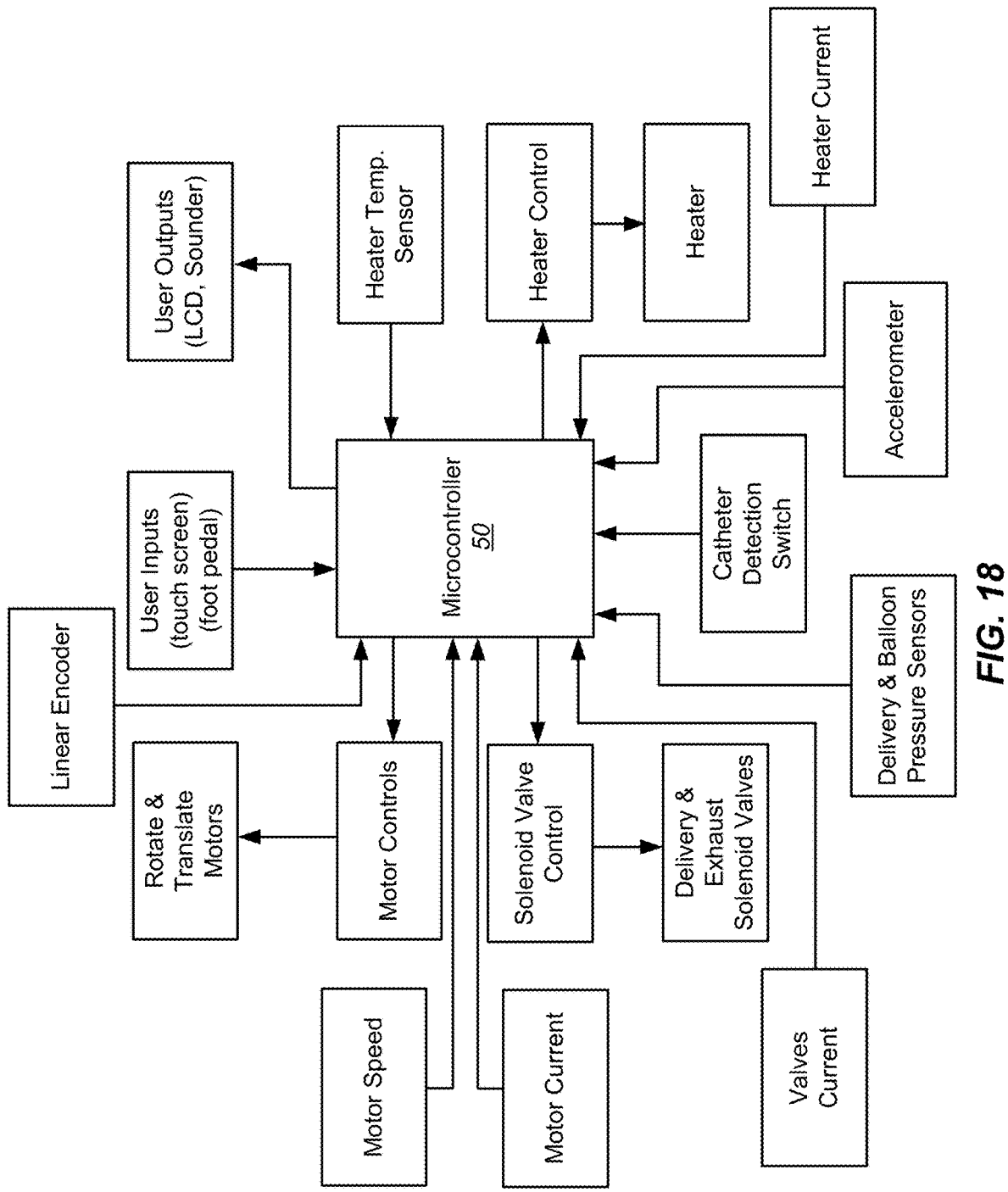
FIG. 18 is a simplified controller hardware architecture design chart.

The controller 50 may be used to control the delivery of refrigerant and the rotation and translation of the delivery tube 30 and diffuser 36 within the balloon 24. The controller 50 includes circuitry connected to components including the foot pedal assembly 15, delivery solenoid 130, exhaust solenoid 136, linear drive motor 104, rotation motor 120, counter wheels 119, 125, pressure transducers 141, 143, heater 102, thermistor 137, optical sensor 165, current sensors, and accelerometer, In embodiments, during release of refrigerant into the balloon 24 the controller 50 generates a pressure response curve from pressure data from the pressure transducer 141, which correlates to the inner diameter of the lumen to be treated. The controller 50 uses a pressure algorithm to determine the rate of speed for the linear actuator appropriate for treatment. In embodiments, a strain gauge or gauges on the balloon 24 may be used by the controller 50 to derive balloon diameter which corresponds to the inner diameter of the treated lumen. In embodiments the controller may be attached to forms of user interfaces in addition to or instead of those provided by foot pedal assembly 15 and LCD display 150, including buttons on the housing of the handle assembly and remote touch displays. FIG. 18 is a simplified diagram showing the basic organization of control electronics of the controller 50. In embodiments, the control electronics may be connected to additional components including user outputs including lights and displays, additional temperature sensors, heater controllers, accelerometers, detector switches, and solenoid valves. The controller may contain treatment algorithms and the inputs of components may be used by the algorithms to adjust treatment parameters, for example duration, flow rate of refrigerant, translation distance and speed, and rotational angles and speed.

In embodiments, the catheter 12 may include an RFID tag or chip 198, see FIG. 9A, identifying properties of the catheter including size of balloon, angle of spray of diffuser. The controller 50 may receive this information from an RFID reader 200 in the handle assembly 14 and input the information into a treatment algorithm to adjust treatment parameters depending on the properties of the attached catheter. The RFID may be used for authentication purposes. For example, a non-conforming catheter (e.g. reused or overused catheter, or catheter made by an uncertified manufacturer) may be detected by the controller and the controller will lock out the device from operating with the non-conforming catheter attached. The RFID may further be used for orientation purposes to ensure catheter is oriented properly. The number of times or the length of use of a particular catheter 12 can also be monitored or controlled by providing unique identification information for each catheter to its associated RFID chip 198. It is preferred that connector body 23 be made of a material, such as polycarbonate, which facilitates the interrogation of the RFID chip 198 by the RFID reader 200. According to embodiments discussed herein, handle assembly 14 can be considered universal handle for use with a wide variety of catheters 12 because information regarding the catheter can be automatically provided to controller 50 within handle assembly 14 through the use of RFID chips 198 and RFID reader 200.

In embodiments, the user may select a treatment algorithm prior to initiating the treatment. Additionally the user may be able to input various parameters to be used in the selected treatment algorithm. The information may include patient data, catheter information and number of treatments performed. The user interface for selecting and setting a treatment may the input on a separate device to permit programming remotely with reception by the controller wirelessly, wired or, for example, via a removable memory card.

The controller may record the number of uses of a catheter and save this information, or transmit this information to a central database to ensure no overuse of catheters. In embodiments, RFID tags on the catheter may be writeable so the controller can program catheter to be read in the future. The written material may include a lockout or a time of last use.

Figure 16:
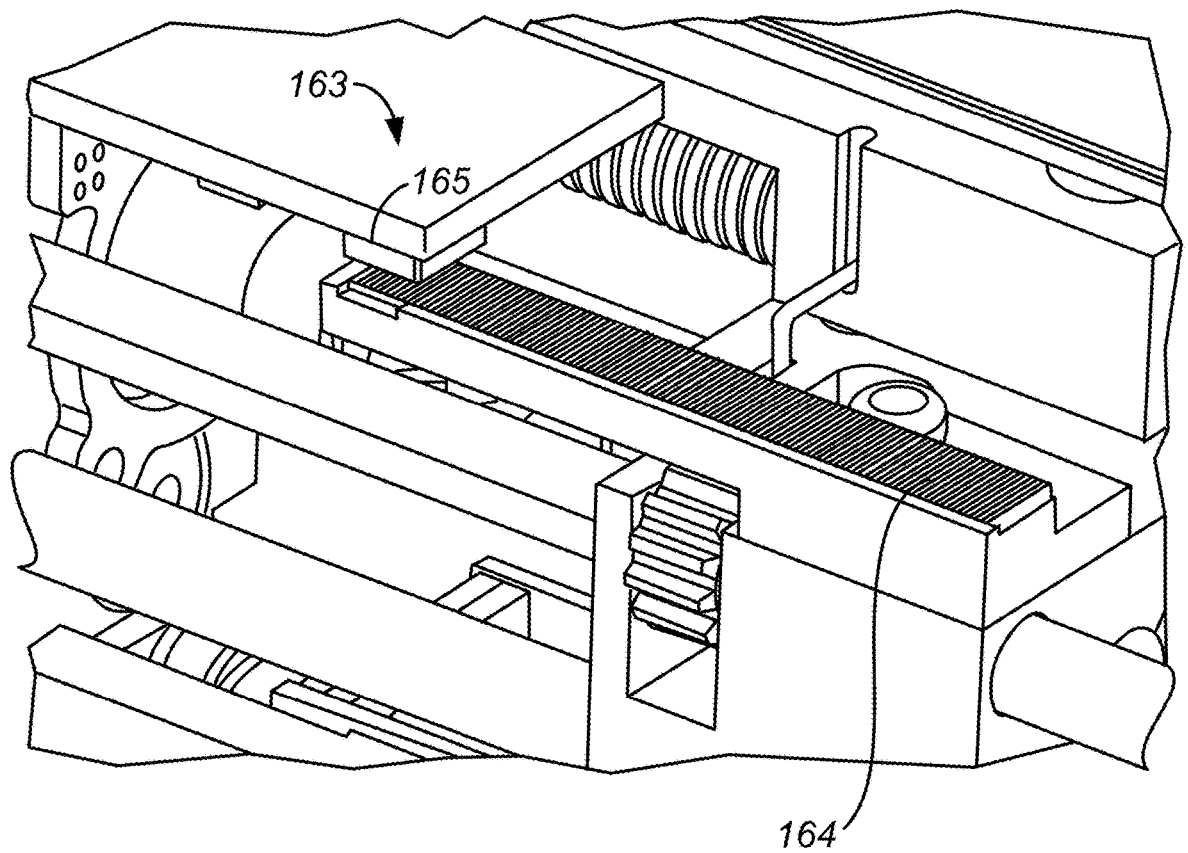
FIGS. 16 and 17 illustrate a linear positioner used to ensure the proper linear position of the traveler relative to the controller connector.
Figure 17:
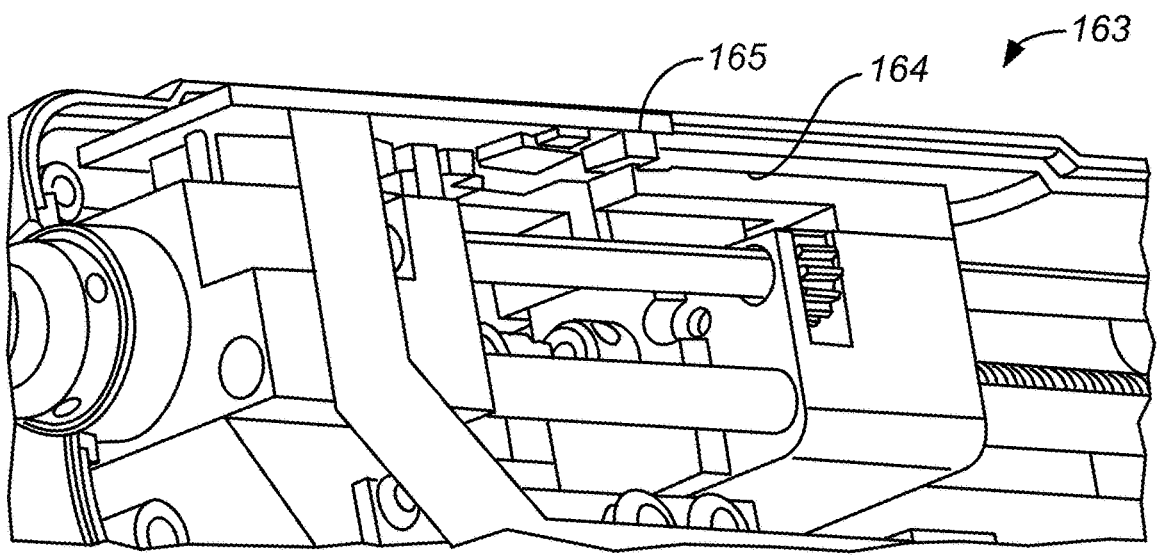

The following is an example of an ablation procedure. A cryogenic ablation catheter 12 is selected according to the treatment to be undertaken. An endoscope is inserted in the esophagus of a patient. Ablation catheter 12 with the plug 38 in the most distal position as shown in FIG. 2A is inserted into the proximal end 5 of the channel 8 of endoscopic tube 3. The plug 38 in the most distal position causes the diffuser 36 to push the flexible tip 48 away from the catheter shaft 16 causing the deflated balloon 24 to be in tension. The catheter 12 is inserted through the channel 8 until the balloon 24 exits the distal end 7. Using the monitor attached to the endoscope the user is able to see the balloon exit. With the system powered on, traveler 110 is translated by linear drive motor 104 to the connector load position of FIG. 9. A linear positioner 163 is used to ensure the proper linear position of traveler 110 relative to controller connector 100. Traveler 110 has a length of finely spaced lines 164, such as about 250 per inch, which are sensed by one or more optical sensors 165 carried by controller connector 100. See FIGS. 16 and 17.

The user selects, if desired, a treatment algorithm, inputs any necessary parameters, and taps on the refrigerant delivery foot pedal 132 to initially inflate the balloon 24. This initial inflation is required to visualize the location of target site relative to the lesion to be ablated. This initial inflation may include translating the diffuser to a position to allow for the balloon to be relaxed and no longer in tension. Instead of using a small amount of refrigerant to initially inflate the balloon 24, a syringe mounted to syringe coupler 56 could be used to initially inflate the balloon. An example of this position is shown in FIG. 2B. This can be followed by a short burst of refrigerant spray delivered onto inner surface of balloon 24 which inflates the balloon and allows the user to visually determine the location of the target site using the endoscope because of the freezing which occurs at tissue near the target site. If necessary, balloon 24 can be repositioned axially; this may or may not require the partial deflation balloon 24 followed by re-inflation of the balloon.

Once balloon 24 is properly positioned and inflated so that the nozzle ports 40 are directed at a portion of the lesion or other tissue to be cryogenically treated at the most distal end of the balloon, refrigerant is delivered to the diffuser to be sprayed on the interior wall of the balloon 24. While the refrigerant is being sprayed the diffuser can be translated toward the proximal end of the balloon or rotated about its axis using the pedal assembly 15. The flow rate of refrigerant, rotation rate and translation rate of the diffuser 36 are ideally set so that an ideal amount of refrigeration energy is received by each portion of the lesion to ensure ablation of the entire desired area. If the movement of the delivery tube assembly jams for any reason the controller will stop the delivery of refrigerant to prevent over ablation of tissue that may cause damage. Jams can be detected from the counter wheel 119 or monitoring current to the motors 104, 120.

Due to the direction of exhaust, it is beneficial to begin ablation from the distal end of the balloon as disclosed above because cool exhaust gas will pass over portions of the balloon interior surface that will subsequently be sprayed by refrigerant. This flow of exhaust gas therefore has a pre cooling effect which reduces the temperature prior to delivery which allows for less refrigerant to be used to achieve a desired ablation temperature. This pre-cooling effect is factored into the treatment algorithms.

The above descriptions may have used terms such as proximal, distal, above, below, top, bottom, over, under, et cetera. These terms may be used in the description and claims to aid understanding of the invention and not used in a limiting sense.

While implementations of the technology are disclosed by reference to the preferred embodiments and examples detailed above, it is to be understood that these examples are intended in an illustrative rather than in a limiting sense. It is contemplated that modifications and combinations will occur to those skilled in the art, which modifications and combinations will be within the spirit of the technology disclosed and the scope of the following claims. For example, in some situations it may be desired to rotate and translate simultaneously. In some examples such movement may be limited to preprogrammed movement rather than providing foot pedal assembly with such functionality.

One or more elements of one or more claims can be combined with elements of other claims.

The following clauses describe aspects of various examples of the technology described in this application.

1. An ablation assembly comprising:
   a controller assembly 13 comprising a handle assembly 14, a controller 50, and a user control assembly 15 coupled to the controller, the handle assembly comprising a first connector element 99;

a cryogenic ablation catheter 12 comprising:
a catheter shaft 16 having proximal and distal ends and a catheter shaft lumen extending between the proximal and distal ends;
a connector 22 at the proximal end of the catheter shaft selectively connected to the first connector element of the handle assembly, the connector comprising a connector body 23 and a second connector element 38, the first and second connector elements being mating connector elements;
an expandable and collapsible balloon 24 mounted to the distal end of the catheter shaft, the balloon having an inner surface defining a balloon interior;
a delivery tube assembly comprising:
a delivery tube 30 housed within the catheter shaft for axial and rotational movement relative to the catheter shaft, the delivery tube having a proximal end connected to the second connector element; and
a diffuser 36, within the balloon, fluidly coupled to the delivery tube; and
the handle assembly comprising:
a handle assembly body 90;
a controller connector 100 mounted to the handle assembly body and defining the first connector element, the connector body securable to the controller connector;
a traveler 110 movably mounted to the handle assembly body for movement along an axis towards and away from the controller connector, the second connector element securable to the traveler for axial movement therewith;
a refrigerant fluid source 96 selectively fluidly coupled to a delivery line 118 by the refrigerant controller 130, 128, the delivery line having a distal end connected to the traveler, whereby the refrigerant delivery source can be fluidly coupled to the delivery tube at the second connector element;
a linear driver 104, 108, 106 operably coupled to the traveler for moving the traveler along the axis;
a rotary motion driver 120, 124, 122 operably coupled to the second connector element for selective rotation of the second connector element and the proximal end of the delivery tube therewith about the axis;
the user control assembly operably coupled to the refrigerant controller, the linear driver and the rotary motion driver, the user control assembly comprising user inputs permitting the user to actuate the refrigerant controller, the linear driver and the rotary motion driver;
whereby the user can control the rotation and translation of the diffuser within the balloon to direct refrigerant outwardly in a desired pattern towards the inner surface of the balloon according to the size and location of the treatment site.

2. The assembly according to clause 1, wherein the user control assembly 15 comprises a foot pedal assembly 15 spaced apart from the handle assembly 14 and connected to the handle assembly by a line 17, the foot pedal assembly comprising foot actuated input devices.

3. The assembly according to clause 2, wherein the foot pedal assembly 15 comprises a left movement foot pedal 140, a right movement foot pedal 142 and movement mode button 144 by which the user can change the mode of operation of the left and right movement foot pedals to actuate either the linear driver or the rotary motion driver.

4. The assembly according to clause 3, wherein:
the cryogenic ablation catheter 12 comprises an exhaust lumen 28 between the catheter shaft 16 and the delivery tube 30, the exhaust lumen having a distal end opening into the interior of the balloon;
the foot pedal assembly 15 comprises:
a refrigerant delivery foot pedal 132 by which a user can actuate the refrigerant controller to supply refrigerant to the balloon 24; and
a deflation button 134;
the handle assembly comprises an exhaust solenoid 136 operably coupled to the deflation button to permit the user to selectively exhaust gas from the balloon interior.

5. The assembly according to any of clauses 1-4 wherein:
the traveler is positionable along the axis at a first, eject position, a second, load position, and at a range of third, operational positions, the first, eject position being closest to the controller connector, the second, load position being between the first, eject positions and the third, operational positions, and further comprising:
means for automatically securing the connector body 23 to the controller connector 100 and the second connector element 38 to the traveler 110 when the connector is inserted into the connector receptacle and the traveler is at the second, load position; and
means for automatically releasing the connector body from the controller connector and the second connector element from the traveler when the traveler is at the first, eject position to permit removal of the connector from the handle assembly body.

6. The assembly according to clause 5, wherein:
the automatically securing means comprises means for simultaneously automatically securing the connector body 23 to the controller connector 100 and the second connector element 38 to the traveler 110 when the connector is inserted into the connector receptacle and the traveler is at the second, load position; and
the automatically releasing means comprises means for automatically releasing the connector body from the controller connector as the traveler moves to the first, eject position, and thereafter releasing the second connector element from the traveler to permit removal of the connector from the handle assembly body.

7. The assembly according to any of clauses 1-6 wherein:
the refrigerant fluid source 96 comprises a removable and replaceable refrigerant cartridge having a refrigerant discharge portion/tip 178 through which refrigerant can pass to the delivery line 118 via the refrigerant controller 130, 128 when the refrigerant fluid source is at an operational position;
the handle assembly body 90 comprises a refrigerant venting chamber 180 and a pathway 182, 184, 186 fluidly connecting the interior of the refrigerant venting chamber to a region adjacent to the tip of the refrigerant cartridge when the refrigerant cartridge has been displaced from the operational position during removal of the refrigerant cartridge from the handle assembly body 90;
whereby residual liquid refrigerant from the refrigerant cartridge can flow into the refrigerant venting chamber for transformation into a refrigerant gas, the refrigerant venting chamber having an exit port 192 to permit the refrigerant gas to exit the refrigerant venting chamber.

8. The assembly according to clause 7, wherein the exit port 192 opens into the handle assembly body 90, the handle assembly body having a plurality of exhaust ports 133, 135 opening into the ambient atmosphere.

9. The assembly according to any of clauses 1-8, wherein the traveler 110 is slideably supported on at least one bearing shaft 112 for movement of the traveler along the axis.

10. The assembly according to any of clauses 1-4 and 7-9, wherein:
the traveler is positionable along the axis at a first, eject position, a second, load position, in the range of third, operational positions, the first, eject position being closest to the controller connector, the second, load position being between the first, eject positions and the third, operational positions, and further comprising:
the rotary motion driver comprises:
a rotation motor 120 drivingly connected to a non-cylindrical rotation shaft 122;
a drive gear 126 mounted to traveler 110 for axial movement with the traveler, the drive gear also slideably mounted to the rotation shaft, whereby rotation of the rotation shaft causes the drive gear to rotate while axial movement of the traveler causes the drive gear to slide along the rotation shaft; and
gear teeth 85 formed on second connector element 38 and rotatably coupled to the drive gear when the traveler is in either the second, load position or the third, operational position, so that rotation of the drive gear causes the second connector element 38 to rotate; and
the linear driver comprises a linear drive motor 104 connected to a threaded shaft 106 by a threaded shaft coupler 108, the threaded shaft threadably engaging the traveler 110 so that rotation of the threaded shaft causes the traveler to move axially.

11. The assembly according to any of clauses 1-10, wherein:
the connector 22 comprises an RFID device 198 containing information relating to the cryogenic ablation catheter 12; and
the handle assembly comprises an RFID reader 200 used to obtain information from the RFID device.

12. The assembly according to clause 11, wherein the RFID reader 200 is mounted to the controller connector 100, the connector body 23 being made of PEEK to enhance the communication between the RFID reader and the RFID device 198.

13. The assembly according to any of clauses 1-12, wherein the controller assembly comprises a controller 50, and the user control assembly is operably coupled to the refrigerant controller, the linear driver, and the rotary motion driver through the controller.

14. The assembly according to clause 13, wherein:
a pressure detecting lumen 32 extends along the catheter shaft 16 fluidly coupling the balloon interior and the connector body 23; and
the controller 50 is configured to use input received from a pressure transducer 143 operably coupled to the pressure detecting lumen 32 through the connector body 23 to detect a pressure within the balloon 24.

15. The assembly according to clause 13, wherein the controller 50 is configured to monitor the pressure and temperature of the refrigerant fluid source 96, whereby the status of the refrigerant can be monitored.

16. The assembly according to any of clauses 1-15, wherein the first connector element comprises a connector receptacle and the second connector element comprises a plug.

17. An ablation assembly comprising:
a handle assembly 14; and
a catheter 12 comprising:
a catheter shaft 16 having distal and proximal ends;
a balloon 24 at the distal end of the catheter shaft;
a connector 22 at the proximal end of the catheter shaft;
a delivery tube 30 extending between the balloon and the proximal end of the catheter shaft; and
the connector comprising a connector body 23 secured to the proximal end of the catheter shaft and a plug 38 secured to the delivery tube, the plug and delivery tube therewith movable axially and rotationally relative to the catheter shaft;
the handle comprising an open portion for receipt of the plug and at least a portion of the connector body; and
a connector locking assembly comprising:
a connector body locking slot 74 formed in and circumscribing the connector body 23;
a plug locking slot 84 formed in and circumscribing the plug 38;
a connector body locking element 160 mounted to the handle and positioned to engage the connector body locking slot 74 when the connector 22 is in a load state;
a plug locking element 152, 154 mounted to the handle and positioned to simultaneously engage the plug locking slot 84 when the connector is in the load state, thereby simultaneously automatically connecting the plug 38 and the connector body 23 to the handle to place the connector in a load state prior to use; and
a connector body locking element 160 mounted to the handle and positioned to disengage from the body locking slot when the connector is being placed in an eject state, and a plug locking element 152, 154 mounted to the handle and positioned to disengage from the body locking slot when the connector is in the eject state, thereby automatically releasing the connector body 23 and thereafter the plug 38 from the handle to permit the connector to be removed from the handle.

18. The ablation assembly according to clause 17, wherein the connector body locking element comprises a first spring 160 and the plug locking element comprises a second spring 152, 154.

19. The ablation assembly according to clause 18, wherein:
the connector body 23 comprises a tapered surface 162 engageable by the first spring 160 when the connector is placed into the load state; and
the plug 38 comprises a tapered surface 156 engageable by the second spring 152, 154 when the connector is placed into the load state.

20. The ablation assembly according to either of clauses 18 or 19, wherein:
the connector locking assembly comprises a ramp 170 engageable by the first spring 160 when the connector is placed into the eject state; and
the connector locking assembly comprises a ramp 174 engageable by the second spring 152, 154 when the connector is placed into the load state.

21. An ablation assembly comprising:
a handle assembly 14; and
a catheter 12 comprising:
a catheter shaft 16 having distal and proximal ends;
a balloon 24 at the distal end of the catheter shaft;
a connector 22 at the proximal end of the catheter shaft;
a delivery tube 30 extending between the balloon and the proximal end of the catheter shaft; and
the connector comprising a connector body 23 secured to the proximal end of the catheter shaft and a plug 38 secured to the delivery tube, the plug and delivery tube therewith movable axially and rotationally relative to the catheter shaft;

the handle comprising an open portion for receipt of the plug and at least a portion of the connector body; and
a connector locking assembly comprising:
means for simultaneously automatically connecting the plug 38 (84, 152, 154, 156, 158) and the connector body 23 (160, 174, 162) to the handle to place the connector in a load state prior to use; and
means for automatically releasing the connector body (74, 110, 160, 170) and thereafter the plug (84, 110, 152, 154, 174) from the handle to place the connector in an eject state to permit the connector to be removed from the handle.

22. A handle assembly 14 for use with a cryogenic ablation assembly 10 comprising:
a handle body 90 having an interior;
a refrigerant fluid source 96 within the interior comprising a removable and replaceable refrigerant cartridge 96 from which refrigerant can pass for use by the cryogenic ablation assembly 10 when the refrigerant fluid source is at an operational position, the refrigerant source comprising a refrigerant discharge portion 178;
the handle body 90 containing a refrigerant venting chamber 180 and a pathway 182, 184, 186 fluidly connecting the interior of the refrigerant venting chamber to a region adjacent to the refrigerant discharge portion of the refrigerant cartridge when the refrigerant cartridge has been displaced from the operational position during removal of the refrigerant cartridge from the handle body 90;
the handle body comprising an exhaust port 133, 135 opening into the ambient atmosphere;
whereby residual liquid refrigerant from the refrigerant cartridge can flow into the refrigerant venting chamber for transformation into a refrigerant gas, the refrigerant venting chamber having an exit port 192 to permit the refrigerant gas to exit the refrigerant venting chamber and into a region external of the refrigerant venting chamber 180 and within the handle body 90, for passage through the exhaust port to the ambient atmosphere.

23. The handle assembly according to clause 22, wherein:
the refrigerant venting chamber 180 is filled with a material with an entrance path 188 and an exit path 190 formed in the material, the entrance path connected to the pathway; and
the exit path 190 terminating at the exit port 192;
whereby under a reduced pressure within the refrigerant venting chamber 180, the liquid refrigerant is absorbed by the foam material and transformed into a gas for collection within the exit path 190, passage through exit port 192 into said region external of the refrigerant venting chamber 180 and within the handle body 90.

24. The handle assembly according to either of clauses 22 or 23, further comprising:
a thermal insulation material 194 between the refrigerant venting chamber 180 and the handle body 90; and
spacers 196 between the thermal insulation material 194 and the handle body 90.

25. Catheter identification structure for a cryogenic ablation assembly 10 of the type including a handle assembly 14 and a catheter assembly, the catheter 12 comprising a catheter shaft 16 having distal and proximal ends, a connector 22 at the proximal end of the catheter shaft, the handle assembly 14 comprising an open portion for receipt of at least a portion of the connector, the catheter identification structure comprising:

an RFID device 198 carried by the connector 22 containing information relating to the catheter 12; and
an RFID reader 200 carried by the handle assembly used to obtain information from the RFID device.

26. The structure according to clause 25, wherein the connector 22 comprises a connector body 23 made of PEEK to enhance the communication between the RFID reader 200 and the RFID device 198.

Any and all patents, patent applications and printed publications referred to above are incorporated by reference.

What is claimed is:

1. A catheter assembly, comprising:
a catheter shaft having proximal and distal ends and a catheter shaft lumen extending between the proximal and distal ends;
a first connector secured to the proximal end of the catheter shaft;
an expandable and collapsible balloon at the distal end of the catheter shaft, the balloon having an inner surface defining a balloon interior;
a delivery tube, extending into the balloon interior through, and movable within, the first connector and the catheter shaft lumen, the delivery tube having a proximal end and a distal end disposed in the balloon interior;
a diffuser, in the balloon interior, secured to and fluidly coupled with the distal end of the delivery tube;
a second connector secured to the proximal end of the delivery tube, the second connector movable for both axial and rotary motion of the second connector, the delivery tube and the diffuser relative to the first connector, the catheter shaft lumen and the balloon interior; and
a handle configured to connect to the second connector and provide the axial and rotary motion of the second connector, the delivery tube and the diffuser,
wherein, when the second connector is connected to the handle for providing the axial and rotatory motion of the second connector, the delivery tube and the diffuser, the second connector and the diffuser axially move along an axis while the handle remains the same axial distance from the catheter shaft.

2. The catheter assembly according to claim 1, wherein the second connector includes a slot circumscribing the second connector, adapted to receive a spring coupler to secure the second connector to a linear driver.

3. The catheter assembly according to claim 1, wherein the second connector includes gear teeth circumscribing the second connector, adapted to receive and be rotatably coupled with gear teeth of a complementary gear of a rotary motion driver to provide the rotary motion of the second connector.

4. The catheter assembly according to claim 1, wherein the second connector includes a slot circumscribing the second connector, adapted to receive a spring coupler to secure the second connector to a linear driver, and gear teeth arranged around a longitudinal axis of the second connector, adapted to receive and be rotatably coupled with gear teeth of a complementary gear of a rotary motion driver to provide rotary motion of the second connector.

5. The catheter assembly according to claim 1, wherein the first connector includes a slot circumscribing the first connector, adapted to receive a spring coupler to secure the first connector to a handle.

6. The catheter assembly according to claim 1, wherein the handle includes a receptacle adapted to secure the first connector to the handle and to couple the second connector to a linear driver and a rotary motion driver.

7. The catheter assembly according to claim 1, including:
a linear driver and a rotary motion driver mounted on the handle;
a receptacle adapted to secure the first connector to the handle;
a traveler coupled to the linear driver and to the rotary motion driver, the traveler being movable in an axial direction by the linear driver and including a drive gear rotatable by the rotary motion driver while the traveler is moved axially; and
a spring coupler connected to the traveler to secure the second connector to the traveler and to the drive gear on the traveler.

8. The catheter assembly according to claim 7, wherein the second connector includes gear teeth complementary to the drive gear on the traveler.

9. The catheter assembly according to claim 1, including:
a pressure delivery lumen extending along the catheter shaft fluidly coupling the balloon interior; and
a pressure transducer operably coupled to the pressure delivery lumen to detect a pressure in the balloon interior.

10. An ablation assembly comprising:
a catheter shaft having proximal and distal ends and a catheter shaft lumen extending between the proximal and distal ends;
a first connector secured to the proximal end of the catheter shaft;
an expandable and collapsible balloon at the distal end of the catheter shaft, the balloon having an inner surface defining a balloon interior;
a delivery tube, extending into the balloon interior through, and movable within, the first connector and the catheter shaft lumen, the delivery tube having a proximal end and a distal end disposed in the balloon interior;
a diffuser, in the balloon interior, secured to and fluidly coupled with the distal end of the delivery tube;
a second connector secured to the proximal end of the delivery tube, the second connector movable for both axial and rotary motion of the second connector, the delivery tube and the diffuser relative to the first connector, the catheter shaft lumen and the balloon interior;
a handle comprising an open portion for receipt of the second connector and at least a portion of the first connector and configured to provide the axial and rotary motion of the second connector, the delivery tube and the diffuser; and
a connector locking assembly comprising:
a first locking slot formed in and circumscribing the first connector;
a second locking slot formed in and circumscribing the second connector;
a first locking element mounted to the handle and positioned to engage the first locking slot in a load state; and
a second locking element movable within including a coupler to simultaneously engage the second locking slot in the load state, thereby simultaneously automatically connecting the second connector and the first connector to the handle in a load state prior to use,
wherein the first locking element is positioned to disengage from the first locking slot when in an eject state, and the second locking element is positioned to disengage from the second locking slot in the eject state, thereby automatically releasing the catheter shaft and delivery tube from the handle, and
wherein, when the second connector is connected to the handle for providing the axial and rotatory motion of the second connector, the delivery tube and the diffuser, the second connector and the diffuser axially move along an axis while the handle remains the same axial distance from the catheter shaft.

11. The ablation assembly according to claim 10, wherein the first locking element comprises a first spring and the second locking element comprises a second spring.

12. The ablation assembly according to claim 11, wherein:
the first connector comprises a tapered surface engageable by the first spring in the load state; and
the second connector comprises a tapered surface engageable by the second spring in the load state.

13. The ablation assembly according to claim 10, including;
means for simultaneously automatically connecting the first and second connectors to the handle to place the connectors in a load state prior to use; and
means for automatically releasing the first connector and thereafter the second connector from the handle to place the connector in an eject state to permit the connector to be removed from the handle.

14. A method of operating a catheter assembly including a catheter shaft having proximal and distal ends, a first connector secured to the proximal end of the catheter shaft, an expandable and collapsible balloon at the distal end of the catheter shaft, the balloon having an inner surface defining a balloon interior, a delivery tube, extending into the balloon interior through, and movable within, the first connector and the catheter shaft, the delivery tube having a proximal end and a distal end disposed in the balloon interior, a diffuser, in the balloon interior, secured to and fluidly coupled with the distal end of the delivery tube, a second connector secured to the proximal end of the delivery tube, the second connector movable for both axial and rotary motion of the second connector, the delivery tube and the diffuser relative to the first connector, the catheter shaft lumen and the balloon interior, and a handle configured to connect to the second connector and provide the axial and rotary motion of the second connector, the delivery tube and the diffuser, the method comprising:
manipulating the second connector to cause simultaneous axial and rotary motions of the delivery tube and the diffuser relative to the first connector and the balloon interior, while supplying a refrigerant to the inner surface of the balloon interior through the diffuser during the axial and rotary motion of the diffuser,
wherein, when the second connector is connected to the handle for providing the axial and rotatory motion of the second connector, the second connector and the diffuser axially move along an axis while the handle remains the same axial distance from the catheter shaft.

15. The method of claim 14,
wherein the second connector is manipulated by a linear driver to cause the axial motion of the delivery tube and the diffuser, wherein the second connector is manipulated by a rotary motion driver to cause the rotary motion of the delivery tube and the diffuser, and
wherein the refrigerant is supplied by a refrigerant controller.

16. A non-transitory computer readable recording medium having computer instructions for controlling an ablation assembly recorded thereon,
wherein the ablation assembly includes:
- a catheter shaft having proximal and distal ends;
- a first connector secured to the proximal end of the catheter shaft;
- an expandable and collapsible balloon at the distal end of the catheter shaft, the balloon having an inner surface defining a balloon interior;
- a delivery tube, extending into the balloon interior through, and movable within, the first connector and the catheter shaft, the delivery tube having a proximal end and a distal end disposed in the balloon interior;
- a diffuser, in the balloon interior, secured to and fluidly coupled with the distal end of the delivery tube;
- a second connector secured to the proximal end of the delivery tube, the second connector movable for both axial and rotary motion of the second connector, the delivery tube and the diffuser relative to the first connector, the catheter shaft lumen and the balloon interior; and
- a handle configured to connect to the second connector and provide the axial and rotary motion of the second connector, the delivery tube and the diffuser, wherein the computer instructions, when executed on one or more processors, cause the one or more processor to implement operations comprising:
- manipulating the second connector to cause simultaneous axial and rotary motions of the delivery tube and the diffuser relative to the first connector and the balloon interior, while supplying a refrigerant to the inner surface of the balloon interior through the diffuser during the axial and rotary motions of the diffuser, and wherein, when the second connector is connected to the handle for providing the axial and rotatory motion of the second connector, the second connector and the diffuser axially move along an axis while the handle remains the same axial distance from the catheter shaft.

17. The non-transitory computer-readable recording medium of claim 16, wherein the manipulating of the second connector to cause simultaneous axial and rotary motions and the supplying of the refrigerant are performed in dependence upon manual control of an operator.

18. The non-transitory computer-readable recording medium of claim 16, wherein the manipulating of the second connector to cause simultaneous axial and rotary motions and the supplying of the refrigerant are performed in dependence a preprogrammed and automated controller.

19. The non-transitory computer-readable recording medium of claim 16, wherein the computer instructions include treatment algorithms that allow for the manipulating of the second connector to cause simultaneous axial and rotary motions and the supplying of the refrigerant to be automated according to a preprogrammed therapy.

* * * * *